(12) United States Patent
Lee et al.

(10) Patent No.: US 6,416,861 B1
(45) Date of Patent: Jul. 9, 2002

(54) ORGANOSILICON COMPOUNDS AND USES THEREOF

(75) Inventors: Younghee Lee, Skokie; Richard B. Silverman, Northbrook, both of IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/504,217

(22) Filed: Feb. 15, 2000

Related U.S. Application Data

(60) Provisional application No. 60/120,088, filed on Feb. 16, 1999, and provisional application No. 60/145,165, filed on Jul. 22, 1999.

(51) Int. Cl.[7] .............................................. B32B 25/20
(52) U.S. Cl. ...................................... 428/391; 428/405
(58) Field of Search .......................... 556/420; 428/391, 428/405

(56) References Cited

U.S. PATENT DOCUMENTS

| | | | | |
|---|---|---|---|---|
| 4,180,515 A | * | 12/1979 | Bargain et al. | 260/448.2 Q |
| 4,213,914 A | * | 7/1980 | Bargain et al. | 556/419 |
| 4,263,436 A | * | 4/1981 | Bargain et al. | 546/14 |
| 5,256,706 A | * | 10/1993 | Carpenter et al. | 523/213 |
| 5,773,512 A | | 6/1998 | Chenera et al. | 525/100 |
| 6,127,489 A | * | 10/2000 | Newlander et al. | 525/342 |

FOREIGN PATENT DOCUMENTS

| | | |
|---|---|---|
| WO | WO 98/05671 | 2/1998 |
| WO | WO 98/17695 | 4/1998 |
| WO | WO 99/17869 | 4/1999 |

OTHER PUBLICATIONS

Boehm and Showalter; "Development of a Novel Silyl Ether Linker for Solid–Phase Organic Synthesis", *J. Org. Chem.*, 1996, 61, pp. 6498–6499.

Chan and Fleming; "Electrophilic Substitution of Organosilicon Compounds—Applications to Organic Synthesis"; Reviews; Oct. 1979, pp. 761–786.

Chenera et al.; "Protodetachable Arylsilane Polymer Linkages for Use in Solid Phase Organic Synthesis", *J. Am. Chem. Soc.*, 1995, 117, pp. 11999–12000.

Han et al.; "Silicon Directed ipso–Substitution of Polymer Bound Arylsilanes: Preparation of Biaryls via the Suzuki Cross–Coupling Reaction"; *Tetrahedron Letters*, 1996, vol. 37, pp. 2703–2706.

Hu et al.; "Novel Polymer–Supported Trialkylsilanes and Their Use in Solid–Phase Organic Synthesis"; *J. Org. Chem.*, 1998, 63, pp. 4518–4521.

Plunkett and Ellman; "Germanium and Silicon Linking Strategies for Traceless Solid–Phase Synthesis"; *J. Org. Chem.*, 1997, 62, pp. 2885–2893.

Woolard et al.; "A Silicon Linker for Direct Loading of Aromatic Compounds to Supports. Traceless Synthesis of Pyridine–Based Tricyclics"; *J. Org. Chem.*, 1997, 62, pp. 6102–6103.

\* cited by examiner

*Primary Examiner*—Margaret G. Moore
(74) *Attorney, Agent, or Firm*—Marshall, Gerstein & Borun.

(57) ABSTRACT

A compound of the formula:

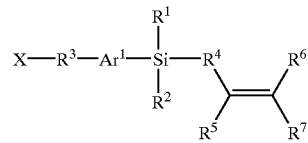

and a resin-bound compound of the formula:

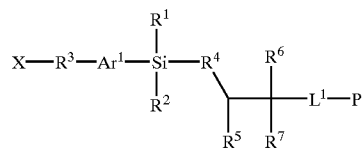

and their use in combinatorial chemistry and in the synthesis of compounds comprising at least one aromatic moiety is described, where $R^1$, $R^2$, $R^3$, $R^4$, $R^5$, $R^6$, $R^7$, $L^1$, P, $Ar^1$, and X are as herein defined.

9 Claims, No Drawings

ORGANOSILICON COMPOUNDS AND USES THEREOF

CROSS-REFERENCE TO RELATED APPLICATIONS

This application claims the benefit of U.S. Provisional Application Nos. 60/120,088, filed Feb. 16, 1999, and 60/145,165, filed Jul. 22, 1999.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. GM-49725 awarded by National Institute of Health.

FIELD OF THE INVENTION

The present invention provides organosilicon compounds containing an aromatic moiety group and methods for using the same for the solid-phase synthesis of libraries of compounds.

BACKGROUND OF THE INVENTION

Combinatorial chemistry, combined with recent advances in robotic screening which enable the testing of a large number of compounds in a short period of time, is becoming an important tool in accelerating drug discovery. This technique generally involves the preparation of a large number of structurally related compounds either as mixtures in the same reaction vessel or individually by parallel synthesis. In this manner large pools of similar compounds can be synthesized rather quickly. Combinatorial libraries have been prepared using both solution chemistry and by solid phase synthesis. Solid phase synthesis allows the use of excess reagents to drive the reaction to near completion, and easy removal of the reagents and side-products by simple washing with solvent. Therefore, solid phase synthesis generally offers a more attractive approach to the generation of combinatorial libraries.

One of the key elements in solid phase chemistry is the polymeric resin. Many of the resins which are currently employed were originally developed for the synthesis of peptides. Polar functionality such as carboxylic acids and amides were released upon cleavage of products from the resins. Recent advances in linker technology allowed other polar functional groups such as an alcohol and a thiol to be attached to the polymer support. However, most of the linkers available for solid support synthesis to date require polar functional groups for binding and release the same polar groups after cleavage. For the generation of libraries of biological activity, such polar functionalities may possess unfavorable pharmacological properties. In many cases, attempts have been made to render the lead compounds found in vitro less polar to increase the pharmacological properties such as high cellular uptake and hydrophobic membrane transport. Therefore, the focus in this field has been on designing new solid support linkers for non-polar or aromatic compounds which are commonly found in pharmaceutical agents.

To address this concern, several novel strategies utilizing resin. bound arylsilane as a "traceless linker" have been developed for solid phase synthesis of aromatics or heteroaromatic compounds. This method allows the attachment of substrates to the support at an inert site within the molecule. Upon cleavage from the resin by desilylation (with TFA, HF, or TBAF), no trace or "memory" of attachment to the polymer support is left. Also, silicone-directed ipso-substitution of arylsilanes is frequently used for regiospecific introduction of electrophilic functional groups such as bromine and iodine to the aromatic ring. (see for example, Chan et al., "Electrophilic substitution of organosilicon compounds. Applications to organic synthesis," *Synthesis* 1979, 761–786; Han et al., "Silicon directed ipso-substitution of polymer bound arylsilanes: Preparation of biaryls via the Suzuki cross reaction," *Tet. Lett.* 1996, 37, 2703–2706) Therefore, silicon-based linkers have been proved to be useful tools for the traceless synthesis of aromatics or halide substituted aromatics.

To date, several different arylsilane linkers have been devised and employed for the solid-phase synthesis of diverse aromatic systems. (see for example, Plunkett et al., "Germanium and silicon linking strategies for traceless solid-phase synthesis," *J. Org. Chem.* 1997, 62, 1885–2893; Chenera et al., "Protodetachable arylsilane polymer linkages for use in solid phase organic synthesis," *J. Am. Chem. Soc.* 1995, 117, 11999–12000; Boehm et al., "Development of a novel silyl ether linker for solid-phase organic synthesis," *J. Org. Chem.* 1996, 61, 6498–6499; Woolard et al., "A silicon linker for direct loading of aromatic compounds to supports. Traceless synthesis of pyridine-based tricyclics," *J. Org. Chem.* 1997, 62, 6102–6103, Hu et al., "Novel polymer-supported trialkylsilanes and their use in solid-phase organic synthesis," *J. Org. Chem.* 1998, 63, 4518–4521; and PCT Publication Nos. WO 98/05671 and WO 98/17695) Most of the known silicone linkers are generally designed to facilitate the solid-phase synthesis of focused libraries of aromatics, such as 1,4-benzodiazephines, biaryls, benzofurans, and tricyclics. Some of the silicone based linkers, [for example, (4-bromophenyl) diisopropylsilyloxymethyl polystyrene, (4-formylphenyl) diisopropylsilyloxymethyl polystyrene, and (4-trityloxyphenyl)diisopropylsilyloxymethyl polystyrene] from commercial sources are designed for the solid phase organic synthesis of substituted benzenes.

One of the limitations associated with the linkers described above is that linker itself has to be attached to the polymer by reaction of the polar group (alcohol, or carboxylic acid). Polar groups on the aromatic ring which would be utilized for attachment to the polymer requires protection/deprotection steps during the construction of other desired functional group on the aromatic. This protection/deprotection step requirement slows the construction of silyl linker. In addition, in some cases many functional groups can not be introduced due to compatibility problems. The other limitation of these linkers is that the appropriately functionalized aryl group must be first attached to the silicon linker, prior to attaching it to the solid support. Therefore, a separate linker must be prepared for each aryl group. To overcome this limitation, (4-methoxyphenyl) dimethylsilylpropyl polystyrene has been developed. Although this linker can be used to attach various aryllithiums or Grignard reagents to form the appropriate arylsilyl linkage, the application is still limited because other essential functional groups on the aryl ring must be able to tolerate strong basic conditions and/or must be protected.

Completely different class of linkers for traceless synthesis of arenes is triazine-based resins. Reaction of diazonium compound to the N-benzylaminomethyl polystyrene (or piperazinomethyl polystyrene) leads to formation of a polymer bound triazine. This functionality is stable under a wide range of reaction conditions (e.g., n-BuLi and DIBAL) but is readily cleaved by treatment with HCl in THF to liberate the aromatic moieties containing hydrogen at the original point of attachment. Although this approach is generally applicable to a wide range of simple anilines, other functional groups (which would be used for diversification) attached to the aniline are limited to ones which can tolerate acidic conditions employed for diazotization.

Despite these advances in a solid-support chemistry, there is a need for compounds which are useful in the solid-phase synthesis of aromatic containing molecules.

SUMMARY OF THE INVENTION

One embodiment of the present invention provides a compound of the formula:

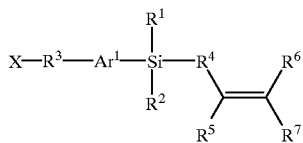

I wherein
each of $R^1$ and $R^2$ is independently aryl, $C_1$–$C_6$ alkyl, or $C_3$–$C_{20}$ cycloalkyl;
$R^3$ is a bond or $C_1$–$C_{10}$ alkylene;
$R^4$ is $C_1$–$C_{10}$ alkylene;
each of $R^5$, $R^6$ and $R^7$ is independently H or $C_1$–$C_6$ alkyl;
$Ar^1$ is aryl or heteroaryl; and
X is a functional group.

Another embodiment of the present invention provides a resin-bound compound of the formula:

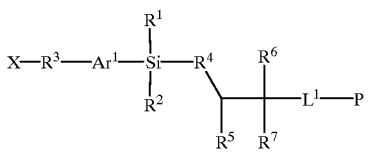

II where $Ar^1$, $R^1$, $R^2$, $R^3$, $R^4$, $R^5$, $R^6$, $R^7$, and X are those described above, $L^1$ is a bond or a link and P is a solid-support.

Another embodiment of the present invention provides a method for preparing a resin-bound compound comprising coupling a silane compound, preferably of formula I described above, to a polymeric resin using a transition metal, preferably palladium, mediated coupling reaction. Preferably, the silane compound comprises an alkenyl moiety, which allows a formation of silylalkylborane compound when the alkenyl moiety is contacted with a hydroborating agent. The silylalkylborane compound can be coupled to a polymeric resin which has an aryl halide moiety. In this manner, the coupling reaction results in a formation of a covalent bond between the carbon bonded to the boron atom and the carbon atom of the aryl halide moiety of the polymeric resin which is bonded to the halide.

The method of the present invention can also include linking the polymeric resin with a linker which has the above described aryl halide moiety. Preferably, the linker is of the formula $X^1$—Ph—C(=O)$OR^{13}$, where $X^1$ is a halide and $R^{13}$ is H or $C_1$–$C_6$ alkyl. It should be appreciated, however, that when the linker is linked to a resin containing an amine group, e.g., a moiety of the formula $H_2N$-(Resin), the resulting linker coupled resin will have an amide bond, e.g., the resulting linker coupled resin is of the formula: $X^1$—Ph—C(=O)—NH—(Resin).

Alternatively, the silylalkylborane compound can be oxidized to form a silylalkylhydroxy compound prior to the coupling step. Moreover, the hydroxy group of the silylalkylhydroxy compound can be converted to an amine, carboxylate or other functional groups to allow coupling with polymeric resins such as Merrifield resin, Wang resin, aminomethylated polystyrene resin, Rink resin, and aminomethylated Tentage) resin.

Still yet another embodiment of the present invention provides a method for preparing a library of compounds comprising an aromatic group, wherein the aromatic group comprises an aryl group or a heteroaryl group. Methods for generating a library of compounds include:

(a) preparing a plurality of resin-bound compounds described above;
(b) optionally dividing the resin-bound compounds into a plurality of portions;
(c) performing additional synthetic chemistry to modify the functional group X to produce modified resin-bound compounds;
(d) optionally recombining the portions; and
(e) cleaving at least a portion of the modified resin-bound compounds from the polymeric resin supports so that the aromatic groups resulting from the cleavage have a hydrogen, halide, hydroxy or acyloxy group on the aromatic carbon which were bound to the polymeric resin through the silyl group.

The steps of (b) dividing resin-bound compounds, (c) performing additional synthetic chemistry, and (d) combining the portions can be repeated to generate larger compounds.

The compounds can be cleaved from the polymeric resin support by treatment with a cleaving agent including an acid, a fluoride ion source, an electrophile, and mixtures thereof.

By using a suitable assay, compounds or libraries of compounds of the present invention can be tested to identify or determine a ligand for a particular receptor.

DETAILED DESCRIPTION OF THE INVENTION

The standard method for conducting a search for new chemical moieties that can effectively modulate a variety of biological processes is to screen a variety of pre-existing chemical moieties, for example, naturally occurring compounds or compounds which exist in synthetic libraries or databanks. The biological activity of the pre-exiting chemical moieties is typically determined by applying the moieties to an assay which has been designed to test a particular property of the chemical moiety being screened, for example, a receptor binding assay which tests the ability of the moiety to bind to a particular receptor site.

In an effort to reduce the time and expense involved in screening a large number of randomly chosen compounds for biological activity, several developments have been made to provide libraries of compounds for the discovery of lead compounds. The chemical generation of molecular diversity has become a major tool in the search for novel lead structures. Currently, the known methods for chemically generating large numbers of molecularly diverse compounds generally involve the use of solid phase synthesis, in particular to synthesize and identify peptides and peptide libraries.

The present invention provides compounds which are useful for solid-phase synthesis of not only peptides but also for non-peptide compounds, methods for linking these compounds to functionalized solid supports (e.g., halogenated polystyrene resin), methods for using the solid-support bound compounds to generate libraries of compounds, and methods for using them in screening processes. In particular, compounds of the present invention include a functionalized aryl moiety. Specifically, compounds of the present invention have the following general formula:

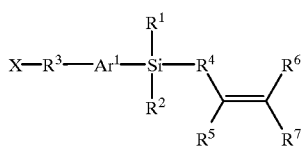

I where each of $R^1$ and $R^2$ is independently aryl, $C_1$–$C_6$ alkyl, or $C_3$–$C_{20}$ cycloalkyl, preferably, $R^1$ and $R^2$ are methyl; $R^3$ is a bond or $C_1$–$C_{10}$ alkylene, preferably $R^3$ is a bond or $C_1$–$C_6$ alkylene; $R^4$ is $C_1$–$C_{10}$ alkylene, preferably $R^4$ is methylene (i.e., —$CH_2$—); each of $R^5$, $R^6$ and $R^7$ is independently H or $C_1$–$C_6$ alkyl, preferably $R^5$, $R^6$ and $R^7$ are H; $Ar^1$ is aryl or heteroaryl, preferably $Ar^1$ is optionally substituted phenyl, naphthyl, thiophenyl, pyridyl, biphenyl, quinolinyl, thiazinyl, isoquinolinyl, imidazolyl, furanyl, fluorenyl, indolyl, or indanyl; and X is a functional group, preferably X is a halide, substituted aryl or heteroaryl, or a moiety of the formula —$NR^8R^9$, —$NHNR^{10}$, —$OR^{11}$, —$SR^{12}$, —CN, —CHO, —$CO_2R^{13}$, —$CR^{14}CR^{15}CO_2R^{13}$, —$C(=O)NR^{16}R^{17}$, —$CR^{14}=CR^{15}C(=O)NR^{16}R^{17}$, —CH[$CH_2(NR^8R^9)$]$CO_2R^{13}$, or —CH($NR^8R^9$)$CO_2R^{13}$, where each of $R^8$ and $R^9$ is independently H, $C_1$–$C_6$ alkyl, or an amine protecting group, $R^{10}$ is H, $C_1$–$C_6$ alkyl, or a hydrazine protecting group; $R^{11}$ is H, $C_1$–$C_6$ alkyl, or a hydroxy protecting group; $R^{12}$ is H, $C_1$–$C_6$ alkyl, or a thiol protecting group; each of $R^{13}$, $R^{14}$, and $R^{15}$ is independently H, or $C_1$–$C_6$ alkyl; and each of $R^{16}$ and $R^{17}$ is independently H, $C_1$–$C_6$ alkyl, or an amide protecting group. More preferably, X is substituted aryl or heteroaryl, —$NHR^9$, —$NHNR^{10}$, —$OR^{11}$, —$SR^{12}$, —CN, —CHO, —$CO_2R^{13}$, —CH=$CHCO_2R^{13}$, —CH[$CH_2(NR^8R^9)$]$CO_2R^{13}$, or —CH($NR^8R^9$)$CO_2R^{13}$.

The term "alkyl" refers to aliphatic hydrocarbons which can be straight or branched chain groups. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, difluoromethyl, trifluoromethyl, chloromethyl, trichloromethyl, and pentafluoroethyl.

The term "aryl" refers to aromatic ring moieties including carboaryls, such as mono- and bicyclic aromatic carbocyclic ring moieties; and heteroaryls, i.e., aromatic ring moieties containing one or more heteroatoms, such as mono- and bicyclic aromatic heterocyclic ring moieties. Aryl groups can be substituted with one or more substituents, such as a halogen, alkenyl, alkyl, alkynyl, hydroxy, amino, thio, alkoxy or cycloalkyl. Exemplary aryls include pyrrole, thiophene, furan, imidazole, pyrazole, 1,2,4-triazole, pyridine, pyrazine, pyrimidine, pyridazine, thiazole, isothiazole, oxazole, isoxazole, s-triazine, benzene, indene, isoindene, benzofuran, dihydrobenzofuran, benzothiophene, indole, 1H-indazole, indoline, azulene, tetrahydroazulene, benzopyrazole, benzoxazole, benzoimidazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benisoxazine. Preferably, aryl is optionally substituted phenyl, naphthyl, thiophenyl, pyridyl, bi-phenyl, quinolinyl, thiazinyl, isoquinolinyl, imidazolyl, furanyl, fluorenyl, indolyl, or indanyl.

The compounds of the present invention provide a variety of different functional groups upon which further chemical reaction can be performed to generate libraries of compounds. The terms "additional synthetic chemistry" and "further chemical reaction" are used interchangeably herein to mean one or a series of chemical reactions which are performed to modify or derivatize functional group X. Preferably, additional synthetic chemistry is performed on a resin-bound compound, discussed in detail below, prior to cleavage of the aryl group from the resin-bound compound. Further chemical reactions are selected such that the chemical reactions are compatible with and non-reactive with the aryl silane bond and may be used to prepare derivatives of the aryl compound. It will be recognized by the one skilled in the art that the additional synthetic chemistry performed on the resin-bound compound is done prior to cleavage of the aryl silane bond. Chemical reactions which are compatible with the resin-bound compound include reactions which effectuate the swelling of the polymeric resin thereby allowing penetration of the reagents to react with the functional group X. It should be appreciated that additional synthetic chemistry or further chemical reaction does not include chemical reactions which are reactive with the aryl silane bond. Chemical reaction which cleave the aryl silane bond is herein referred to as a "cleaving reaction" to indicate that they cause cleavage of the aryl silane bond. Chemical reagents which are useful in cleaving reactions, i.e., cleaving agent, include acids, fluoride ion sources, electrophiles, and mixtures thereof. Preferably, the cleaving agent is trifluoroacetic acid, HF, pyridinium hydrofluoride, CsF, tetrabutylammonium fluoride, $Br_2$, $Cl_2$, ICl, or mixtures thereof.

The present invention also provides a method for preparing a resin-bound compound comprising coupling a silane compound to a polymeric resin using a transition metal. Preferably, the silane compound comprises an alkenyl moiety, which allows a formation of silylalkylborane compound when the alkenyl moiety is contacted with a hydroborating agent. Preferably, the hydroborating agent is of the formula $HBR^{18}R^{19}$, where each of $R^{18}$ and $R^{19}$ is independently H, $C_1$–$C_{10}$ or $R^{18}$ and $R^{19}$ together form $C_3$–$C_{20}$ cycloalkyl. Preferred hydroborating agents include 9-BBN, $BH_3$, thexyl borane and other hydrogen containing boranes which are known to one of ordinary skill in the art. More preferably, the silane compound is a compound of formula I above, in which case the resulting resin-bound compound is of the formula:

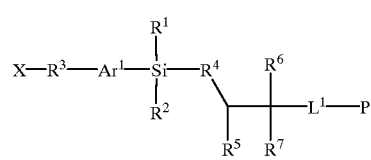

II where $R^1$, $R^2$, $R^3$, $R^4$, $R^5$, $R^6$, $R^7$, X and $Ar^1$ are those described above; $L^1$ is a bond or a linker preferably $L^1$ is a bond, —O—, or a moiety of the formula —NHC(=O)—Ph—C(=O)NH—CH$_2$—P, where Ph is phenyl; and P is a solid-support. When L$^1$ is a moiety of the formula —NHC(=O)—Ph—C(=O)NH-CH$_2$—P, the two amide functional groups can be located on ortho-, meta- or para-position relative to each other, preferably meta or para position, of the phenyl group.

The terms "solid-support," "resin," "polymeric resin," "polymer support" and "polymeric resin support" are used interchangeably to refer to a bead or other solid support such as beads, pellets, disks, capillaries, hollow fibers, needles, solid fibers, cellulose beads, pore-glass beads, silica gels, grafted co-poly beads, polyacrylamide beads, latex beads, dimethylacrylamide beads optionally cross-linked with N,N'-bis-acryloyl ethylene diamine, glass particles coated with a hydrophobic polymer, etc., i.e., a material having a rigid or semi-rigid surface. The solid support is suitably made of, for example, cross linked polystyrene resin, polyethylene glycol-polystyrene resin, benzyl ester resins or benzhydrylamine resins and any other substance which may be used as such and which would be known or obvious to one of ordinary skill in the art. For purposes herein, it will be obvious to the skilled artisan, that the above terms mean any aliphatic or aromatic polymer which lacks functionality known to participate in the additional synthetic chemistry for generation of the derivatized compounds of this invention, and which is stable to conditions for protodesilylation. Preferred solid-supports for use herein are polystyrene, aminomethylated polystyrene resin, the Tentagel resin, aminomethylated Tentagel resin, polyamide-kieselguhr composites, the Merrifield resin, the Wang resin, and the Rink resin. Preferred polymer resins for use herein are the Merrifield resin (available commercially from Nova Biochem) and the Wang resin (synthesis described below).

In addition, when the silane compound is a compound of formula I above, the silyalkylborane compound which is produced by hydroboration of compound I is of the formula:

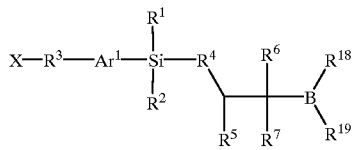

where R$^1$, R$^2$, R$^3$, R$^4$, R$^5$, R$^6$, R$^7$, R$^{18}$, R$^{19}$, Ar$^1$, and X are those described above.

The silylalkylborane compound can be coupled to a polymeric resin which includes an aryl halide moiety. In this manner, the coupling reaction results in a formation of a covalent bond between the carbon bonded to the boron atom and the carbon atom of the aryl halide moiety of the polymeric resin which is bonded to the halide. Such coupling can be affected by a transition metal catalyzed coupling reaction which are well known to one of ordinary skill in the art. For example, alkylboranes, including silylalkylboranes, can be coupled to an aryl halide using a palladium catalyzed cross-coupling reaction, which is typically known as the Suzuki reaction. Particular palladium catalysts which are useful in the Suzuki reaction are well known to one of ordinary skill in the art. Alternatively, the silane compound can be converted to a Grignard reagent, e.g., by reaction of an alkyl halide with magnesium metal, and coupled to a solid-support containing an aryl halide moiety by using a transition metal.

The method of the present invention can also include linking the polymeric resin with a linker, e.g., L$^1$ of formula II, which include an aryl halide moiety. Preferably, the linker is of the formula X$^1$—Ph—C(=O)OR$^{13}$, where X$^1$ is a halide, preferably X$^1$ is Cl, Br or I; and R$^{13}$ is described above. The X$^1$ group of the linker may be located on ortho-, or preferably meta- or para-position relative to the —C(=O)OR$^{13}$ moiety of the linker.

Alternatively, the silylalkylborane compound can be oxidized to form a silylalkylhydroxy compound prior to the coupling step. Moreover, the hydroxy group of the silyalkylhydroxy compound can be converted to an amine, carboxylate or other functional groups to allow coupling with polymeric resins such as Merrifield. resin, Wang resin, aminomethylated polystyrene resin, Rink resin, and aminomethylated Tentagel resin.

Still yet another embodiment of the present invention provides a method for preparing a library of compounds comprising an aryl group. Methods for generating a library of compounds include:

(a) preparing a plurality of resin-bound compounds;

(b) optionally dividing the resin-bound compounds into a plurality of portions;

(c) performing additional synthetic chemistry to modify the functional group X to produce modified resin-bound compounds;

(d) optionally recombining the portions; and (e) cleaving at least a portion of the modified resin-bound compounds from the polymeric resin supports so that the aryl groups resulting from the cleavage have a hydrogen, halide, hydroxy or acyloxy group on the aryl carbon atom which were bound to the polymeric resin through the silyl group.

The steps of (b) dividing resin-bound compounds, (c) performing additional synthetic chemistry, and (d) combining the portions can be repeated as many times as desired to generate larger compounds.

The compounds (or libraries of compounds) made by the instant methods may either remain bound to the resin which is used to perform the resin-bound synthesis (hereinafter referred to as "resin-bound compounds (or libraries)") or not bound to a resin (hereinafter referred to as "soluble compounds (or libraries)"). For example, the resin-bound compounds can be cleaved from the polymeric resin support by treatment with a cleaving agent including an acid, a fluoride ion source, an electrophile, and mixtures thereof. Thus, the cleaved compounds can have a hydrogen, halogen, hydroxy or acyloxy group bound to the aryl carbon atom which was bound to the silyl group after cleavage from the solid-support. Preferably, the cleaving agent is trifluoroacetic acid, HF, pyridinium hydrofluoride, CsF, tetrabutylammonium fluoride, Br$_2$, Cl$_2$, ICl, or mixtures thereof.

The terms "resin-bound synthesis" and "solid phase synthesis" are used herein interchangeably to mean one or a series of chemical reactions used to prepare either a single compound or a library of molecularly diverse compounds, where the chemical reactions are performed on a compound, which is bound to a polymeric resin support.

Based upon the disclosure herein, it will be clear to one of ordinary skill in the art that there are many possible synthetic approaches to creating the libraries of this invention. The libraries can be prepared on a solid support, e.g., a resin, or they can be prepared in solution. For example, the variable substituents can be added by reacting core structure, labeled R, with a mixture of reagents designed to introduce substituents X$_{1-m}$ collectively or by reacting aliquots of R with individual reagents each one of which will introduce a single substituent R$_i$ and then mixing the resultant products together (wherein i, j and k are used herein to represent any of the substituents on the compound members of the combinatorial library).

For reasons of efficiency, the components of the library are screened in groups of multiple compounds. Therefore, once the library of compounds has been synthesized, there must be some method to deconvolute the results of screening such that individual active compounds can be identified. Based upon the disclosure herein, it will be clear to one of ordinary skill in the art that there are many methods for deconvolution of the combinatorial library. For example, if the compounds of the library are screened on a solid support, they may be physically segregated so that individual active compounds may be directly selected and identified. In contrast, if the compounds of the library are tested as soluble mixtures, e.g., after cleaving from the solid-support, the library may be deconvoluted in an iterative approach, which involves resynthesis of mixtures of decreasing complexity until a single compound is identified, or in a scanning approach, in which the various substituents on the core structure, are evaluated independently and the structure of active compounds are determined deductively.

In its simplest form, the iterative approach to deconvoluting the combinatorial library involves separation of the combinatorial library of compounds immediately prior to the introduction of the last variable substituent. Using the same nomenclature, i.e., R is the core structure, etc., as used above, the mixture of compounds $RX_{1-m}Y_{1-n}$ is partitioned into p aliquots (wherein m, n and p are integers which define the size of the library, and which range between 1 to 1000; preferably between 1 to 100, most preferably between 1 to 20). Each of those aliquots is reacted with reagents designed to introduce a single substituent, labeled Z. Thus, p different pools $RX_{1-m}Y_{1-n}Z_i$, each of which contains (m×n) compounds with all possible variations of X and Y being represented but only one particular Z, will be obtained. Screening this library in a binding or functional assay defines the appropriate Z substituent(s) for the desired activity. The term "assay" refers to a binding assay or a functional assay known or obvious to one of ordinary skill in the art for a particular purpose.

Once the appropriate Z substituent, labeled $Z_a$, is determined (for illustrative purposes, only one active compound exists, however, it would be clear to one of ordinary skill in the art that more than one active compound may exist in the library), the library is prepared again, this time splitting the mixture of compounds $RX_{1-m}$ into n aliquots for introduction of the n different Y substituents (as used herein "a", "b" and "c" refer to specific acceptable substituents which have been determined to be active by screening in a binding or functional assay). After the Y substituents are introduced, the $Z_a$ substituent is introduced into each of the still separated aliquots. The library now consists of n pools $RX_{1-m}Y_jZ_a$, each of which contains m different compounds with all the possible X substituents. represented, and one particular Y substituent. Screening this library in a binding or functional assay defines the appropriate Y substituent, labeled $Y_b$.

In a similar manner, the appropriate X substituent, labeled $X_c$ is determined by beginning with m different aliquots of core structure R and sequentially introducing $X_k$, $Y_b$ and $Z_a$ to give m different pools $RX_kY_bZ_a$, each of which contains a single compound. Thus only m+n+p syntheses are required to deconvolute a library containing (m×n×p) compounds.

The iterative approach is specific for a single target which is determined after the first round of screening, since subsequent library preparations do not contain the full complement of substituents.

The application of the scanning approach to deconvoluting the combinatorial library requires that the variable substituents X, Y and Z can be introduced synthetically independently of each other. The library is first prepared as $RX_{1-m}Y_{1-n}Z_i$ exactly as in the iterative approach to give p pools $RX_{1-m}Y_{1-n}Z_i$, each of which contains (m×n) compounds with all possible variation of X and Y represented but only one particular Z. Screening this library defines the appropriate Z substituents for the desired activity.

Since Y can be introduced independently from X and Z, the library is then prepared as $RX_{1-m}Y_jZ_{1-p}$, giving n pools of compounds each containing (m×p) compounds in which all substituents X and Z are represented with a particular Y substituent. Screening this library in a binding or functional assay defines the appropriate Y substituents for the desired activity.

Since X can also be introduced independently from Y and Z, the library is then prepared as $RX_kY_{1-n}Z_{1-p}$, giving m batches or pools of compounds, each of which contains (n×p) compounds in which all substituents Y and Z are represented with a particular X substituent. Screening this library in a binding or functional assay defines the appropriate X substituents for the desired activity. The terms "batches" or "pools" are used interchangeably and refer to a collection of compounds or compound intermediates.

In the simplest case, a single X, Y and Z substituent are identified from the three libraries, thus converging on a single compound $RX_cY_bZ_a$. The advantage of utilizing the scanning approach is that each library contains all the possible permutations of X, Y and Z and can be utilized to screen against a number of different biological targets.

Compounds of the present invention may be useful in a variety of applications including in a synthesis of other organic chemicals, including α- and β-amino acids, peptides, such as sansalvamide, leualacin, astin G, pristinamycin I and lissoclinum cyclopeptides; and as receptor ligands, including aspartyl protease inhibitors (such as HIV protease, renin, and cathepsins D and E), farnesyltransferase inhibitors, cyclooxygenase (COX-2) inhibitors, GP IIbIIIa antagonists, and ligands to somatostatin receptors. Suitable assays for identifying or determining a ligand for a particular receptor are well known to one of ordinary skill in the art. Thus, compounds prepared by the methods described herein can be screened in assays developed for determining lead compound as pharmaceutical agents.

The resin-bound compounds of the present invention provide several different functional groups upon which allows further chemical reactions to generate libraries of compounds. A variety of drugs and/or biologically active agents, in particular compounds containing a bulky hydrophobic moiety, can be synthesized on the solid-support using the compounds and methods described herein, including α- and β-amino acids attached to the solid-support through its aromatic side chain by silyl linkage, silylated-aromatics with various functional groups such as bromo-, hydroxy-, and amino-alkyl, formyl, carboxylic acid. In particular, phenylalanine-containing dipeptide analogs, β-homophenylalanine-containing tripeptide analogs, benzyl or phenethyl-containing secondary amines, benzyl substituted sulfonamides, N-benzylated peptidomimetics can be synthesized on the solid-support in high yield and purity.

The compounds of the present invention can be synthesized from readily available starting materials. Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in *Protective Groups in Organic Synthesis*, 3rd edition, T. W. Greene and P. G. M. Wuts, John Wiley & Sons, New York, 1999, which is incorporated herein by reference in its entirety. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art.

It is to be understood that the scope of this invention encompasses not only the various isomers which may exist but also the various mixture of isomers which may be formed.

If the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein by reference in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

When the compound of the present invention contains an olefin moiety and such olefin moiety can be either cis- or trans-configuration, the compound can be synthesized to produce cis- or trans-olefin, selectively, as the predominant product. Alternatively, the compound containing an olefin moiety can be produced as a mixture of cis- and trans-olefins and separated using known procedures, for example, by chromatography as described in W. K. Chan, et al., *J. Am. Chem. Soc.*, 1974, 96, 3642, which is incorporated herein in its entirety.

For all of the following Schemes, standard work-up and purification methods can be used and will be obvious to one of ordinary skill in the art. In addition, it will be recognized that the aryl group coupled to the polymer resins through the silyl group illustrated below, can be optionally substituted at any appropriate site, depending upon the type of derivatization required.

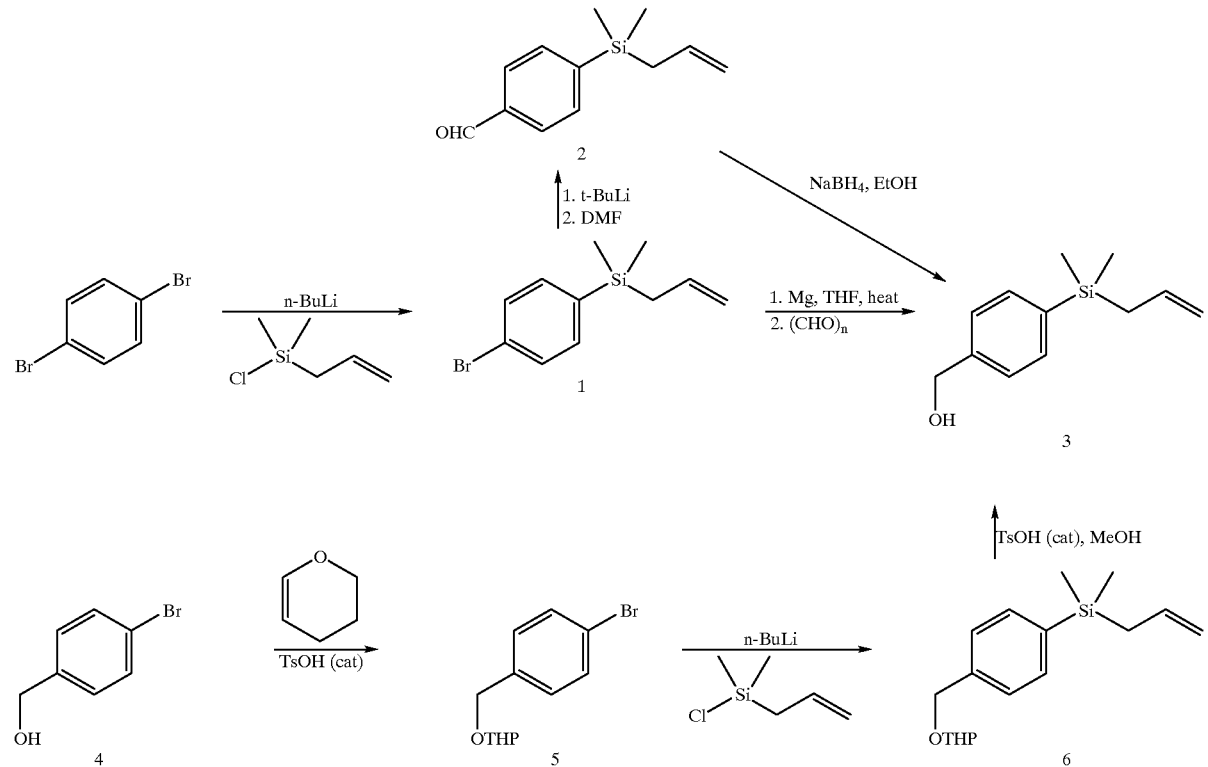

Scheme 1

One method for preparing a representative compound of the present invention, i.e., 4-allyldimethylsilylbenzyl alcohol (3 Scheme 1) is shown in Scheme 1. As used herein, the term "(x Scheme y)" refers to compound number x in Scheme Y. A metal-halogen exchange reaction of the starting 1,4-dibromobenzene with n-butyllithium followed by addition of allylchlorodimethylsilane produces aryl sliane (1 Scheme 1). Treatment of (1 Scheme 1) with magnesium in THF generated Grignard reagent which was reacted with paraformaldehyde to afford (3 Scheme 1). Alternatively, reaction of (1 Scheme 1) with t-butyllithium followed by quenching with anhydrous DMF produced 4-allyldimethylsilylbenzaldehyde (2 Scheme 1). Reduction of 4-allyldimethylsilylbenzaldehyde with sodium borohydride gave (3 Scheme 1).

Alternatively, protection of 4-bromobenzyl alcohol (4 Scheme 1) with THP, followed by lithium-halogen exchange with n-butyllithium and treatment with allylchlorodimethylsilane afforded the arylsilane (6 Scheme 1). Removal of the THP group with TsOH gave 4-allyldimethylsilylbenzyl alcohol (3 Scheme 1).

Conventional solid-phase peptide synthesis allows the elongation of the amino acid backbone in unidirection (C to N or N to C). A more efficient approach to the synthesis of peptides involves the anchoring of the side chain to the polymer, an approach that has been utilized, especially for head-to-tail cyclization of cyclic peptides. This methodology provides minimal risks for side reactions, such as dimerization and oligomerization, even under reaction conditions of high concentration. Furthermore, this side-chain anchoring strategy allows the generation of more diverse libraries of compounds than the conventional unidirectional methods. This bi-directional functionalization is especially applicable for preparing compounds whose C- and N-terminals are both capped with non-amino acids. Because the conventional linkers are mainly based on the polar functional groups, this method has been applicable only to amino acids which have polar side chains such as Asp, Glu (COOH); Ser, Tyr (OH); Lys ($NH_2$); or His (imidazole). For the amino acids which have a hydrophobic aliphatic or aromatic carbon chain, a side chain anchoring strategy for solid phase synthesis has not been reported.

Because of the non-polar nature and steric bulkiness of its side chain, phenylalanine is one of the preferred residues in peptidomimetics for favorable interaction with biological targets. Almost every aspartyl protease, such as HIV protease, renin, cathepsins D and E, has a preference for hydrophobic amino acid side chains at the $P_1$ position; consequently, peptidomimetics designed to inhibit these enzymes generally contain phenylalanine mimics or other bulky hydrophobic groups at $P_1$ position. A large number of naturally occurring linear peptides with antineoplastic activity, such as Dolastatin 10 and 15, and numerous cyclic peptides that are hydrophobic also contain at least one phenylalanine residue.

As shown in Schemes 2–4, the present invention provides one of the most efficient methods for producing a library of phenylalanine-containing molecules by providing a resin-bound compounds in which the phenylalanine side chain is attached to the polymer support, thus allowing both the N- and C-termini to be varied independently.

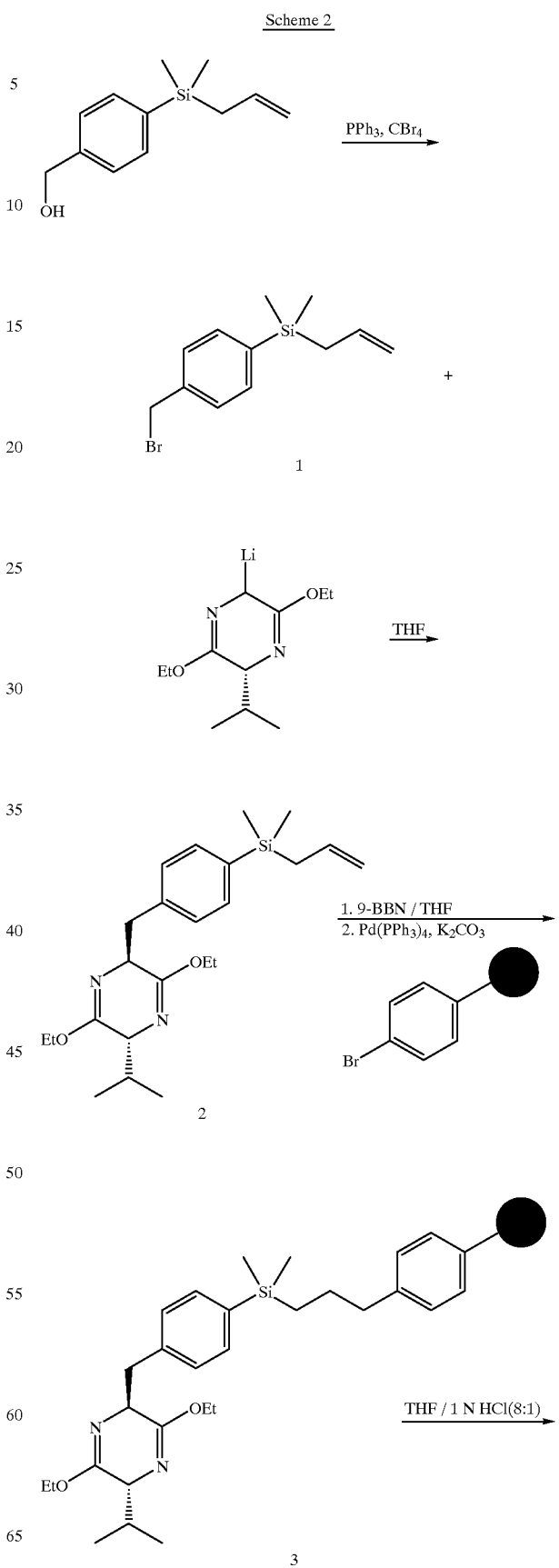

Scheme 2

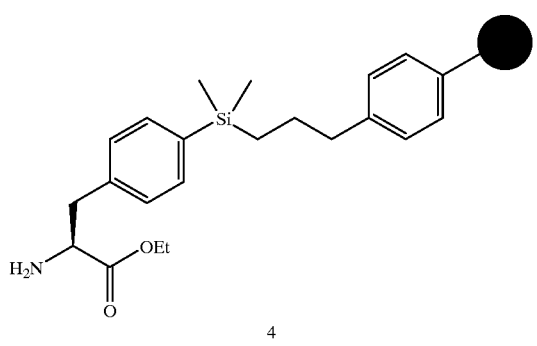

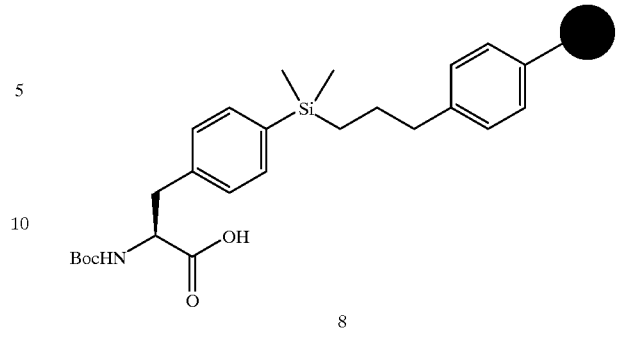

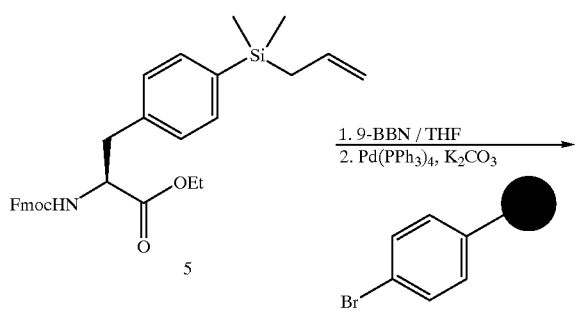

Bromination of 4-allyldimethylsilylbenzyl alcohol (3 Scheme 1) was carried out with triphenylphosphine and carbon tetrabromide. To insure high diastereoselectivity of the product, carbon-carbon bond formation between the benzyl bromide (1 Scheme 2) and lithiated bislactim ether was performed by a slow addition of benzyl bromide (1 Scheme 2) in dry THF to the lithiated bislactim ether stirred at −78° C. in THF. This amino acid precursor with an allyldimethysilyl functional group was linked to the polymer by two step sequences. Hydroboration of the allylsilane (2 Scheme 2) with 9-BBN followed by in situ Suzuki coupling with bromopolystyrene provided a resin bound phenylalanine derivative (3 Scheme 2). Treatment of the resin with a solution of THY/1N HCl (8:1) for 3 h at room temperature afforded phenylalanine ethyl ester (4 Scheme 2) which is ready for further derivatization on a polymer support.

Alternatively, the bislactim ether (2 Scheme 2) was hydrolyzed under mild acidic conditions to obtain the amine which was protected as an N-Fmoc carbamate (5 Scheme 2) or N-Boc carbamate (7 Scheme 2). The same coupling conditions as described above provided the resin bound phenylalanine derivatives (6 Scheme 2) and (8 Scheme 2), respectively. The loading level of the amino acid derivatives bound to the polymer was determined by the Fmoc release UV/VIS assay or by mass balance of the corresponding bromo analog released from the resin after brief treatment of the resin with $Br_2$ in dichloromethane.

Scheme 3

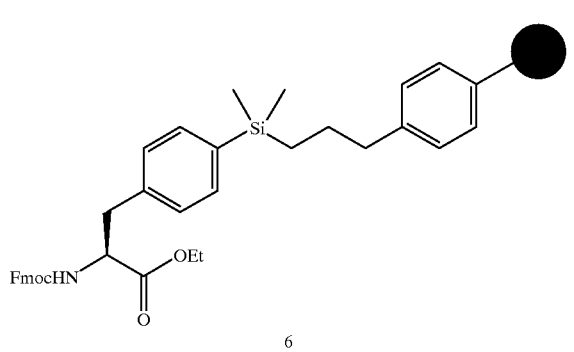

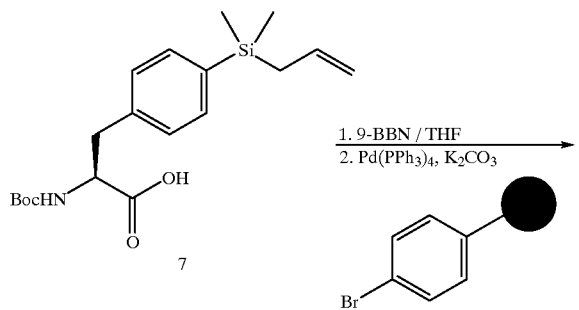

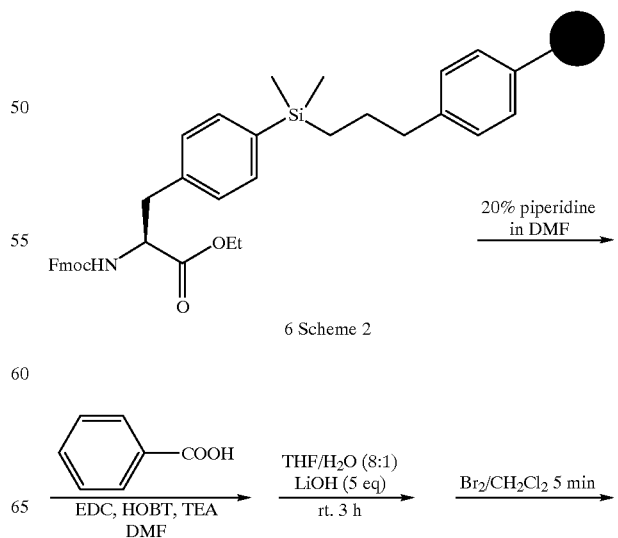

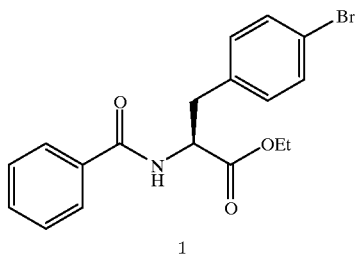

1

As illustrated in Scheme 3, to extend the N-terminal of (6 Scheme 2), Fmoc group was removed, the free amide group was coupled with benzoic acid, the resulting product was treated with LiOH (5 eq) in THF/H$_2$O (8:1) for 3 h at room temperature. Cleavage of the compound was carried out with Br$_2$ to release the ester (1 Scheme 3). The ester can be hydrolyzed by heating in the presence of LiOH.

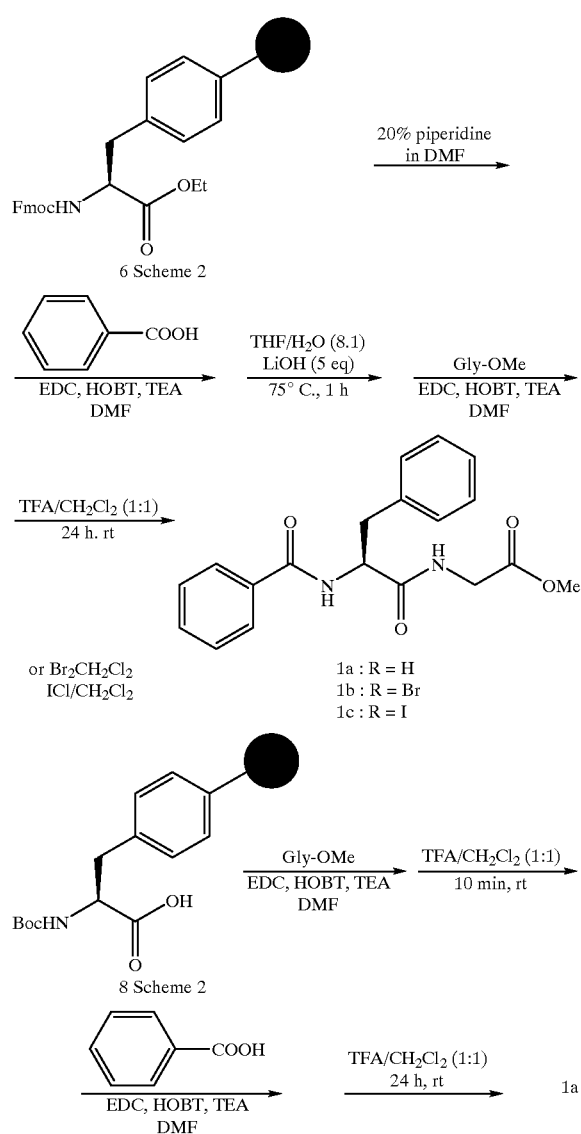

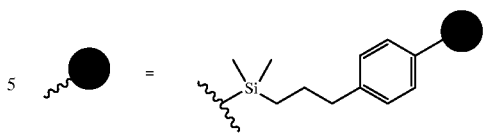

The utility of the polymer bound phenylalanine precursor is demonstrated by the preparation dipeptide analogues from both the N- and C-termini as shown in Scheme 4. Deprotection of Fmoc group followed by coupling with benzoic acid gave an N-benzoyl amide. Hydrolysis of the ester was carried out under the standard hydrolysis conditions (i.e., LIOH (5 eq) in THF/H$_2$O (8:1) for 1 h at 75° C.), then the C-terminal coupling was performed on this carboxylic acid with glycine methyl ester. The dipeptide analogue was cleaved from the resin with 50% TFA to yield protected dipeptide (1a Scheme 4). Alternatively, cleavage of the dipeptides from the resin by ipso-substitution of the silyl group with electrophiles (Br$_2$ or ICl) gave the corresponding halogen-substituted compounds (1b Scheme 4 and 1c Scheme 4).

Similarly, but in a reverse reaction sequence, the same compound (1a Scheme 4) was synthesized on the solid support starting from the N-Boc-protected phenylalanine precursor (6 Scheme 2). C-terminal amide coupling with glycine methyl ester followed by deprotection of the Boc group with 50% TFA, and subsequent coupling with benzoic acid, afforded dipeptide (1a Scheme 4) after cleavage from the resin. The polymer-bound phenylalanine can be modified in either the N- or C-terminal direction with readily available reagents, such as amines and carboxylates, and diversity can be further increased by cleaving the peptide from the resin with halogens to give para-substituted halophenylalanines. These halogenated analogues can be further elaborated by variety of alkyl or aryl substitution reactions at the halide.

This method can be applied to cyclic peptide synthesis by head-to-tail cyclization of a peptide on a solid support.

The arylsilyl linkage in the compounds of the present invention is generally resistant to moderate acidic [1 N HCl/THF (1:8); 50% TFA/CH$_2$Cl$_2$ for 10 min] and basic conditions [LiOH, THF/H$_2$O (8:1), heat] as well as to the general amide coupling reactions.

Scheme 5

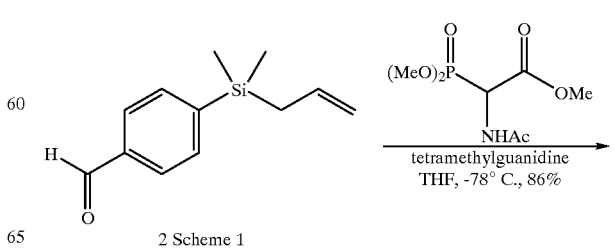

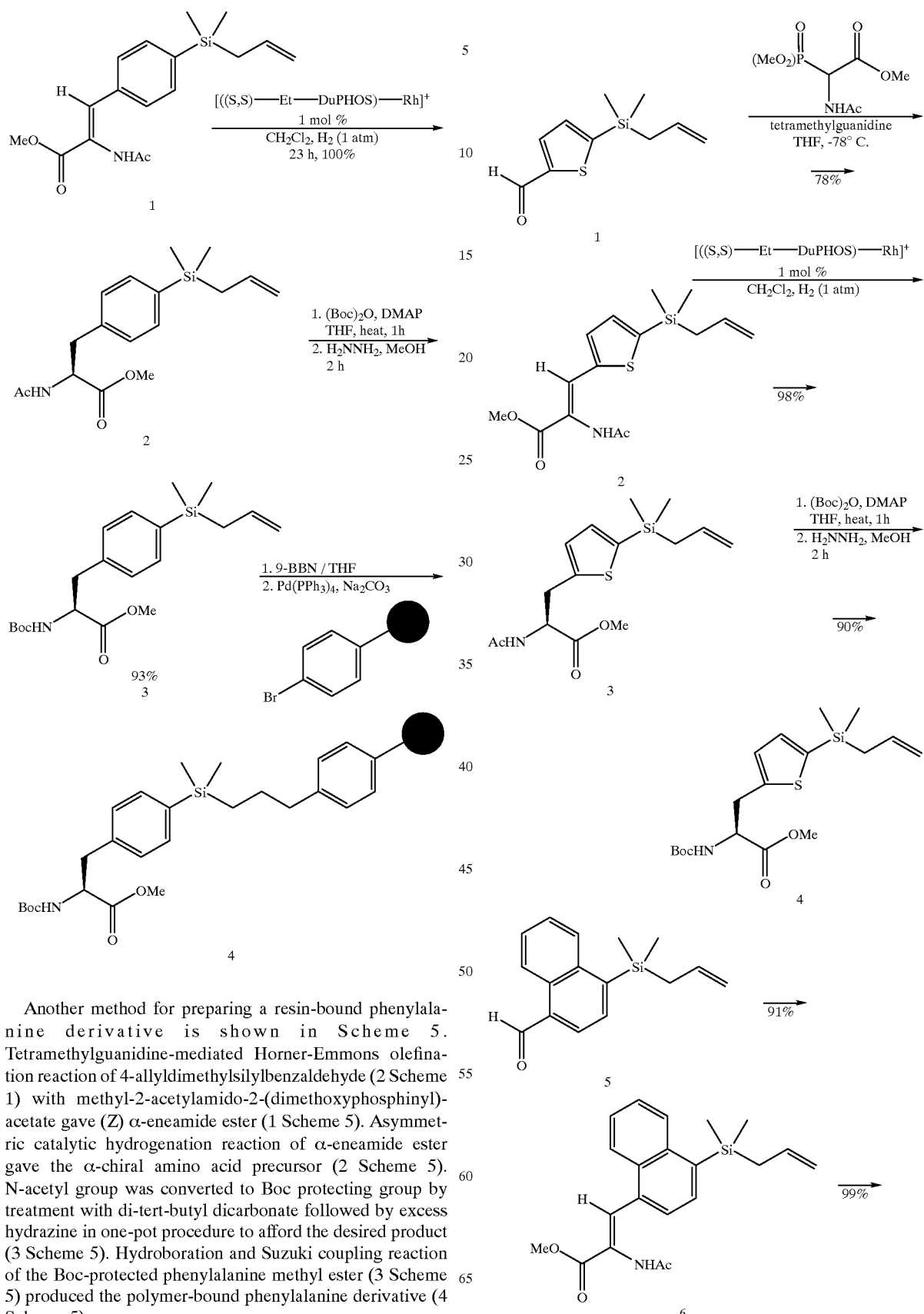

Another method for preparing a resin-bound phenylalanine derivative is shown in Scheme 5. Tetramethylguanidine-mediated Horner-Emmons olefination reaction of 4-allyldimethylsilylbenzaldehyde (2 Scheme 1) with methyl-2-acetylamido-2-(dimethoxyphosphinyl)-acetate gave (Z) α-eneamide ester (1 Scheme 5). Asymmetric catalytic hydrogenation reaction of α-eneamide ester gave the α-chiral amino acid precursor (2 Scheme 5). N-acetyl group was converted to Boc protecting group by treatment with di-tert-butyl dicarbonate followed by excess hydrazine in one-pot procedure to afford the desired product (3 Scheme 5). Hydroboration and Suzuki coupling reaction of the Boc-protected phenylalanine methyl ester (3 Scheme 5) produced the polymer-bound phenylalanine derivative (4 Scheme 5).

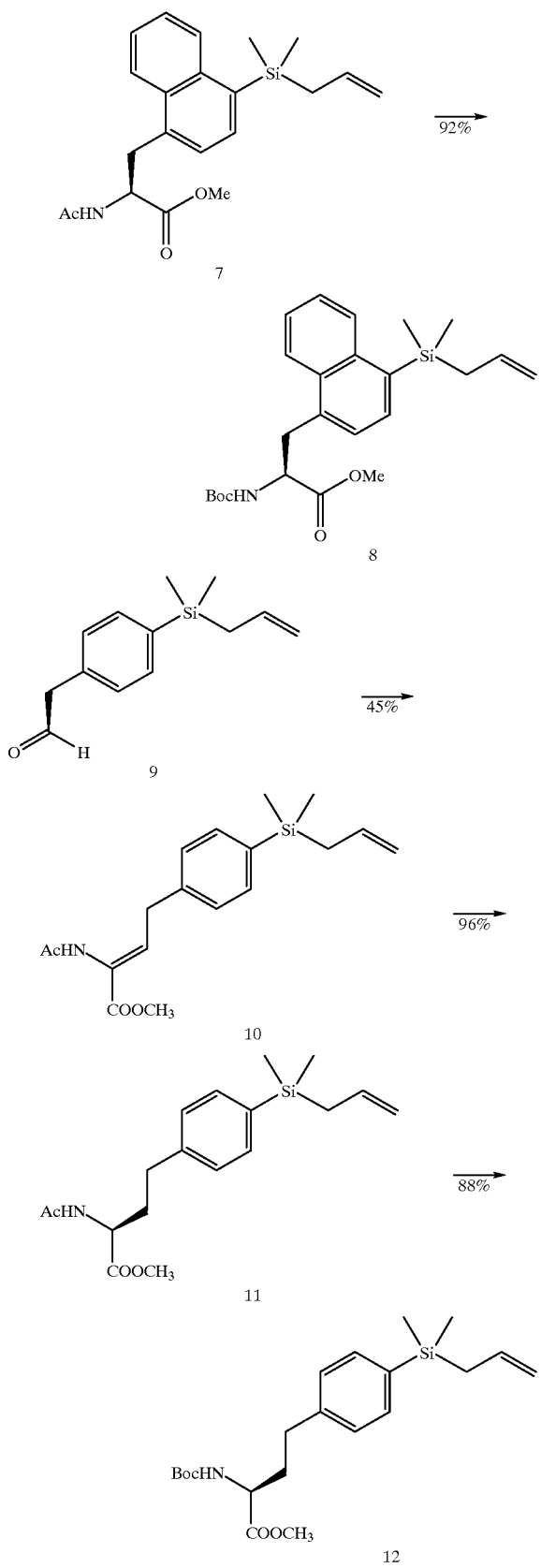

As shown in Scheme 6, the same reaction sequence illustrated in Scheme 5 can be applied to other arylsilyl-derived aldehydes to generate chiral amino acids with various silylated aromatic side chain.

Thus, 2-allyldimethylsilylthiophene-5-carboxaldehyde (1 Scheme 6), 1-allyldimethylsilyl-4-naphthaldehyde (5 Scheme 6), and 4-allyldimethylsilylphenylacetaldehyde (9 Scheme 6) underwent the following sequential reactions; Horner-Emmons olefmation, asymmetric catalytic hydrogenation reaction, and one-pot conversion of acetyl group to Boc protecting group, to give silylated-thienylalanine (4 Scheme 6), naphthylalanine (8 Scheme 6), and phenethylglycine analogue (12 Scheme 6), respectively. Hydroboration and Suzuki coupling reaction of these compound then yields corresponding products.

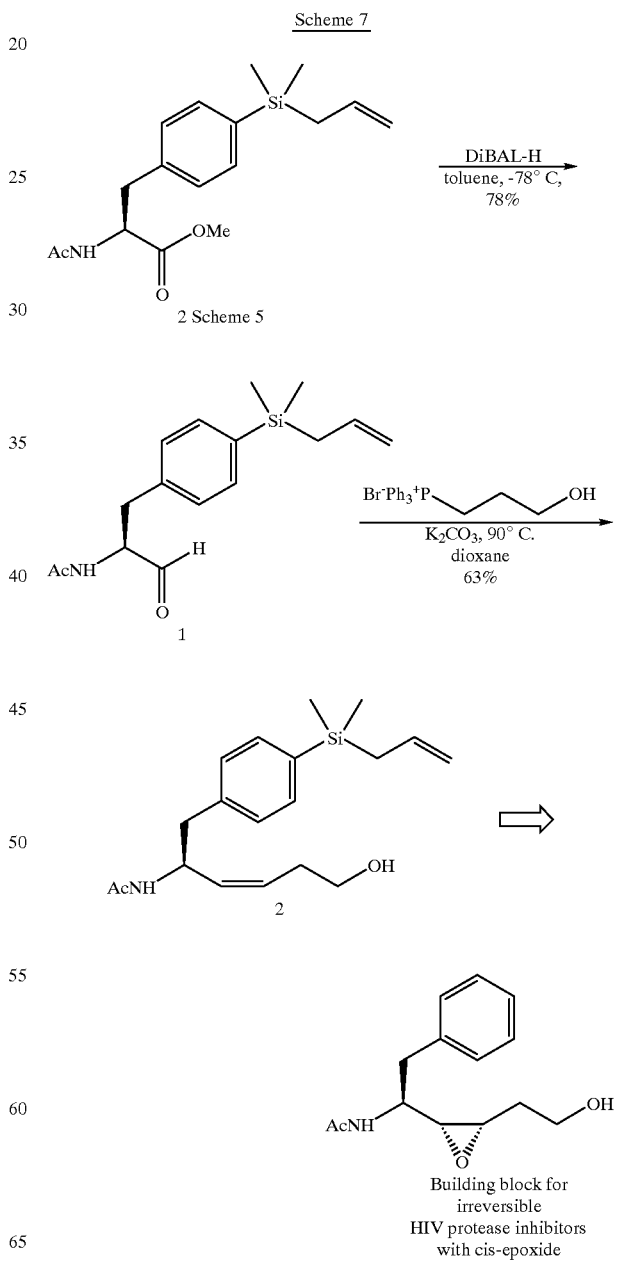

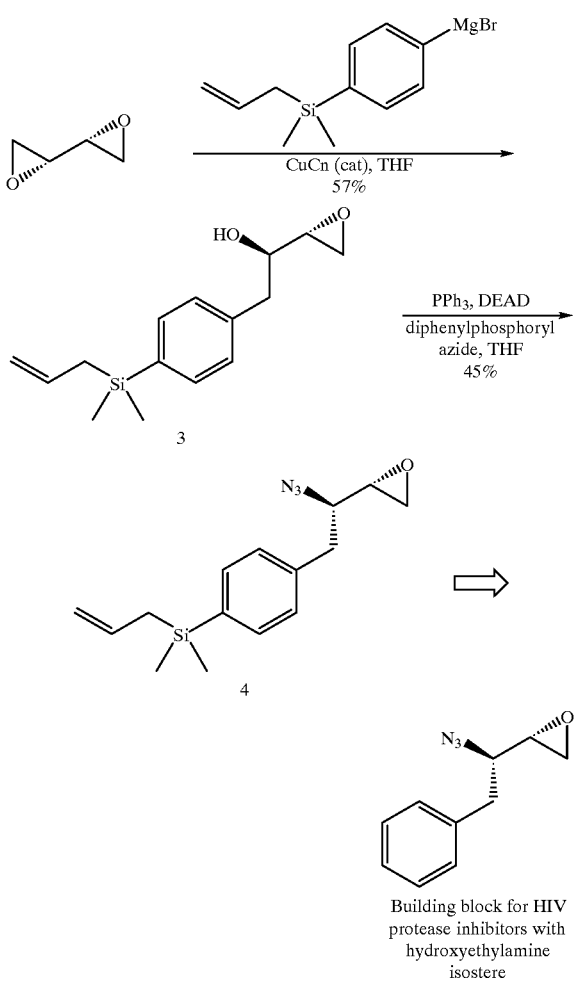

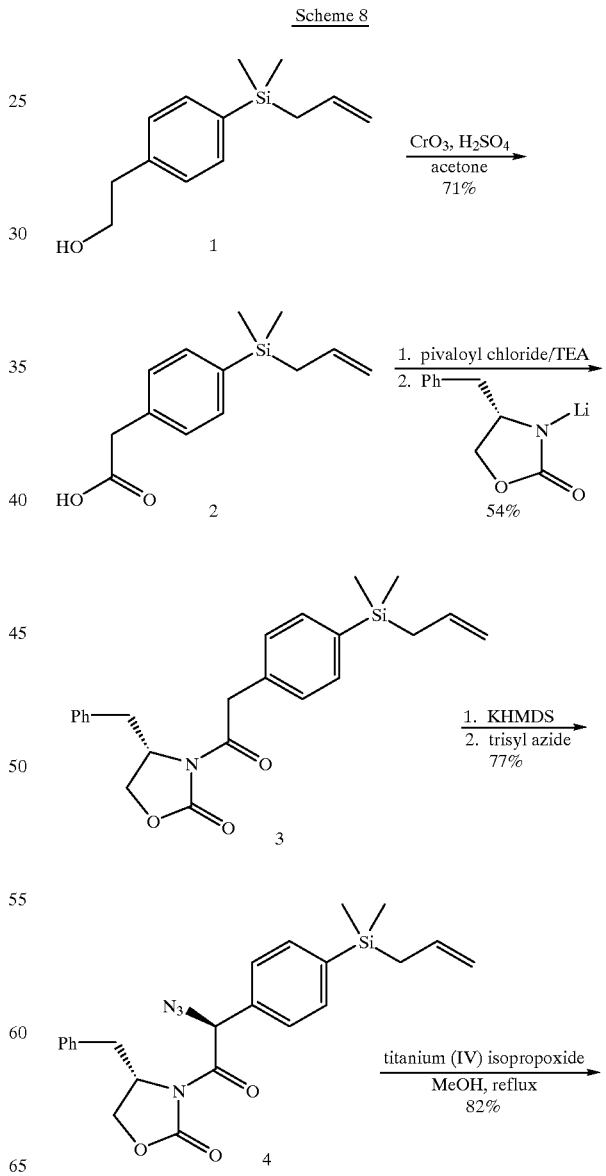

Scheme 8

Building block for HIV protease inhibitors with hydroxyethylamine isostere

HIV protease inhibitors, along with reverse transcriptase inhibitor drugs, are important components of a cocktail used for treating patients with AIDS. Inhibitors of HIV protease can be accessed by the incorporation of an isostere that mimics the geometry of the tetrahedral intermediate in place of the scissile bond of the peptide substrate. Many potent inhibitors have been developed using this principle. One of the structures identified effective for inhibition of HIV protease is the hydroxyethylamine isostere where a secondary alcohol mimics a stable tetrahedral intermediate in the region spanning $P_1$–$P_1'$. In fact, several approved HIV protease drugs on the market and drug candidates are based on the hydroxyethylamine isostere as a key pharmacophore. A different type of HIV protease inhibitors containing cis-epoxide are also known. One of the structural features the known HIV protease inhibitors share in common is that the key pharmacophore is derived from phenylalanine (or phenylalanine analogs), indicating that the bulky hydrophobic residue in these inhibitors may be important for their biological activities. The present invention provides compounds which can be used for solid-phase synthesis of HIV protease inhibitors and method for preparing the same. Compounds of the present invention can also be adapted as tools for synthesis of other aspartyl protease inhibitors.

Two silylated intermediates (2 Scheme 7 and 4 Scheme 7) which are well-known precursors of HIV protease inhibitors were prepared as shown in Scheme 7. Reduction of N-acetyl amino ester (2 Scheme 5) gave an aldehyde (1 Scheme 7) which underwent Wittig olefination reaction to produce a disubstituted cis-double bond (2 Scheme 7). Once this compound was attached to the polymer via the coupling reaction as described in Scheme 2, the polymer bound building block could be used for rapid synthesis of irreversible HIV protease inhibitors containing phenylalanine-derived cis-epoxide.

Butadiene diepoxide react with Grignard reagent at the less hindered carbon. Azidation of the resulting alcohol (3 Scheme 7) under Mitsunobu conditions provided the desired azido oxirane derivative (4 Scheme 7). After an appropriate modification of azide function followed by coupling to the polymer, the resin-bound compound can be used for parallel (or combinatorial) synthesis of aspartyl protease inhibitors.

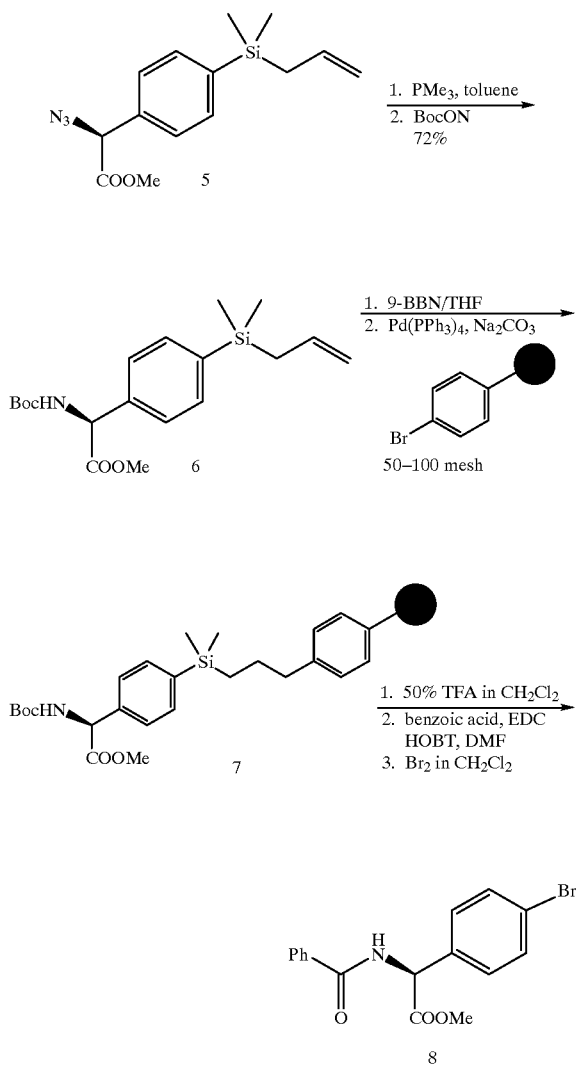

Phenylglycine is an important component of many natural products. One of the phenylglycine containing cyclic peptides of biological significance is the family of pristinamycin I. Pristinamycin I, along with its other synergistic component pristinamycin II, is used for the treatment of infection. Pristinamycin I is a mixture of three peptidic macrolactones: pristinamycin $I_A$, $I_B$, and $I_C$, which differ by one methyl group. It is composed of six amino acid residues which are connected with five amide bonds and one ester bond. The amino group of the threonine residue is acylated with 3-hydroxy picolinic acid. The successful synthetic approaches of pristinamycin I involves construction of a linear ring-opened depsipeptide and subsequent ring closure by formation of an amide ring.

Due to the limitation of currently available linkers for solid phase synthesis, cyclic compounds such as pristinamycin I, which do not have any polar side chains, are not suitable for a head-to-tail cyclization strategy on a solid support. Compounds of the present invention include resin-bound phenylglycine derivatives which can be used for solid-phase synthesis of Pristinamycin I as well as other phanylglycine-containing cyclic compounds.

Preparation of phenylglycine derivative with a silyl group attached to the phenyl ring is shown in Scheme 8. 4-allyldimethylsilylphenethyl alcohol (1 Scheme 8) was oxidized to produce 4-allyldimethylphenylacetic acid (2 Scheme 8). This acid was activated with pivaloyl chloride and treated with a lithiated chiral oxazolidinone to obtain an imidate (3 Scheme 8). Evans asymmetric azidation reaction gave azido imidate (4 Scheme 8). Treating the purified isomer (4 Scheme 8) with titanium mediated esterification reaction gave a methyl ester (5 Scheme 8) which was treated with trimethylphosphine followed by BocON in one pot to obtain Boc-protected phenylglycine methyl ester (6 Scheme 8). This was attached to the polymer by hydroboration and Suzuki coupling reaction to generate polymer-bound phenylglycine derivative (7 Scheme 8). Deprotection of Boc group and acylation of the resulting amine with benzoic acid, then subsequent cleavage with bromine released bromo-substituted analog (8 Scheme 8). The polymer-bound phenylglycine derivative (7 Scheme 8) can be used for solid-phase synthesis of pristinamycin I and other phenylglycine-containing peptides of biological importance.

Scheme 9

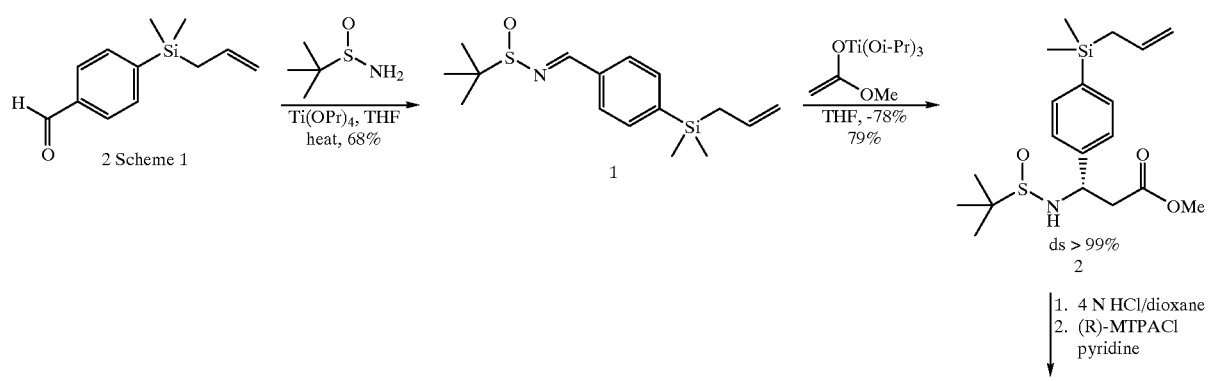

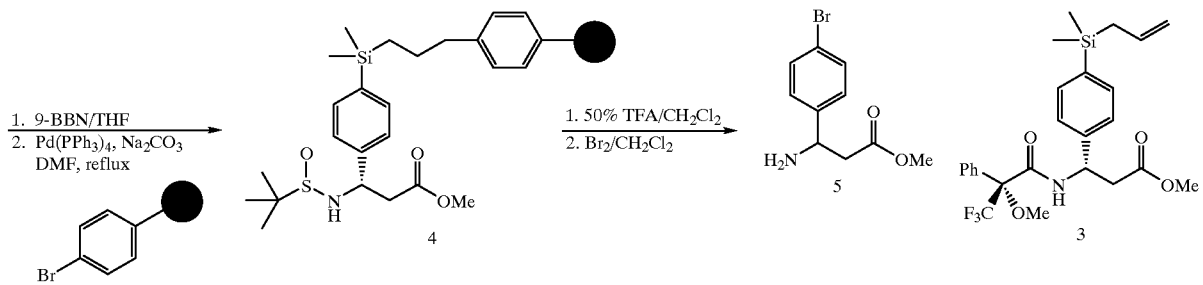

If the libraries of target molecules require aromatic side chain not the amino acid back bone as an essential element for favorable interactions with biological entity of interest, the α-amino acid can be replaced with other type of multi-functional unit, such as β-amino acids. Therefore, new amino acid building blocks can be designed to generate libraries of compounds containing an aryl side chain. As an example, cyclo β-tetrapeptide prepared as somatostatine analog by others was found to display a significant biological activity and affinity for human receptors. In fact, various β-amino acid compounds may be used for the design of therapeutic agents with improved oral bioavailability.

Moreover, β-amino acids are important components of numerous natural products and therapeutic agents. Because of the enzymatic stability of β-peptides in the biological systems, β-amino acids have become useful building blocks for the design of new peptidomimetics. Consequently, there has been growing demand for β-amino acids. Although several known methods, for example, Arndt-Eistert homologation of α-amino acids and catalytic hydrogenation of 3-amino acrylate, are widely used for the preparation of β-amino acids, and a number of β-amino acids are commercially available, it is highly desirable to develop a new methodology for polymer bound β-amino acids building block as a tool for rapid synthesis and high diversification of compounds.

The synthetic procedure for the preparation of β-amino acid attached to the polymer through its side chain is outlined in Scheme 9. Condensation of 4-allyldimethylsilylbenzaldehyde (2 Scheme 1) with (R)-(−)-tert-butanesulfinamide in the presence of titanium proxpoxide gave tert-butanesulfinyl imine (1 Scheme 9).

The titanium enolate generated by transmetalation of lithiated methyl acetate with TiCl(O-i-Pr)$_3$ was reacted with imine (1 Scheme 9) to provide a sulfinylated β-amino ester (2 Scheme 9). The diastereoselectivity of β-amino ester (2 Scheme 9) was determined by the analysis of the Mosher amide (3 Scheme 9), prepared by deprotection of the tert-butanesulfinyl group followed by subsequent derivatization of amino group with (R)-(−)-α-methoxy-α-(trifluoromethyl)-phenylacetic acid chloride (MTPACl). Analysis of both $^1$H NMR and $^{19}$F NMR spectra of Mosher amide (3 Scheme 9) showed less than 1% of the minor diastereomer. Hydroboration of the terminal olefin of β-amino ester (2 Scheme 9) followed by in situ Suzuki coupling with bromopolystyrene resin resulted in polymer-bound β-amino acid derivative (4 Scheme 9). The loading level (0.32 mequiv/g) of resin (4 Scheme 9) can be determined by mass balance of (3R)-methyl 3-amino-3-(4-bromophenyl)-butyrate (5 Scheme 9) which can be obtained by stirring an aliquot of resin (4 Scheme 9) with 50% TFA in CH$_2$Cl$_2$ for 5 min followed by washing and cleavage reaction (Br$_2$, CH$_2$Cl$_2$, 20 min).

Scheme 10

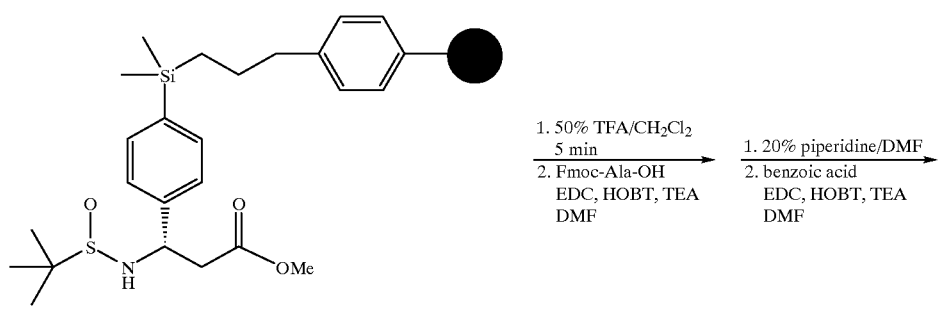

4 Scheme 9

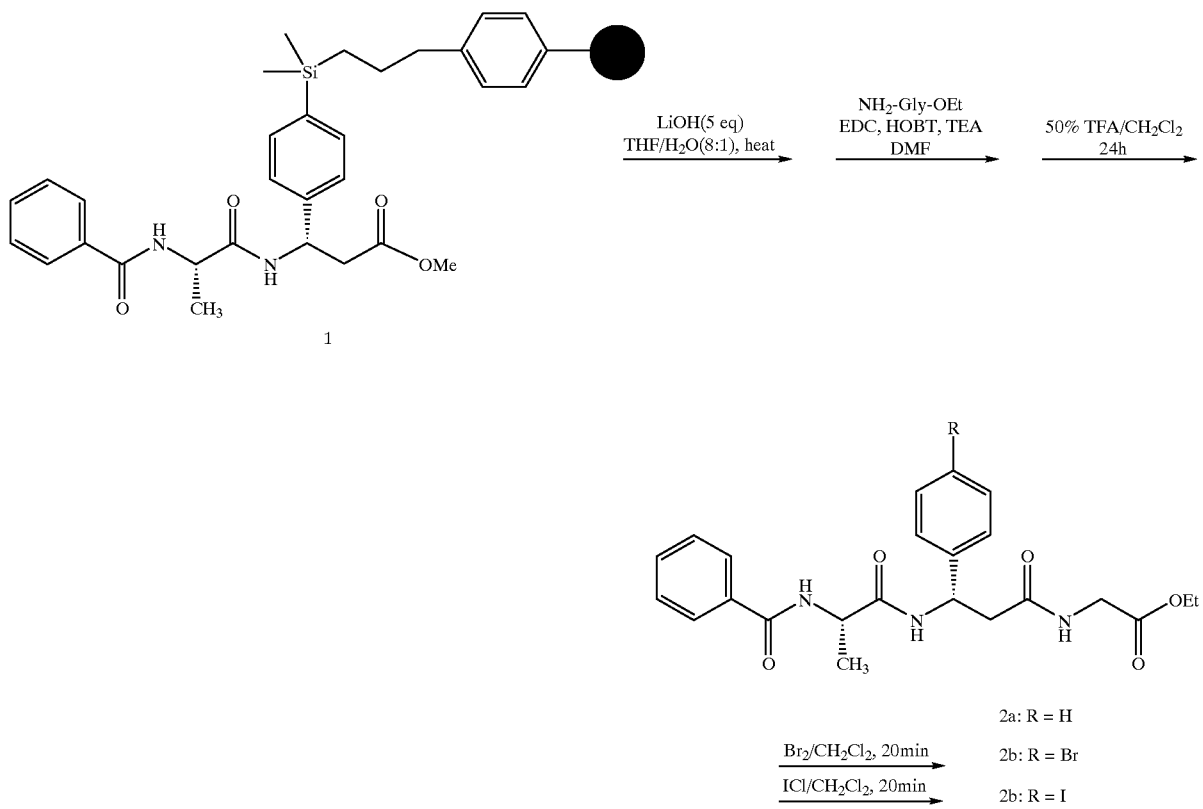

Scheme 10 illustrates the suitability of compounds of the present invention (4 Scheme 9) in a wide variety of solid-phase organic synthesis, including synthesis of tripeptides (2 Scheme 10). The resin-bound compound (4 Scheme 9) was treated with 50% TFA to remove tert-butanesulfinyl group. The resulting amino group was reacted with Fmoc-Ala-OH using standard EDC and HOBt coupling conditions in DMF, then Fmoc group was deprotected with 20% piperidine in DMF. After several washings of the resin, benzoic acid was coupled to the amine to yield polymer-bound dipeptide analog (1 Scheme 10). Hydrolysis of the ester group at the C-terminus of resin (1 Scheme 10) with LiOH(5 eq.) in THF/H$_2$O (8:1) under refluxing condition for 2.5 h, coupling with Gly-OEt, and cleavage of the product with TFA gave tripeptide (2a Scheme 10).

Alternatively, cleavage of the tripeptide from the resin by ipso-substitution of the silyl group with Br$_2$ gave bromo-substituted tripeptide (2b Scheme 10). Likewise, cleavage of the tripeptide with ICl gave iodo-substituted tripeptide (2c Scheme 10).

Because non-polar aromatic rings play important roles as a pharmacophore in bioactive molecules, compounds of the present invention may be used for the design of focused library containing β-amino acid with a non-polar aryl side chain.

Scheme 11

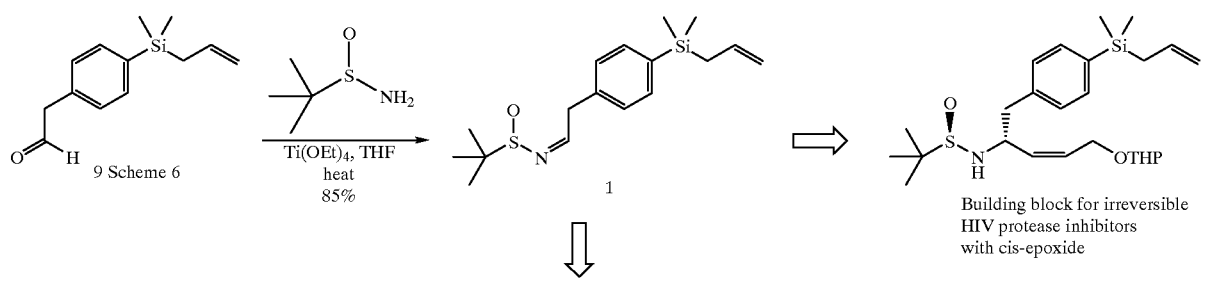

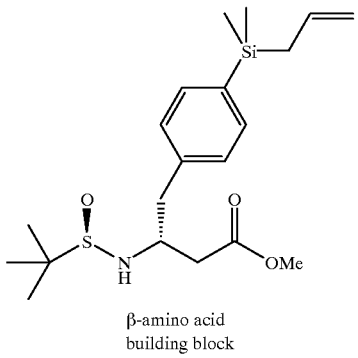

β-amino acid
building block

A similar approach as illustrated in Scheme 9 was employed to prepare a silylated compound (1 Scheme 11) which can be used for the synthesis of other biologically active compounds. 4-allyldimethylsilylphenylacetaldehyde (9 Scheme 6) was condensed with (R)-(−)-tert-butanesulfinamide to give tert-butanesulfinyl imine (1 Scheme 11). Reaction of the resulting compound with appropriate Grignard reagents provides important intermediates which are useful for a synthesis of irreversible HIV protease inhibitors.

By following the same reaction sequence as described in Scheme 9, the imine (1 Scheme 11) can also be converted to a β-amino acid compound which can be linked (i.e., attached) to a solid support.

Scheme 12

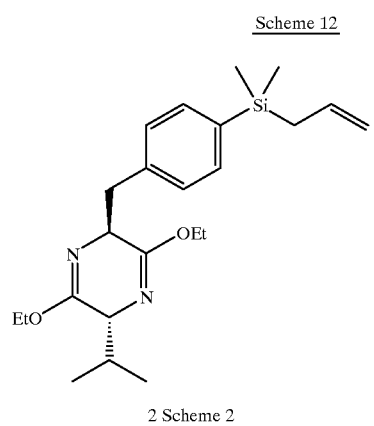

2 Scheme 2

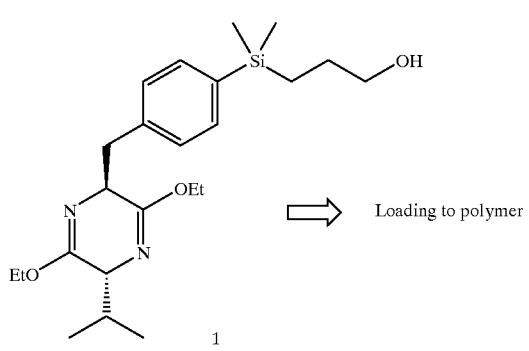

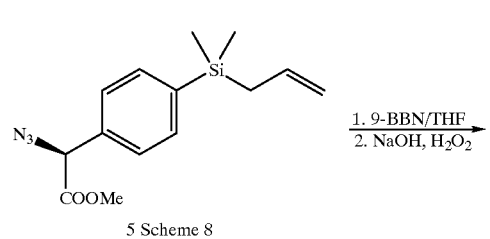

5 Scheme 8

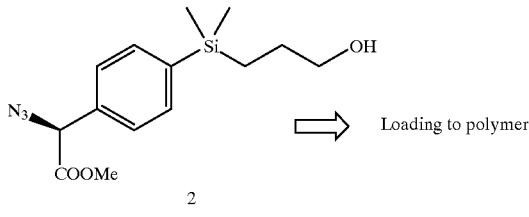

Hydroboration of the double bond and subsequent Suzuki coupling of the resulting organoborane to the bromopolystyrene was utilized as a preferred method to attach the compounds of the present invention to a solid support. Because organoboranes can be efficiently replaced by hydroxyl, halogen, or amino groups by well established chemistry, other polystyrene resins may be used to attach properly functionalized compounds of the present invention. As illustrated in Scheme 12, treatment of silylated bislactim ether (2 Scheme 2) with 9-BBN followed by alkaline hydrogen peroxide gave a primary alcohol (1 Scheme 12). In the similar manner, silylated phenylglycine precursor (5 Scheme 8) can be converted to the corresponding alcohol derivative (2 Scheme 12). Appropriate reactions for linking these alcohol functionalized compounds to a variety of polymer resins (e.g., Merrifield, Wang, and hydroxymethyl polystyrene resins) are well known to one of ordinary skill in the art.

Scheme 13

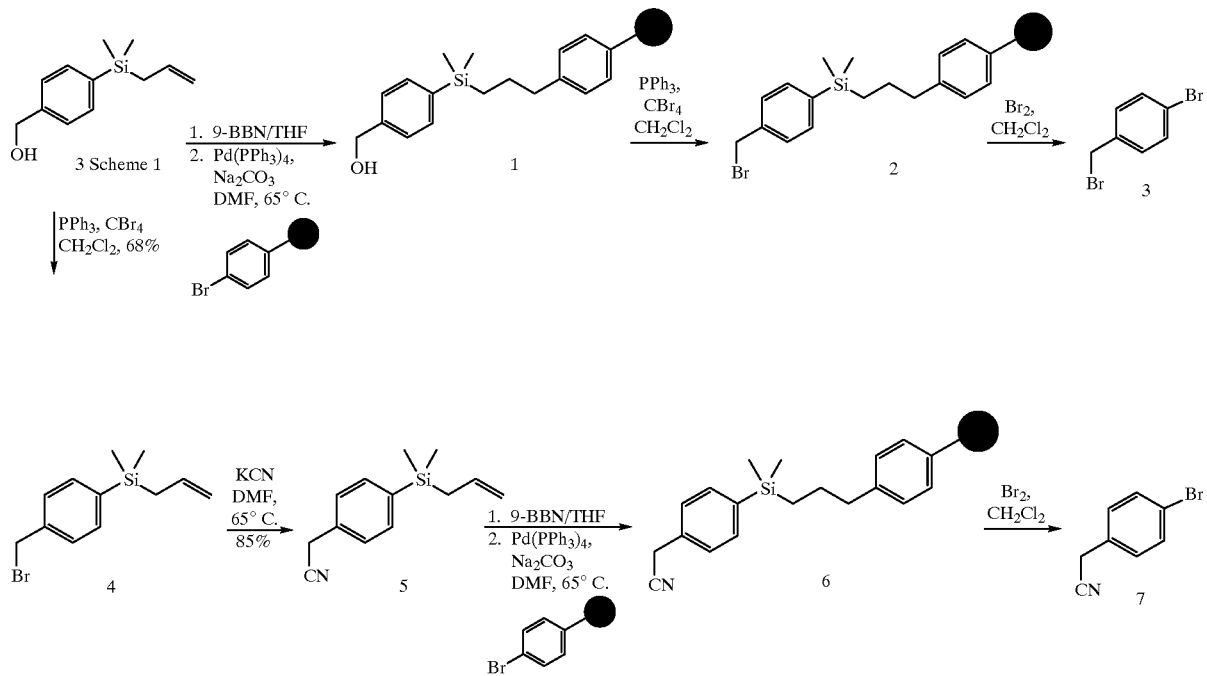

Preparation of other useful organic compounds using the processes of the present invention is illustrated in Scheme 13. For example, 4-allyldimethylsilylbenzyl alcohol (3 Scheme 1) was attached to the bromopolystyrene resin by two step sequences. Hydroboration of the allylsilane with 9-BBN followed by in situ Suzuki coupling with bromopolystyrene provided a polymer-bound benzylalcohol (1 Scheme 13). Polymer-bound benzyl bromide (2 Scheme 13) was readily prepared from polymer-bound benzyl alcohol (1 Scheme 13). Treatment of polymer-bound benzyl bromide (2 Scheme 13) with $Br_2$ gave 4-bromobenzyl bromide. The loading level of resin (2 Scheme 13, 0.37 mequiv/g) was determined by mass balance of the obtained 4-bromobenzyl bromide. As will be obvious in the following examples, these two polymer-bound compounds (1 Scheme 13, and 2 Scheme 13) can be used for immobilization of appropriate carboxylic acids, amines, and alcohols.

Reaction of 4-allyldimethylsilylbenzyl alcohol (3 Scheme 1) with triphenylphosphine and carbon tetrabromide gave 4-allyldimethylsilylbenzyl bromide (4 Scheme 13). Subsequent reaction with potassium cyanide gave 4-allyldimethylsilylphenylacetonitrile (6 Scheme 13). Under the usual coupling conditions, this was loaded to the polymer and the loading level of resin (2 Scheme 13, 0.23 mequiv/g) was determined by the mass balance of 4-bromophenylacetonitrile which was obtained from cleavage reaction of the resin with bromine.

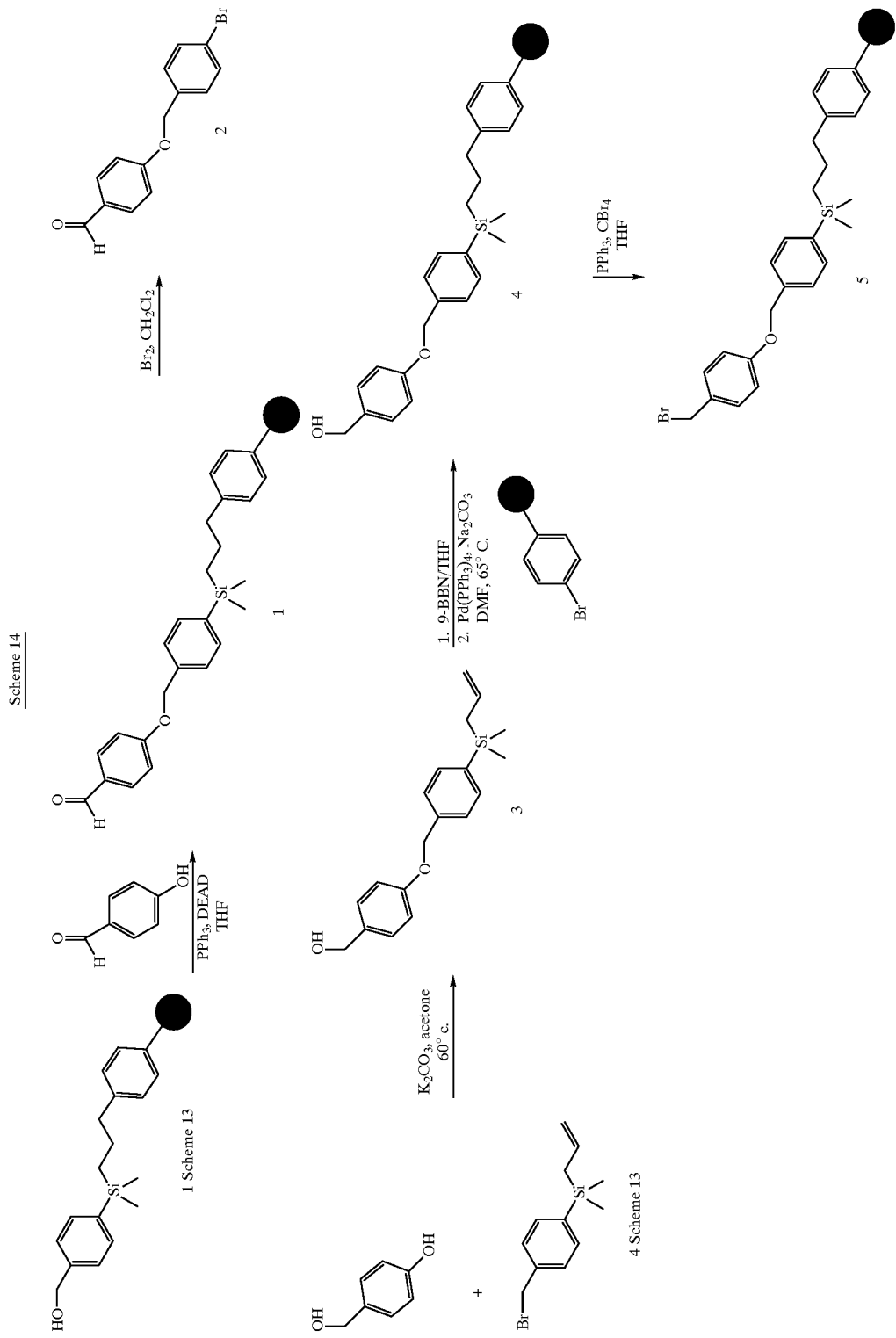

Polymer support functionalized with hydroxyl group, such as Wang and hydroxymethyl polystyrene, can be used for the immobilization (i.e., linking) of alcohols, carboxylic acids, and amines. Scheme 14 shows modification (i.e., chemical transformation) of polymer-bound alcohol (1 Scheme 13) to provide new polymer-bound compounds. Etherification of 4-hydroxybenzaldehyde with polymer-bound benzyl alcohol (1 Scheme 13) under Mitsunobu condition gave polymer-bound benzyloxybenzaldehyde (1 Scheme 14) which was identified by isolation of 4-(4-bromobenzyloxy)benzaldehyde (2 Scheme 14).

Selective alkylation of 4-hydroxybenzyl alcohol with 4-allyldimethylsilylbenzyl bromide (4 Scheme 13) gave 4-(4-allyldimethylsilylbenzyloxy)benzyl alcohol (3 Scheme 14) which was linked to bromopolystyrene to provide polymer-bound benzyloxybenzyl alcohol (4 Scheme 14). Functional group transformation of alcohol to bromide on the polymer support gave polymer-bound benzyloxybenzyl bromide (5 Scheme 14).

and C-termini of the dipeptide (1 Scheme 15) are derivatized with non-polar aromatic groups, solid-phase synthesis and combinatorial approach of these analogs using conventional solid support is difficult.

A reasonable retrosynthetic analysis for solution reaction dissects this molecule (1 Scheme 15) to three parts, Cbz-protected histidine (2 Scheme 15), secondary amino ester (3 Scheme 15), and a primary amine (4 Scheme 15). The secondary amino ester can be further dissected to 4-(benzyloxy)benzaldehyde (5 Scheme 15) and glycine ethyl ester. Standard peptide coupling reactions could put them together to give the dipeptide (1 Scheme 15) derivatized with non-polar aromatic rings. It was found that the polymer-bound compounds (1 Scheme 14 and 5 Scheme 14) prepared in Scheme 14 can be used for a solid-phase synthesis of this molecule. Polymer-bound benzyloxybenzylbromide (5 Scheme 14) reacts with glycine ethyl ester to produce a secondary amino ester (6 Scheme 15).

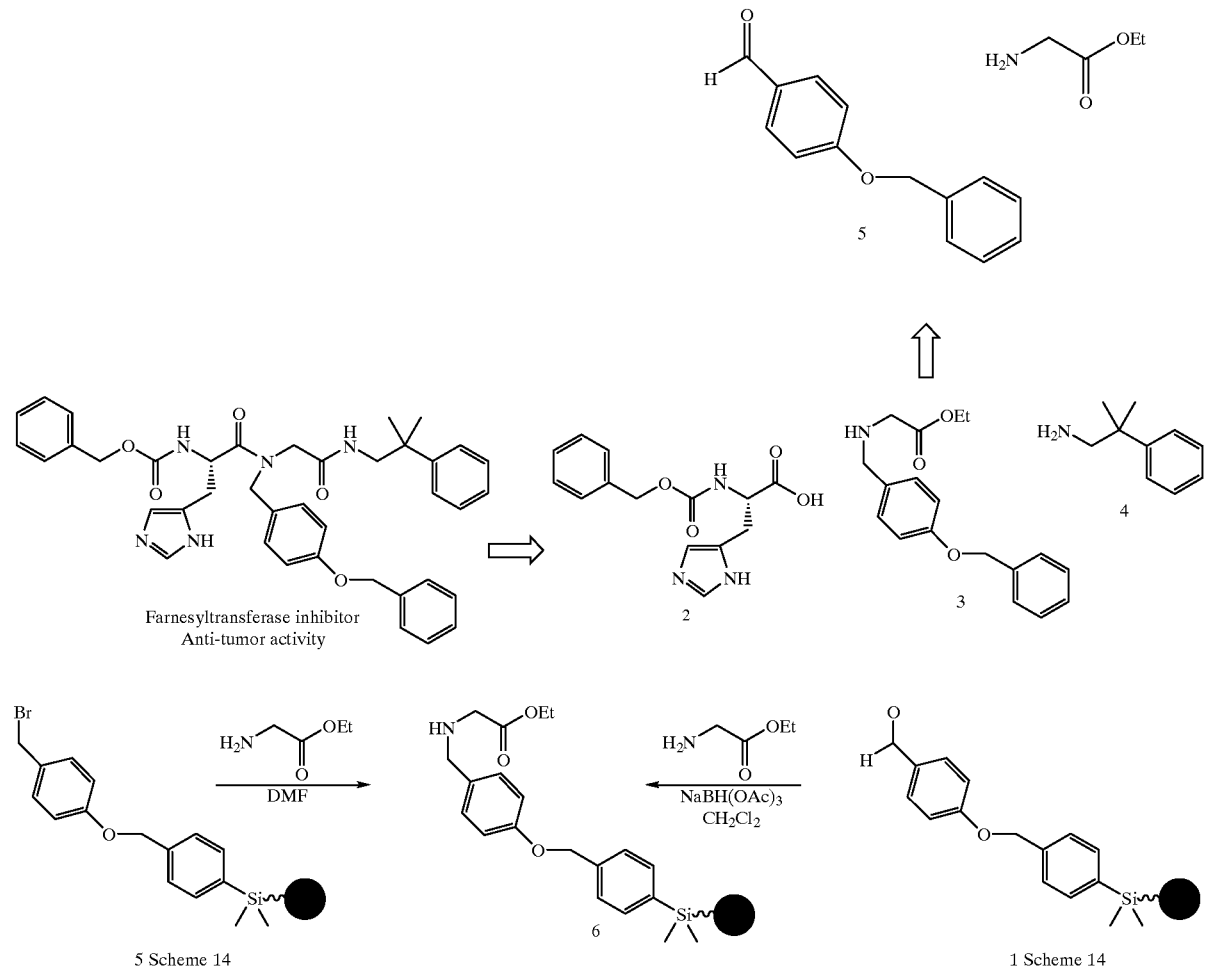

Scheme 15

Numerous pharmaceutical agents are derivatized with non-polar aryl moieties, which limit solid-phase synthesis approach using conventional solid-support synthesis. For example, the N-substituted dipeptide analog (1 Scheme 15) was found to have anti-tumor activity. Because both of N-

Alternatively, reductive amination of polymer-bound benzyloxybenzaldehyde (1 Scheme 14) with glycine ethyl ester can provide the same polymer-bound secondary amino ester which can be subjected to a peptide coupling as described above for solution reactions.

Scheme 16

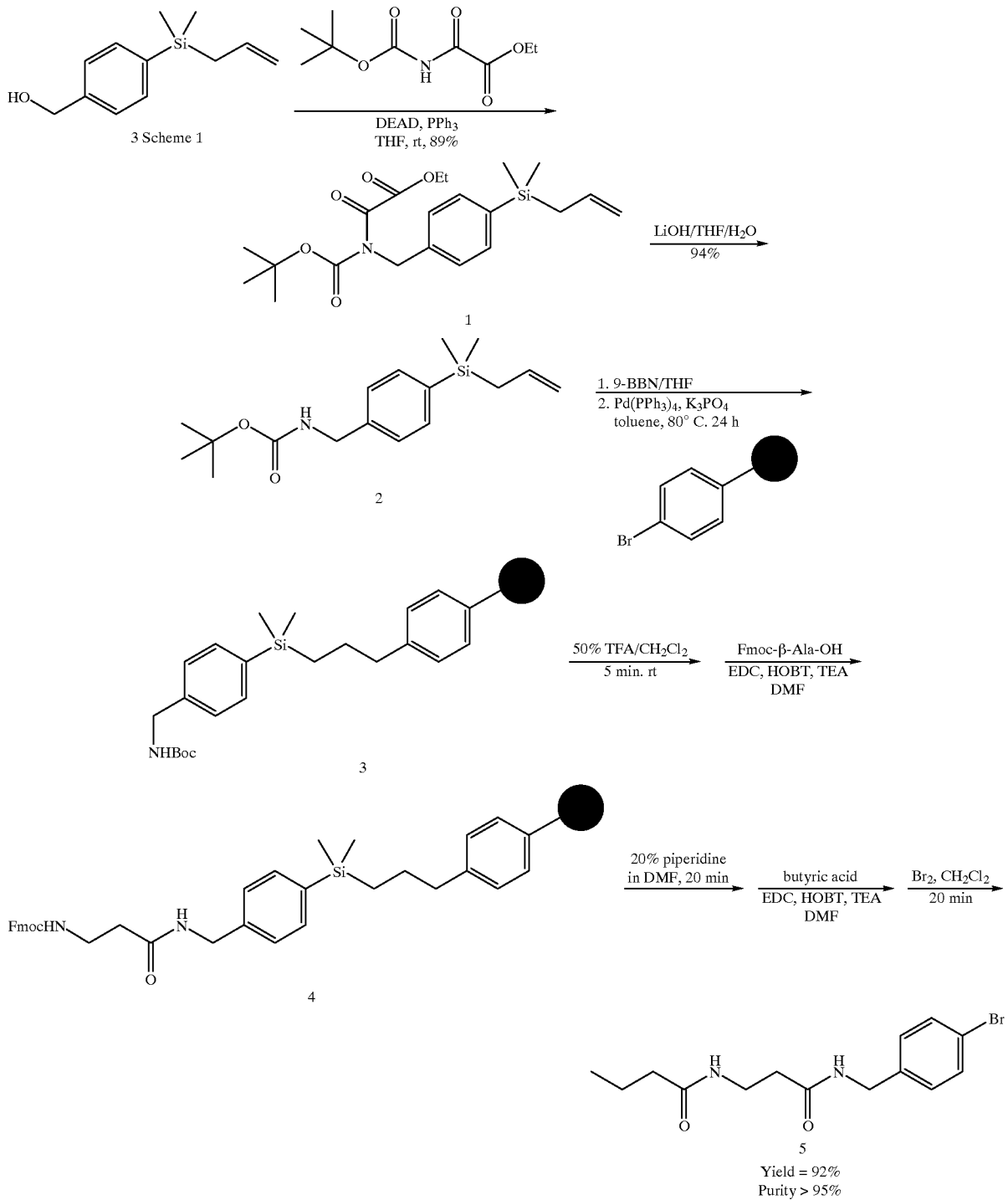

Scheme 16 illustrates compounds and methods of the present invention which allow retaining a benzyl functional group after cleavage from the solid-support. Various carboxylic acids (or amino acids) can be attached to the resin-bound compound (3 Scheme 16) under the typical amide coupling conditions to yield a resin-bound amide (4 Scheme 16) and later cleaved from the solid-support to give a compound with a benzyl moiety which has a non-polar functionality such as H, Br, or I on the phenyl ring. Carboxylic acids with other functional group can be subjected to a variety of other chemicals reaction to modify the functional group. For example, malonic acid derivatives bound to the benzylamine linker can be subjected to a Knoevenagel reaction to generate 1,3-carbonyl derivatives. Imines formed from condensation reaction with aldehydes can be treated with Grignard reagents (alkyl- or aryllithium)

to give various α-branched secondary amines or used for the synthesis of β-lactams via [2+2] Staudinger reaction on solid support. In situ reduction [NaBH(OAc)$_3$, CH$_2$Cl$_2$] of the imines yields polymer-bound secondary amines which can be further derivatized, e.g., to benzyl group-containing carboxamides or sulfonamides.

The polymer-bound silylated benzylamine (3 Scheme 16) can be prepared according to the procedure illustrated in Scheme 16. Mitsunobu reaction of 4-allyldimethylsilylbenzyl alcohol (3 Scheme 1) with N-Boc protected ethyl oxamate followed by hydrolysis afforded Boc-protected silylated benzylamine (2 Scheme 16). Hydroboration with 9-BBN followed by Suzuki coupling with bromopolystyrene provided polymer-bound N-Boc protected benzylamine (3 Scheme 16).

Standard peptide coupling reaction using this polymer-bound benzylamine (3 Scheme 16), with either Boc or Fmoc protecting group, and appropriate carboxylic acids gave benzylamine-containing dipeptide analog (5 Scheme 16).

(2 Scheme 13) was reacted phenethylamine followed by cleavage of the solid-support to obtain the desired secondary amine (2 Scheme 17).

In solution chemistry, reaction of alkyl halides with primary amines results in a mixture of mono- and dialkylated products. However, reaction of excess primary amine with resin-bound alkylating agent provided only a secondary amine (1 Scheme 17). The resin-bound secondary amine (1 Scheme 17) was further reacted with p-toluenesulfonyl chloride to give sulfonamide (3 Scheme 17) after cleavage reaction.

Treatment of the polymer-bound benzylbromide (2 Scheme 13) with Gly-OEt, followed by sulfonamide formation with p-toluenesulfonyl chloride, hydrolysis of intermediate ester under the alkaline conditions, treatment with O-ethyl hydroxylamine under the coupling conditions, and cleavage from the solid-support with bromine gave a hydroxamic acid analog (4 Scheme 17). This class of hydroxamic acid analogs is a known inhibitor of matrix Scheme 17

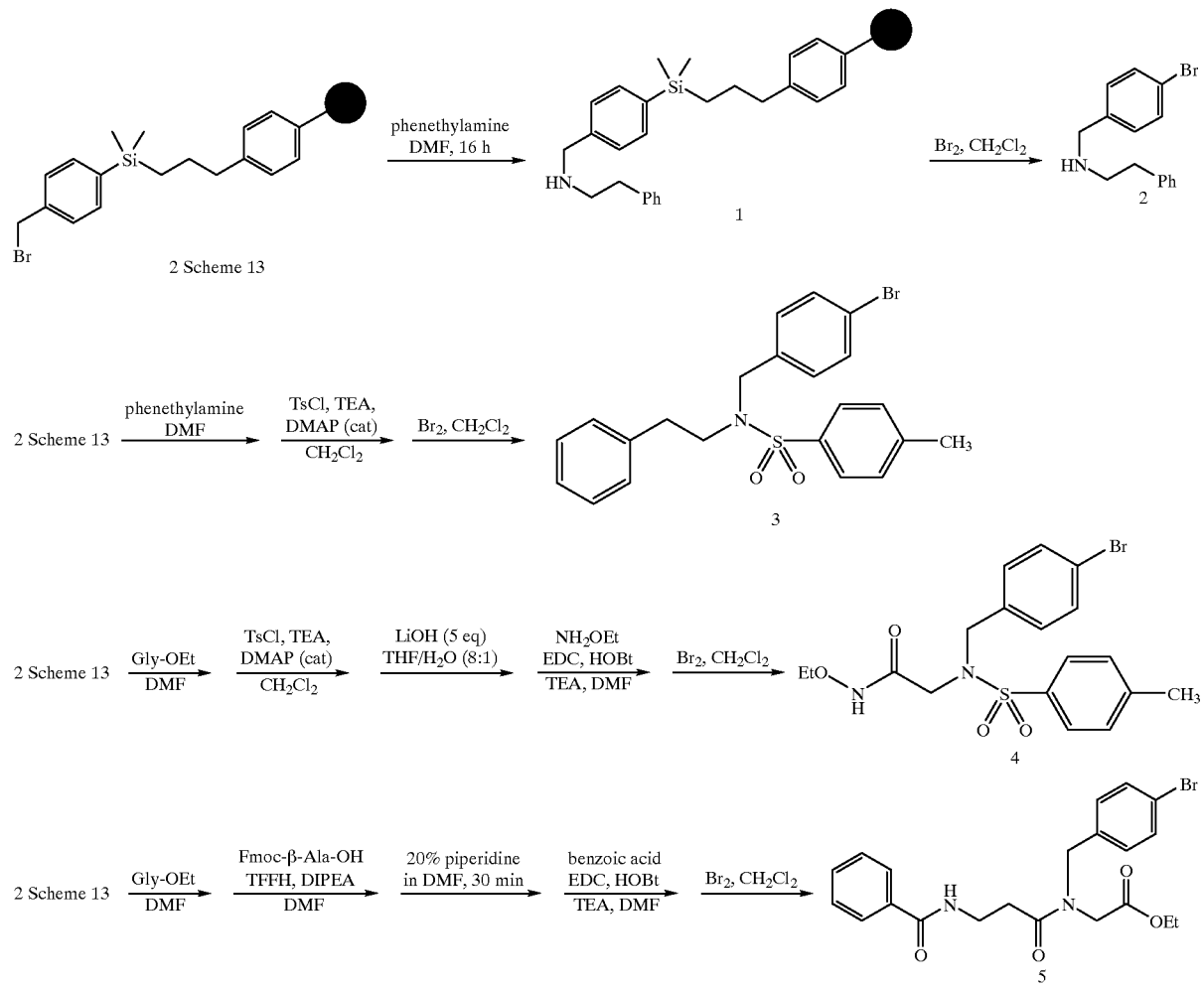

The applications of the polymer-bound benzylbromide (2 Scheme 13) for solid-phase synthesis of small organic molecules are illustrated in Scheme 17. In order to synthesize a secondary amine, the polymer-bound benzylbromide metalloproteinase (MMP) which have become important pharmacological targets for treatment of many diseases.

Instead of sulfonylation of the secondary amine intermediate, peptide coupling with amino acid gave N-benzylated peptidomimetics. Efficient synthesis of this type of compounds is important for the design of peptide analogs with favorable in vivo activity. Thus, a peptidomimetic with increased hydrophobic nature, N-benzylated peptide analog (5 Scheme 17) was synthesized using the polymer-bound benzylbromide (2 Scheme 13). The secondary amine intermediate formed from the reaction with the polymer-bound benzylbromide (2 Scheme 13) and glycine ethyl ester was coupled with Fmoc protected β-alanine acid fluoride. Deprotection of Fmoc group by treatment of the resin with 20% piperidine afforded a free amine which was acylated by the subsequent coupling reaction with benzoic acid. Cleavage reaction with bromine yielded the desired peptide analog (5 Scheme 17).

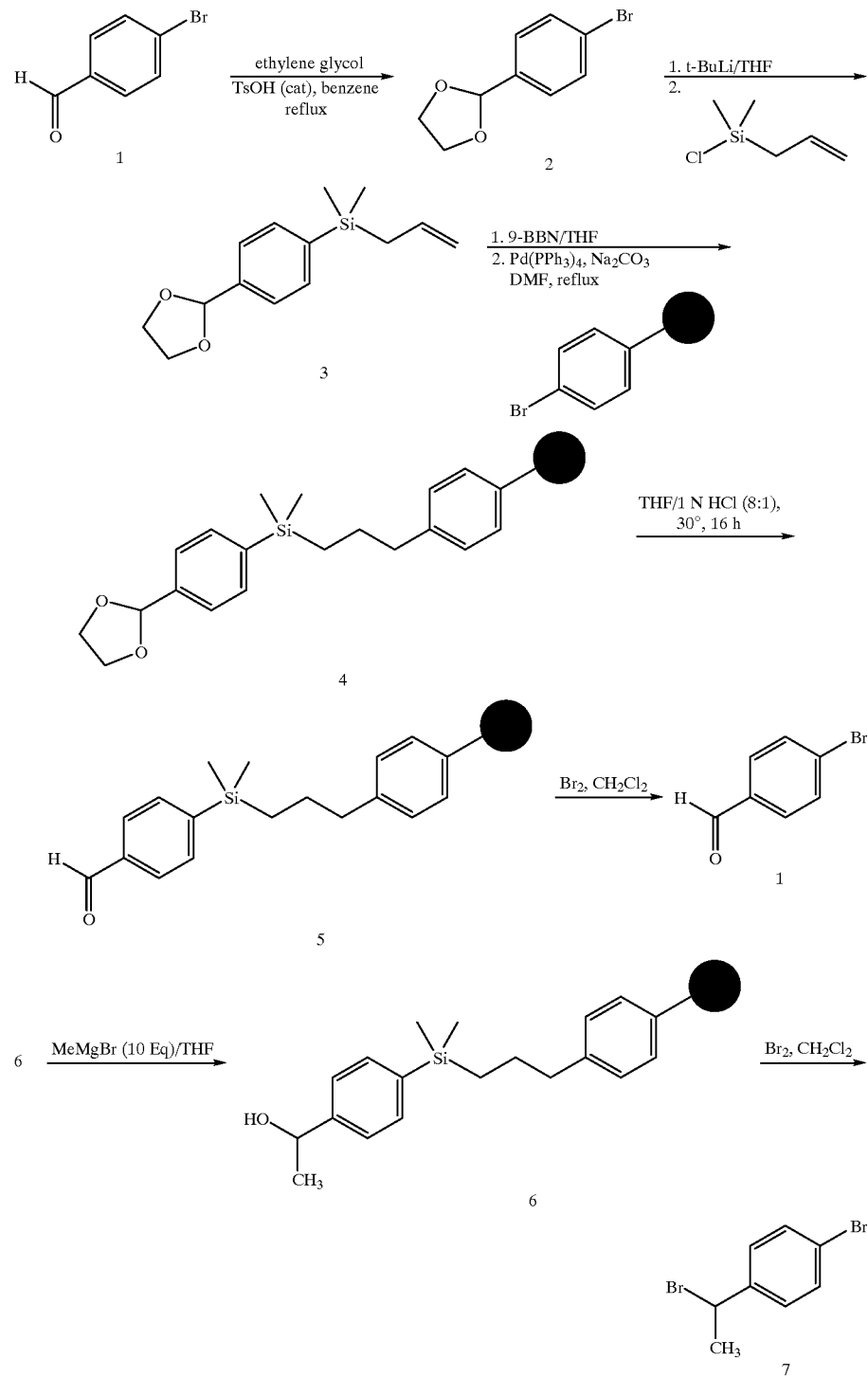

The synthetic procedure for preparation of polymer-bound benzaldehyde (5 Scheme 18) is illustrated in Scheme 18. 4-Bomobenzaldehyde (1 Scheme 18) was protected to 1,3-dioxolane derivative (2 Scheme 18). Lithium-halogen exchange of (2 Scheme 18) with t-butyllithium followed by addition of allydimethylsilyl chloride gave 2-(4-allyldimethylsilylphenyl)-1,3-dioxolane (3 Scheme 18). Hydroboration of (3 Scheme 18) with 9-BBN followed by Suzuki coupling with bromopolystyrene provided a precursor of polymer-bound benzaldehyde (4 Scheme 18). Hydrolysis gave the desired polymer-bound benzaldehyde (5 Scheme 18).

The utility of the polymer-bound benzaldehyde (5 Scheme 18) was demonstrated by the preparation of α-branched benzyl alcohol as shown in Scheme 18. Addition of methylmagnesium bromide to the polymer-bound benzaldehyde (5 Scheme 18) provided polymer-bound secondary alcohol (6 Scheme 18), which was cleaved with bromine to yield α-methyl-4-bromobenzyl bromide (7 Scheme 18). By choosing appropriate Grignard reagents, variety of secondary alcohols can be prepared. Such secondary alcohols can be further converted to other reactive species (for example bromide or tosylate) for solid-phase organic synthesis.

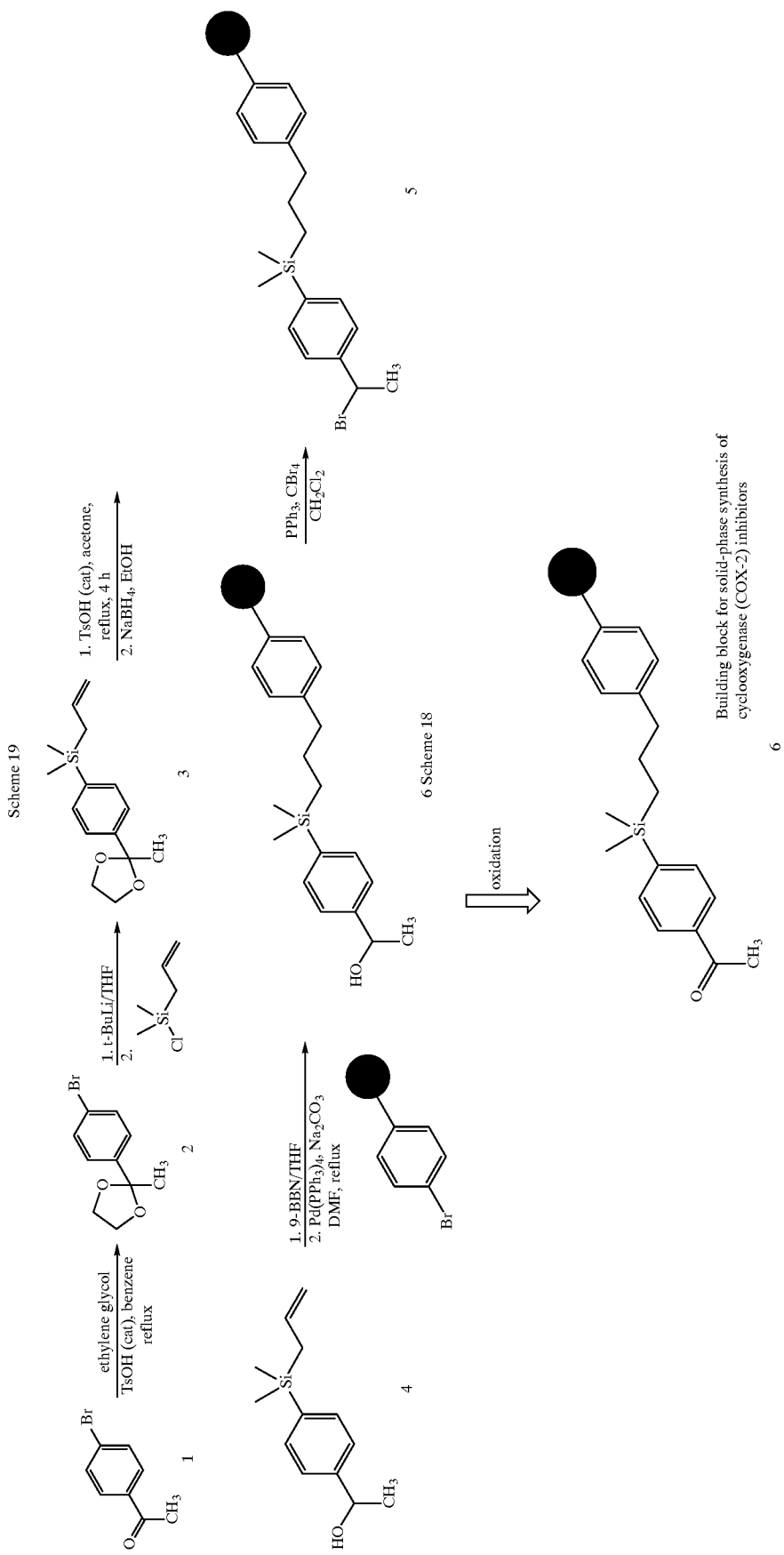

Alternative method for producing polymer-bound α-branched secondary alcohol (6 Scheme 18), in particular for a large-scale synthesis, is shown in Scheme 19. Starting from 4-bromoacetophenone and by following the similar reactions as described in Scheme 18, 2-( 4-allyldimethylsilylphenyl)-2-methyl-1,3-dioxolane (3 Scheme 19) was obtained. Deprotection of dioxolane protecting group and subsequent reduction of the resulting 4-allyldimethylsilylacetophenone afforded a secondary alcohol (4 Scheme 19). Hydroboration of the secondary alcohol (4 Scheme 19) with 9-BBN followed by in situ Suzuki coupling with bromopolystyrene provided the previously described polymer-bound α-branched secondary alcohol (6 Scheme 18). Conversion of the secondary alcohol to a bromine gave a polymer-bound α-methyl benzyl bromide (6 Scheme 18).

Recently, a series of sulfonamide-containing 1,5-diarylpyrazole derivatives have been reported to block the activity of cyclooxygenase (COX-2). Since COX-2 is expressed during inflammatory conditions, inhibitors of this enzyme can be used for the treatment of variety of ailments, including rheumatoid arthritis and osteoarthritis.

The polymer-bound α-branched secondary alcohol (6 Scheme 18) can be used to synthesize known COX-2 inhibitors on a solid support. For example, the polymer-bound α-branched secondary alcohol (6 Scheme 18) can be oxidized to acetophenone derivative which can undergo a Claisen condensation reaction with various esters to form 1,3-dicarbonyl adducts. Reaction with (4-sulfamoylphenyl)hydrazine and subsequent cleavage produces the same 1,5-diarylpyrazole COX-2 inhibitor derivatives on a polymer support.

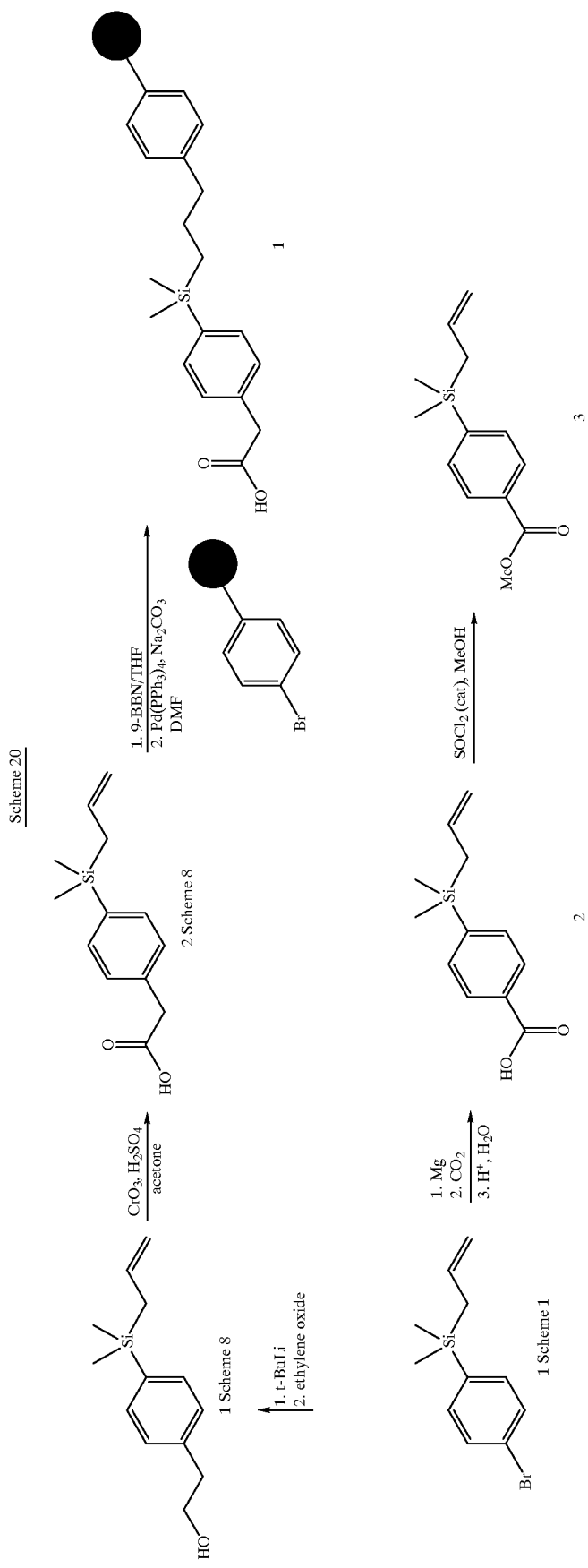

As shown in Scheme 20, 1-allyldimethylsilyl-4-bromobenzene (1 Scheme 1) was used as a starting material for the preparation of phenylacetic acid bound to the polystyrene via the silyl linkage (1 Scheme 20). Sequential treatment of 1-allyldimethylsilyl-4-bromobenzene with t-butyllithium in THF followed by addition of ethylene oxide solution in THF to the reaction mixture afforded two carbon homologated alcohol (1 Scheme 8). The primary alcohol was oxidized in a solution of Jones reagent ($CrO_3$, $H_2SO_4$) in acetone to give the carboxylic acid (2 Scheme 8). Hydroboration followed by Suzuki coupling of the carboxylic acid (2 Scheme 8) with bromopolystyrene gave the resin-bound carboxylic acid (1 Scheme 20).

Polymer-bound benzoic acid can be prepared by forming a Grignard reagent from bromophenyl derivative (1 Scheme 1) and reacting with $CO_2$ followed by acid work-up to give 4-allyldimethylsilylbenzoic acid (2 Scheme 20). Esterification in methanol by catalytic amount of thionyl chloride gave methyl 4-allyldimethylsilylbenzoate (3 Scheme 20). This compound can be connected to the polystyrene resin by hydroboration followed by Suzuki coupling.

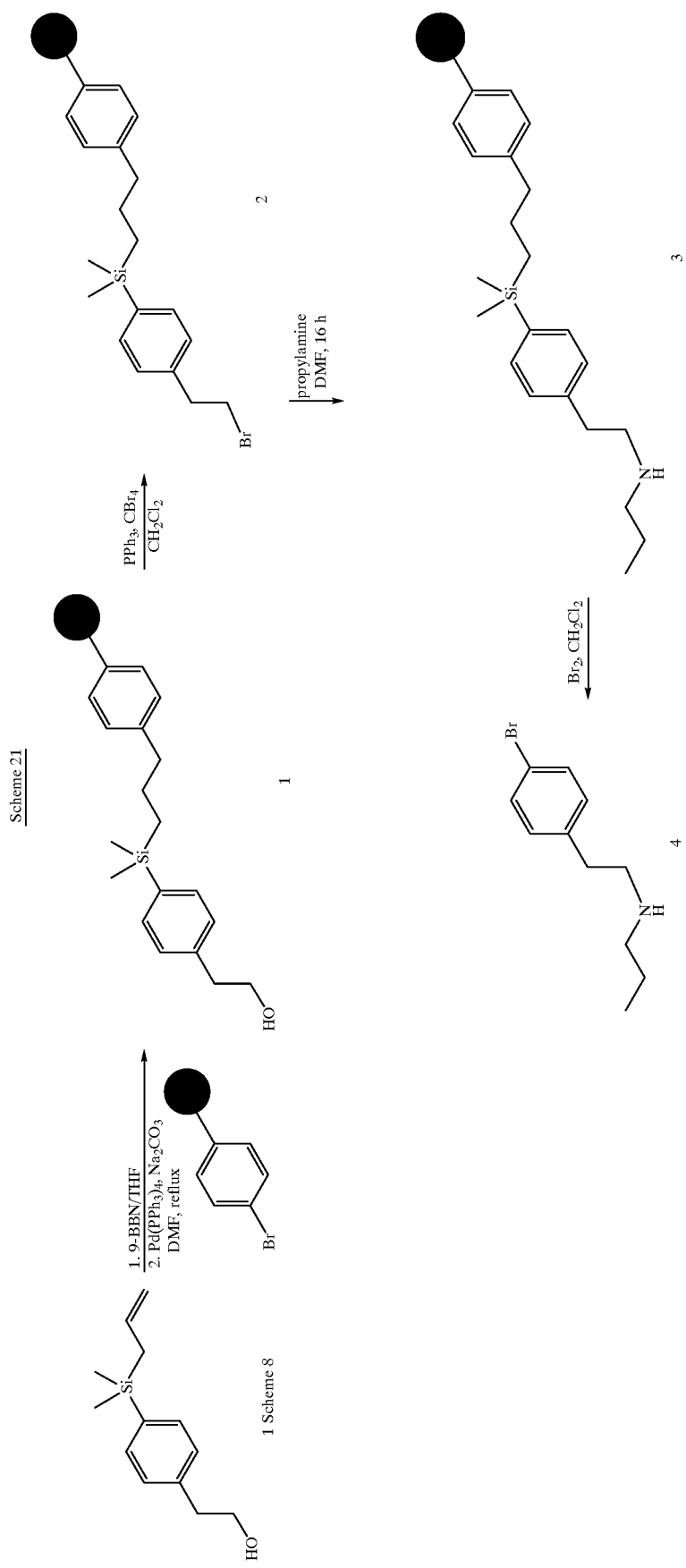

4-Allyldimethylsilylphenethyl alcohol (1 Scheme 8) was attached to the bromopolystyrene under the standard coupling conditions (hydroboration with 9-BBN followed by a Suzuki coupling reaction) as shown in Scheme 21.

The resulting polymer-bound primary alcohol (1 Scheme 21) was converted to the bromide (2 Scheme 21). To demonstrate the utility of the resin-bound bromide (2 Scheme 21) in solid-phase organic synthesis, it was reacted with propylamine to obtain the polymer-bound secondary amine (3 Scheme 21), which can be cleaved with bromine to afford N-4-bromophenethyl-N-propylamine (4 Scheme 21).

Scheme 22

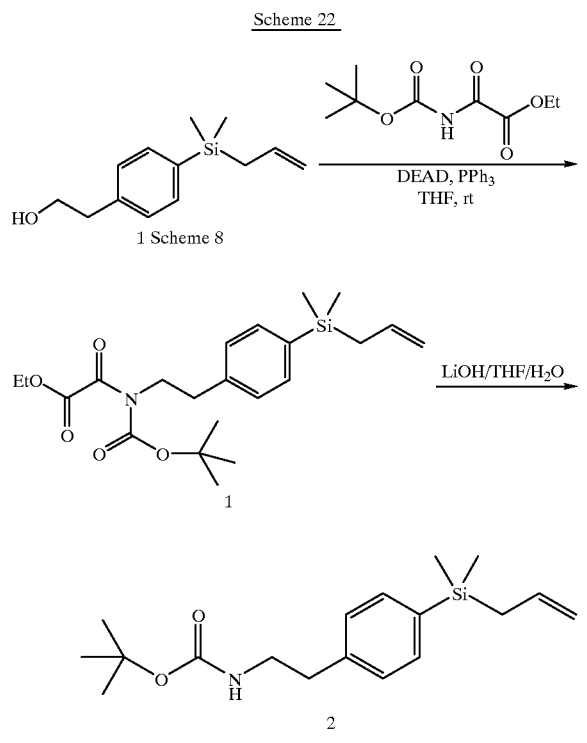

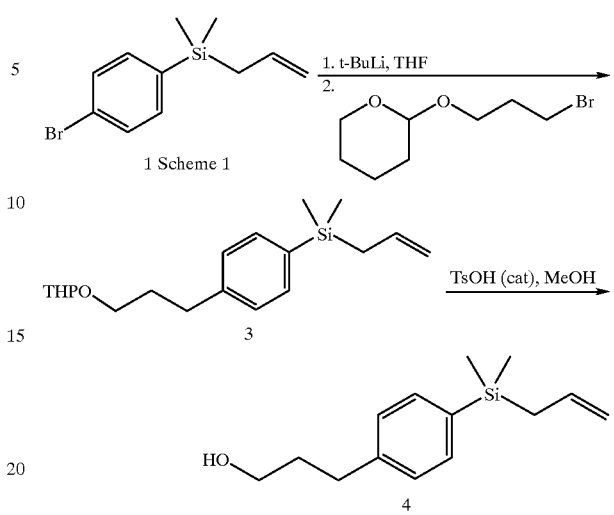

By following the similar reaction sequence as shown in Scheme 16, polymer-bound phenethylamine was synthesized. Mitsunobu reaction of 4-allyldimethylsilylphenethyl alcohol (1 Scheme 8) with N-Boc protected ethyl oxamate followed by hydrolysis afforded Boc-protected silylated phenethylamine (2 Scheme 22). Usual coupling conditions (Hydroboration with 9-BBN followed by Suzuki coupling) with bromopolystyrene as described in Scheme 16 can link the Boc-protected silylated phenethylamine (2 Scheme 22) to the polymer and can also be used for the reactions demonstrated in Scheme 16.

Using 3-carbon homologation reactions, 3-(4-allyldimethylsilylphenyl)-1-propanol (4 Scheme 22) was prepared as follows. Treatment of (1 Scheme 1) with t-butyllithium followed by reaction with 2-(3-bromopropoxy)tetrahydro-2H-pyran afforded THP protected silyl intermediate (3 Scheme 22). The THP group was removed to give the desired 3-(4-allyldimethylsilylphenyl)-1-propanol (4 Scheme 22). The 3-carbon homologated compounds, can also undergo the same reactions demonstrated in Scheme 16.

Scheme 23
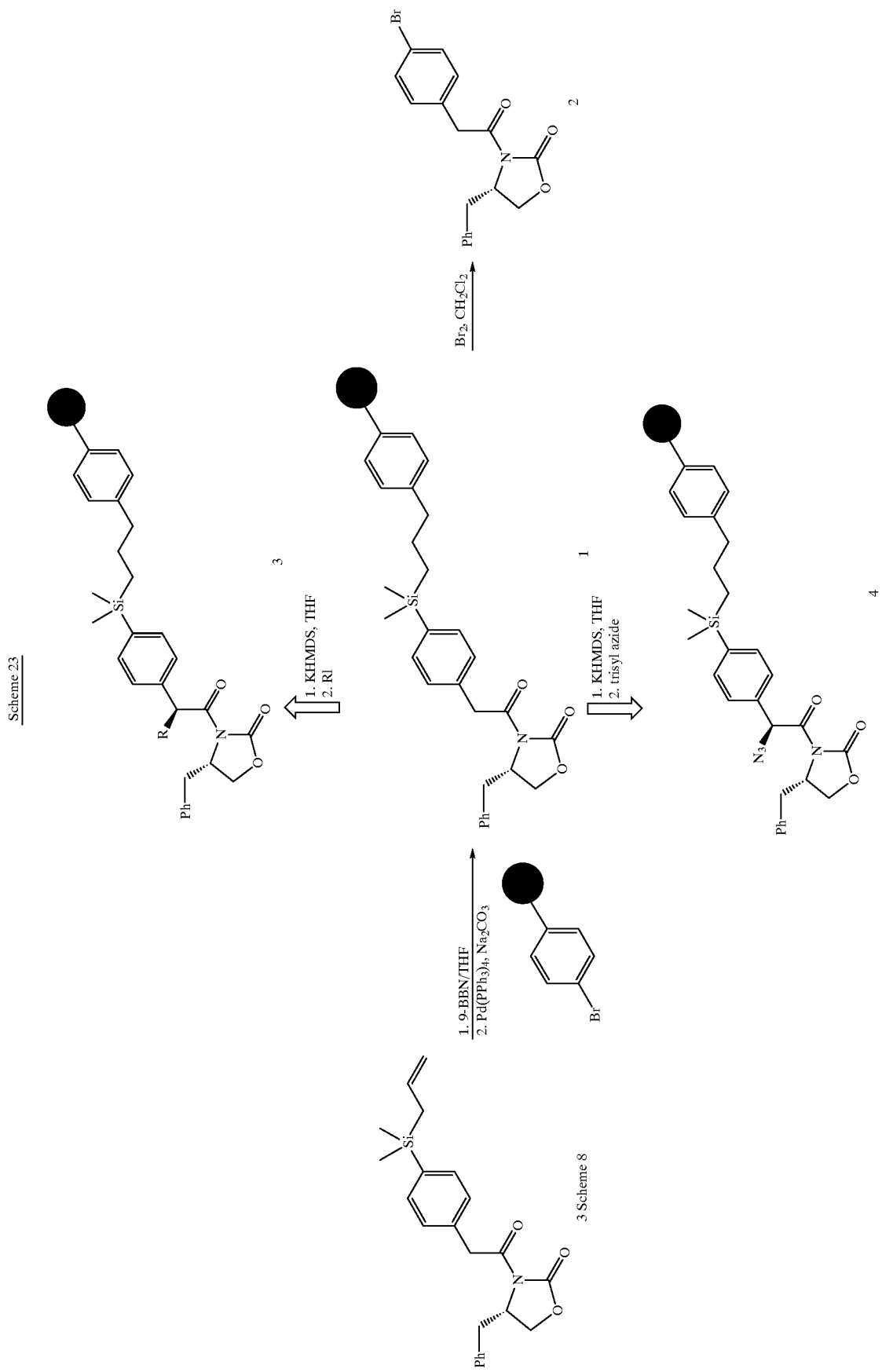

Polymer-bound carboxylic acid compound (1 Scheme 20) is useful for solid-phase organic synthesis of amides and esters. This polymer-bound compound can be used for immobilizing molecules that can form a covalent bond with carboxylic acid function. By derivatizing the carboxylic acid with an appropriate chiral auxiliary, enantioselective substitution at the α-position with various electrophiles can be achieved. This approach can provide a library of α-substituted phenylacetic acids on the solid support which can be further utilized, e.g., reactions suggested in Scheme 20.

Scheme 23 illustrates a process for preparing the polymer-bound chiral auxiliary (1 Scheme 23). Hydroboration of chiral imidate (3 Scheme 8) with 9-BBN followed by Suzuki coupling with bromopolystyrene gave polymer-bound chiral imidate (1 Scheme 23). Cleavage of the resin (1 Scheme 23) with Br$_2$ afforded bromo-substituted imidate (2 Scheme 23). Generation of potassium enolate from (1 Scheme 23) and subsequent treatment of the enolate with various alkyl iodide provides a library of polymer-bound α-alkyl imidate (3 Scheme 23). Treatment of potassium enolate from (1 Scheme 23) with trisylazide affords a polymer-bound α-azido compound (4 Scheme 23).

Functionalized organozinc compounds can be generated under mild conditions using activated zinc developed by Rieke and many organozincs are commercially available. As shown in Scheme 24, palladium mediated cross-coupling reaction of silylated-iodobenzene (1 Scheme 24) to 3-ethoxy-3-oxopropylzinc bromide provided a 3-carbon homologated silyl compound (2 Scheme 24). This compound can be attached to the bromopolystyrene resin under the usual coupling conditions (hydroboration with 9-BBN followed by Suzuki coupling). The ester function can be further derivatized to various other functional groups, such as alcohol, aldehyde, and acid. In the same manner as described above, cross-coupling of silylated iodobenzene (1 Scheme 24) to (4-carbethoxyphenyl)zinc iodide gave silylated biphenyl system with ester function (3 Scheme 24). Thus, the cross-coupling reactions of silylated iodobenzene (1 Scheme 24) to other organozincs can be used to produce a variety of compounds.

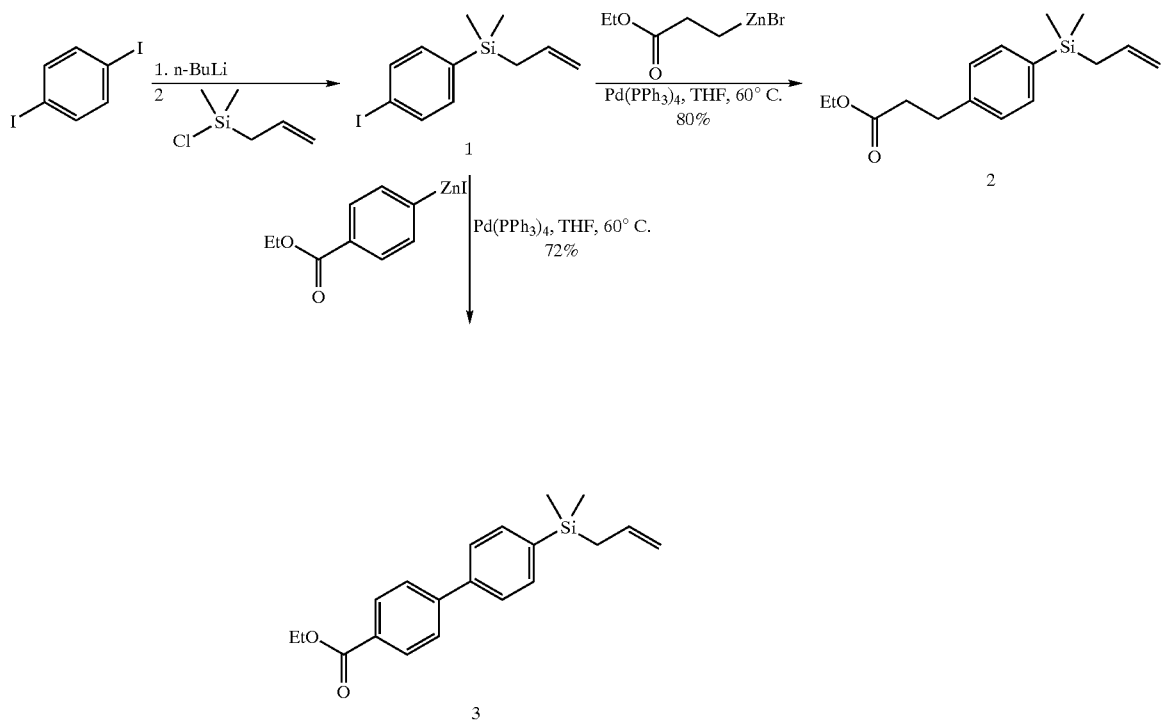

Scheme 24

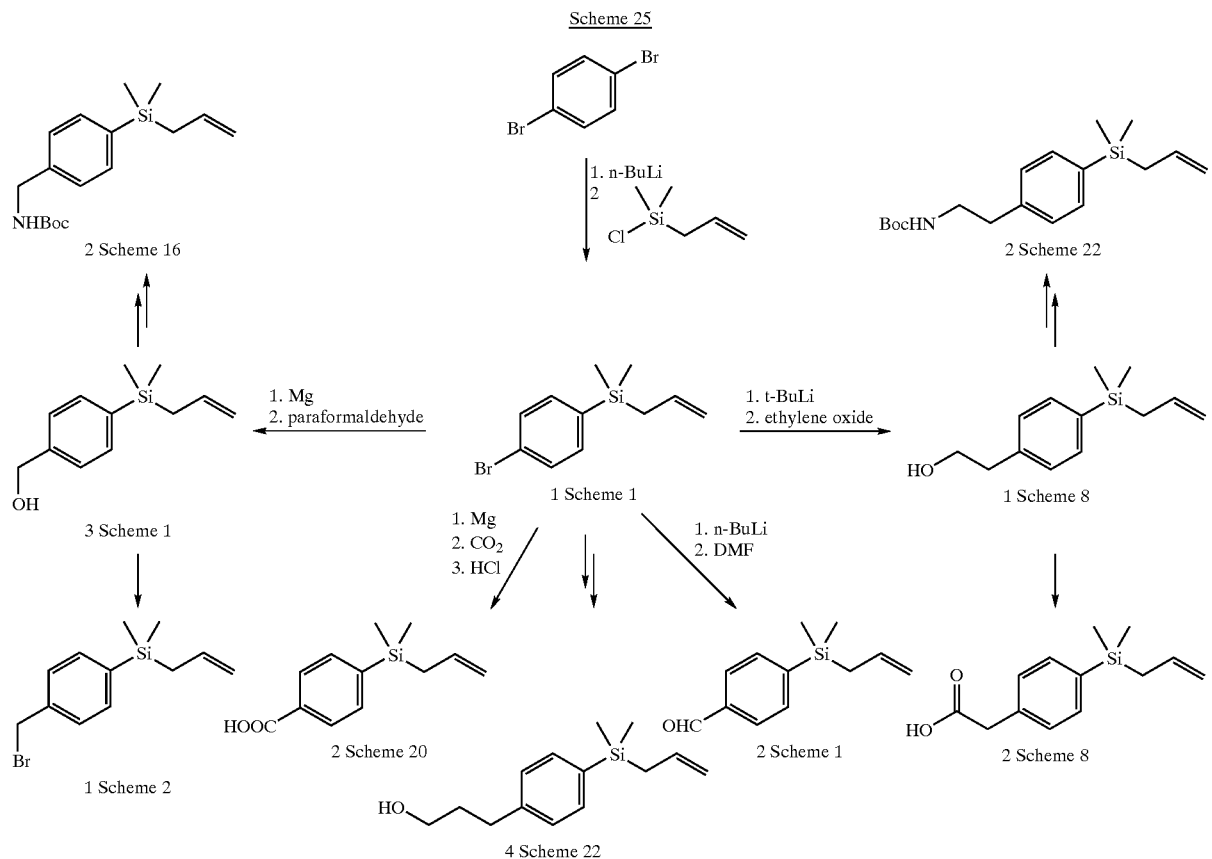

Scheme 25

In Scheme 25, various functional group transformation reactions are shown. It should be noted that most of the silylated compounds with different functional groups synthesized either in solution phase or on the solid support are derived from the common intermediate (1 Scheme 1); however, it should be appreciated that the functional group transformation reactions shown in Scheme 24 can be applied to other aromatic systems, such as naphthalenes and heteroaromatics.

Scheme 26
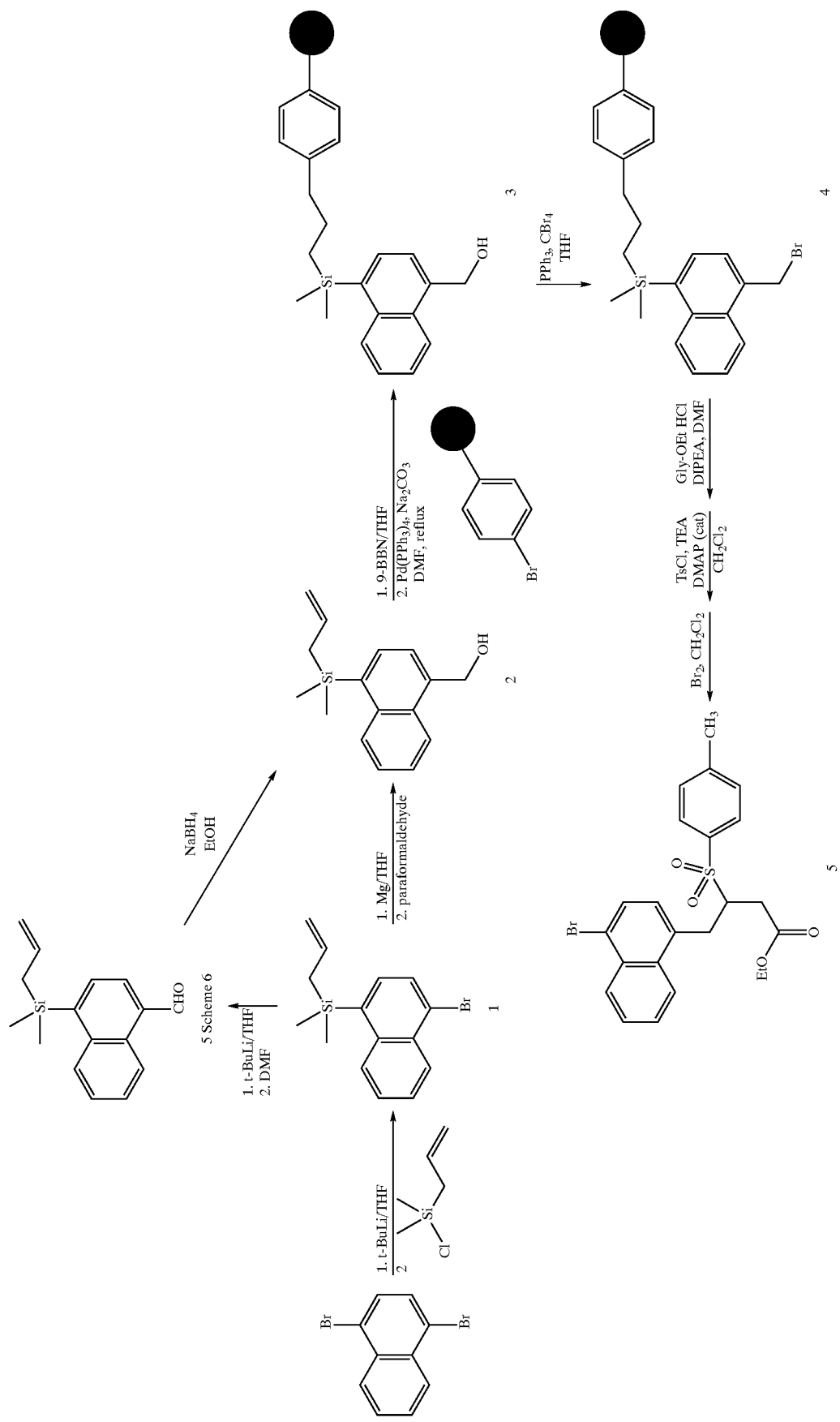

Scheme 26 illustrates compounds and methods of the present invention which have aromatic systems other than phenyl group. As illustrated in Scheme 26, lithium-halogen exchange of 1,4-dibromonaphthalene followed by treatment with allylchlorodimethylsilane afforded silylated intermediate (1 Scheme 26). Grignard reagent of the intermediate (1 Scheme 26) was reacted with paraformaldehyde to afford silylated naphthalene methanol (2 Scheme 26). Alternatively, quenching of the lithiated intermediate (1 Scheme 26) with anhydrous DMF gave an aldehyde (5 Scheme 6) and subsequent reduction of this aldehyde with NaBH$_4$ gave the silylated naphthalene methanol (2 Scheme 26). Hydroboration of (2 Scheme 26) and subsequent Suzuki coupling of the resulting borane complex produced polymer-bound hydroxy compound (3 Scheme 26). The polymer-bound hydroxy compound (3 Scheme 26) was brominated to give a polymer-bound bromide compound (4 Scheme 26), which can be used as a building block for various reactions, e.g. as demonstrated in Scheme 17.

Treatment of the polymer-bound bromide compound (4 Scheme 26) with excess Gly-OEt.HCl, DIPEA in DMF overnight followed by reaction of the resin with p-toluenesulfonyl chloride (TEA, DMAP in CH$_2$Cl$_2$) and cleavage with 50% TFA in CH$_2$Cl$_2$ afforded a naphthalene methyl-containing sulfonamide (5 Scheme 26).

Reduction of 2-bromo-5-pyridinecarboxaldehyde (1 Scheme 27) with sodium borohydride gave a hydroxymethylpyridine (4 Scheme 27). Protection of this alcohol followed by silylation reaction gave 2-[(2-allyldimethylsilylpyridin-5-yl)methoxy]tetrahydro-2H-pyran (6 Scheme 27).

Alternatively, selective lithiation of 2,5-dibromopyridine at C-5 and treating with allychlorodimethylsilane gave 5-allyldimethylsilyl-2-bromopyridine (7 Scheme 27). The second lithiation of (7 Scheme 27) with n-butyllithium followed by treatment with anhydrous DMF yielded 5-allyldimethylsilyl-2-pyridinecarboxaldehyde (8 Scheme 27) which was reduced to the corresponding alcohol (9 Scheme 27). Compounds (3 Scheme 27), (6 Scheme 27), and (9 Scheme 27) can be attached to a polymeric resin and used in solid-phase synthesis of pyridine containing molecules.

Scheme 28

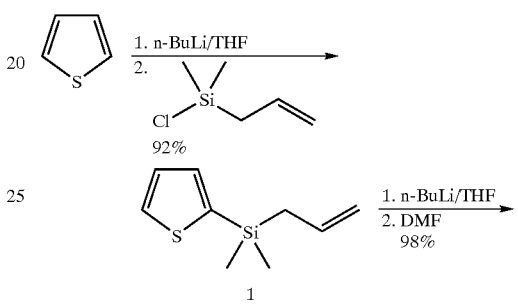

Scheme 27

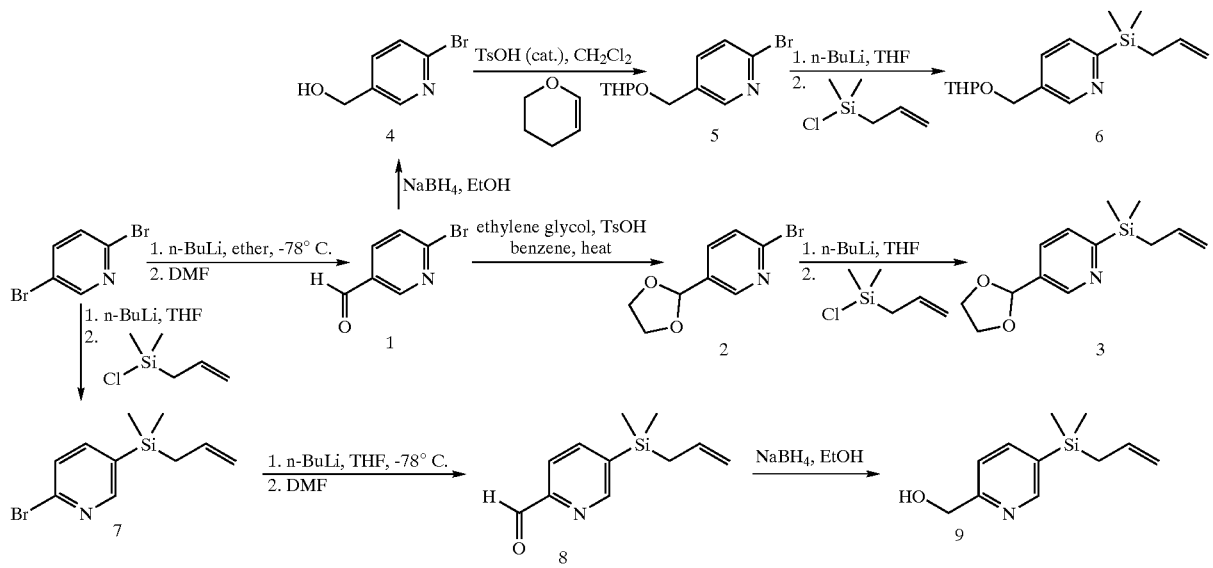

Scheme 27 shows applicability of the present invention to compounds containing heteroaromatic ring moieties. Selective lithiation of 2,5-dibromopyridine at C-5 position by n-butyllithium followed by quenching with anhydrous DMF gave 2-bromo-5-pyridinecarboxaldehyde (1 Scheme 27). Refluxing the aldehyde with ethylene glycol in the presence of p-toluenesulfonic acid provided 1,3-dioxolane analog (2 Scheme 27). Lithiation of (2 Scheme 27) with n-butyllithium followed by treatment with allychlorodimethylsilane afforded 2-(5-allyldimethylsilyl-2-pyridyl)-1,3-dioxolane (3 Scheme 27).

-continued

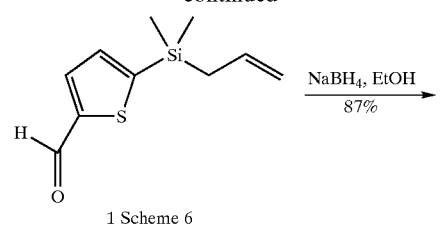

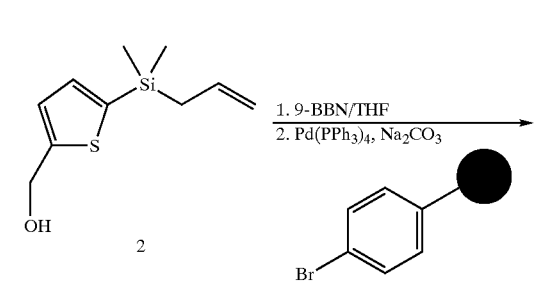

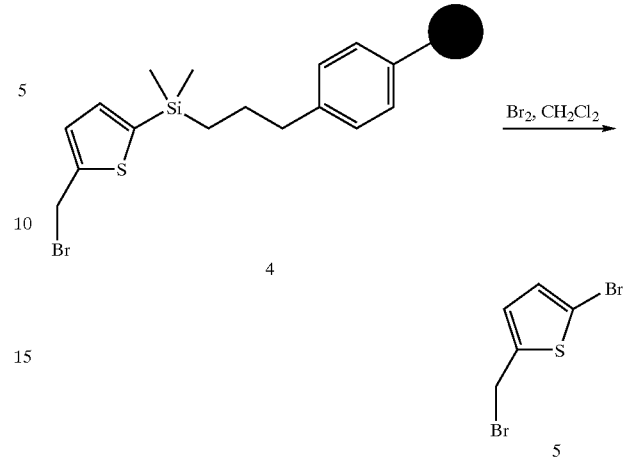

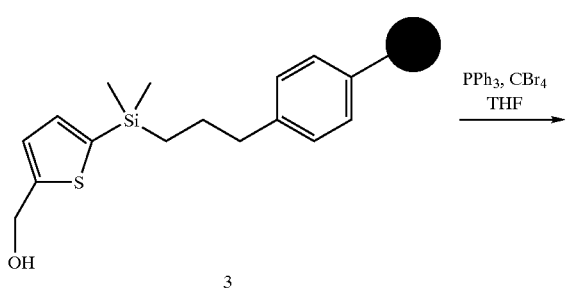

Application of the silylated building block strategy for polymer-bound aromatics were applied for thiophene as shown in Scheme 28. Lithiation of thiophene with n-butyllithium followed by treatment of with allylchlorodimethylsilane afforded 2-allyldimethylsilylthiophene (1 scheme 28). Lithiation of this compound with n-butyllithium followed by quenching with anhydrous DMF resulted in 2-allyldimethylsilylthiophene-5-carboxaldehyde (1 Scheme 6). Reduction of the aldehyde (1 Scheme 6) to alcohol (4 Scheme 28) with sodium borohydride and subsequent coupling with bromopolystyrene under usual conditions provided polymer-bound thienyl methanol compound (3 Scheme 28) which can be further derivatized to reactive halide (4 Scheme 28). These building block can be utilized for various reactions, including those shown in Scheme 17.

Scheme 29

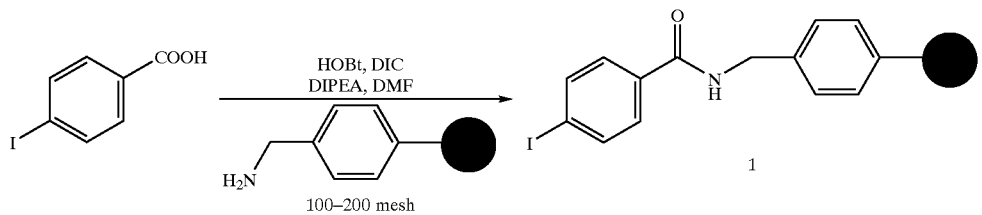

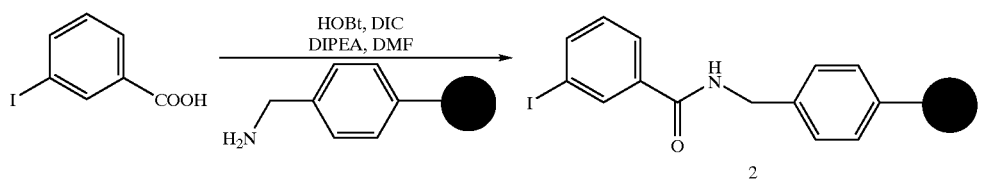

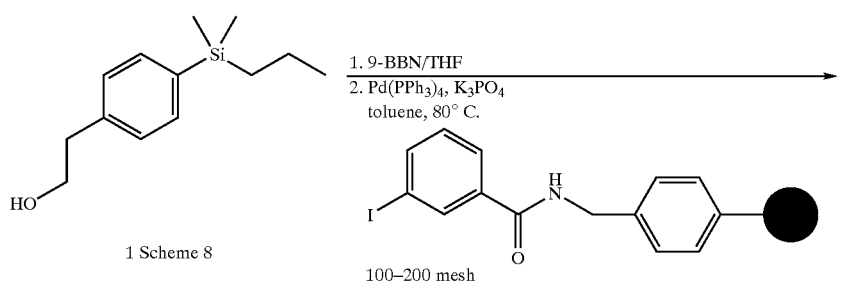

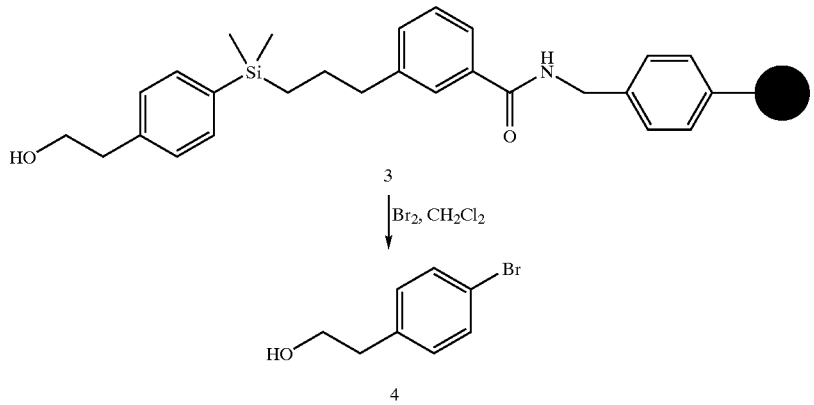

Other polymeric linkers that can be use for Suzuki coupling reactions of various silylated organoborane complexes can be prepared as follows. Aminomethylated polystyrene resin (100–200 mesh) was reacted with 4-iodobenzoic acid (or 3-iodobenzoic acid) under usual peptide coupling conditions gave polymer-bound iodobenzoyl compounds (1 Scheme 29 and 2 Scheme 29).

Hydroboration of 4-allyldimethylsilylphenethyl alcohol (1 Scheme 8) followed by Suzuki coupling reaction with the linker (2 Scheme 29) resulted in polymer-bound phenethyl alcohol compound (3 Scheme 29) which can be cleaved with bromine to give 4-bromophenethyl alcohol (4 Scheme 29).

Amide bond formation of iodobenzoic acids with amino functionalized resins, such as Tentagel resin and PEGA, provides various other linkers which can be utilized for Suzuki coupling reaction for attachment of various compounds of the present invention.

Additional objects, advantages, and novel features of this invention will become apparent to those skilled in the art upon examination of the following examples thereof, which are not intended to be limiting.

EXAMPLES

Preparation of 1-Allyldimethylsilyl-4-bromobenzene (1 Scheme 1).

To a solution 1,4-dibromobenzene (28.3 g, 120 mmol) in dried THF (300 mL) at −78° C. was added n-butyllithium (40.0 mL, 2.5 M solution in hexanes, 100 mmol) over a period of 20 min. After 30 min of further stirring at −78° C., allylchlorodimethylsilane (13.5 g, 100 mmol) in THF (50 mL) was added dropwise over a period of 20 min, and the reaction mixture was warmed to room temperature. After stirring for 1 h at room temperature the reaction mixture was concentrated, and the residue was extracted with ether and brine. The organic layer was dried ($Na_2SO_4$) and distilled under reduced pressure to provide colorless liquid (21.9 g, 82%, b.p. 72° C./0.1 mmHg); $^1$H NMR (300 MHz, $CDCl_3$) δ 0.31 (s, 6 H), 1.77 (d, J=8.07 Hz, 2 H), 4.87 (m, 1 H), 4.92 (m, 1 H), 5.78 (ddt, J=17.55, 9.51, and 8.07 Hz, 1 H), 7.41 (d, J=8.28 Hz, 2 H), 7.52 (d, J=8.28 Hz, 2H); $^{13}$C NMR (75 MHz, $CDCl_3$) −3.5 (2 C), 23.6, 113.8, 123.9, 130.9 (2 C), 134.2, 135.3 (2 C), 137.5; HRMS calcd for $C_{11}H_{15}BrSi$ 254.0127 and 254.0107, found 254.0128 and 256.0109.

Preparation of 4-Allyldimethylsilylbenzaldehyde (2 Scheme 1).

To a solution of 1-allyldimethylsilyl-4-bromobenzene (1 Scheme 1, 1.3 g, 5 mmol) in dry THF (70 mL) at −78° C. was added t-butyllithium (3.0 mL, 1.7 M solution in pentane, 5.1 mmol) over a period of 10 min. After 30 min stirring at −78° C., anhydrous DMF (750 μL, 10 mmol) was added dropwise. The reaction mixture was stirred further for 1 h and warmed to room temperature. Concentrated $NH_4Cl$ (2 mL) was added to the solution, and the reaction mixture was concentrated. The residue was extracted with ethyl acetate (20 mL) and brine (5 mL), and the organic layer was dried ($Na_2SO_4$), concentrated. The crude product was purified by column chromatography (1:15 ethyl acetate/hexanes) to afford a colorless oil (860 mg, 82%); $^1$H NMR (300 MHz, $CDCl_3$) δ 0.32 (s, 6 H), 1.78 (d, J=8.10 Hz, 2 H), 4.84 (s, 1 H), 4.89 (m, 1 H), 5.76 (m, 1 H), 7.67 (d, J=8.10 Hz, 2 H), 7.85 (d, J=8.10 Hz, 2 H), 10.05 (s, 1 H); $^{13}$C NMR (75 MHz, $CDCl_3$) −3.4 (2C), 23.5, 114.2, 128.8 (2C) 133.7, 134.4, (2C), 136.9, 147.6, 192.8; HRMS calcd for $C_{12}H_{16}OSi$ 204.0971, found 204.0972

Preparation of 4-Allyldimethylsilylbenzaldehyde (2 Scheme 1).

A solution of 2-(4-allyldimethylsilylphenyl)-1,3-dioxolane (3 Scheme 18, 12 g, 52.5 mmol) and p-toluenesulfonic acid (100 mg) in acetone (300 mL) was heated under reflux for 3 h. The reaction mixture was concentrated under reduced pressure, and acetone (300 mL) was added to the residue. After refluxing for 3 h, the solution was concentrated, and the crude oil was purified by silica gel chromatography (1:20 ethyl acetate/hexanes) to afford a colorless oil (9.2 g, 86%); $^1$H NMR (300 MHz, $CDCl_3$) δ 0.32 (s, 6 H), 1.78 (d, J=8.10 Hz, 2 H), 4.84 (s, 1 H) 4.89 (m, 1 H), 5.76 (m, 1 H), 7.67 (d, J=8.10 Hz, 2 H), 7.85 (d, J=8.10 Hz, 2 H), 10.05 (s, 1 H); $^{13}$C NMR (75 MHz, $CDCl_3$) −3.4 (2C), 23.5, 114.2, 128.8 (2C) 133.7, 134.4, (2C), 136.9, 147.6, 192.8; HRMS calcd for $C_{12}H_{16}OSi$ 204.0971, found 204.0972.

Preparation of O-tetrahydropyranyl-4-bromobenzylether (5 Scheme 1).

To a solution of 4-bromobenzylalcohol (4 Scheme 4, 9.7 g, 51.8 mmol) and 3,4-dihydro-2H-pyran (5.2 mL, 57 mmol) in dichloromethane (150 mL) was added p-TsOH (200 mg) and the mixture was stirred for 5 h at room temperature. The reaction mixture was concentrated, and column chromatography (1:6 ethyl acetate/hexanes) gave the desired compound as a colorless liquid (14.0 g, 99%); $^1$H NMR (300 MHz, $CDCl_3$) δ 1.51–1.93 (6 H), 3.55 (m, 1 H), 3.90 (m, 1 H), 4.46 (d, J=12.15 Hz, 1H), 4.70 (t. J=3.46 Hz, 1 H), 4.74 (d, J=12.15 Hz, 1 H), 7.24 (d, J=8.52 Hz, 2 H), 7.47 (d, J=8.52 Hz, 2 H); $^{13}$C NMR (75 MHz, $CDCl_3$) 19.4, 25.5, 30.6 62.2 68.1, 97.8, 121.4, 129.5 (2C), 132.5 (2C), 137.4; HRMS calcd for $C_{12}H_{15}BrO_2$ 270.0255 and 272.0236, found 270.0230 and 272.0226.

Preparation of O-tetrahydropyranyl-4-allyldimethylsilylbenzylether (6 Scheme 1).

To a solution of O-tetrahydropyranyl-4-bromobenzylether (5 Scheme 1, 10.0 g, 37 mmol) in dried THF (200 mL) at −78° C. was added n-butyllithium (14.8 mL, 2.5 M solution in hexanes, 37 mmol) over a period of 10 min. After 30 min of further stirring at −78° C., allylchlorodimethylsilane (5.0 g, 37 mmol) in THF (20 mL) was added dropwise over a period of 30 min, and the reaction mixture was warmed to room temperature. After 1 h concentrated $NH_4Cl$ (1 mL) was added, and the reaction mixture was concentrated, purified by column chromatography (1:10 ethyl acetate/hexanes) to afford a colorless liquid (8.4 g, 78%); $^1H$ NMR (300 MHz, $CDCl_3$) δ 0.32 (s, 6 H), 1.52–1.97 (6 H), 1.81 (d, J=8.04 Hz, 2 H), 3.57 (m, 1 H), 3.97 (m, 1 H), 4.53 (d, J=12.06 Hz, 1 H), 4.76 (t, J=3.51 Hz, 1 H), 4.83 (d, J=12.06 Hz, 1 H), 4.86 (m, 1 H), 4.93 (m, 1 H), 5.83 (ddt, J=16.80, 10.18, 8.04 Hz, 1 H), 7.40 (d, J=8.01 Hz, 2 H), 7.54 (d, J=8.01 Hz, 2 H); $^{13}C$ NMR (75M Hz, $CDCl_3$) −3.3 (2C), 19.4, 23.8, 25.6, 30.6, 62.1, 68.8, 97.8, 113.5, 127.2 (2C), 133.8 (2C), 134.7, 137.8, 139.2; HRMS calcd for $C_{17}H_{26}O_2Si$ 290.1702, found 290.1716.

Preparation of 4-Allyldimethylsilylbenzyl Alcohol (3 Scheme 1).

O-tetrahydropyranyl-4-allyldimethylsilylbenzylether (6 Scheme 1, 8.0 g, 28 mmol) was treated with catalytic amount of p-TsOH (150 mg) in methanol (150 mL). After stirring overnight the reaction mixture was concentrated and purified by column chromatography (1:5 ethyl acetate/hexanes) to afford a colorless oil (5.3 g, 92%); $^1H$ NMR (300 MHz, $CDCl_3$) δ 0.30 (s, 6 H), 1.77 (dt, J=8.10, 1.05 Hz, 2 H), 2.28 (bs, OH, 1 H), 4.66 (s, 2 H), 4.85 (s, 1 H), 4.92 (dt, J=8.10, 1.05 Hz, 1 H), 5.81 (ddt, J=10 20, 8.70, 8.10 Hz, 1 H), 7.36 (d, J=8.10 Hz, 2 H), 7.53 (d, J=8.10 Hz, 2 H); $^{13}C$ NMR (75 MHz, $CDCl_3$) −3.3 (2C), 23.8, 65.2, 113.5, 126.4 (2C), 134.0 (2C), 134.6, 138.0, 141.8.

Preparation of 4-Allyldimethylsilylbenzyl Bromide (1 Scheme 2).

To a mixture of 4-allyldimethylsilylbenzyl alcohol (3 Scheme 1, 17.7 g, 86 mmol) and triphenylphosphine (22.5 g, 86 mmol) in dichloromethane (200 mL) at 0° C. was added carbon tetrabromide (28.4 g, 86 mmol) portion-wise. The reaction mixture was stirred at room temperature for 2 h and concentrated. The residue was triturated with ethyl acetate (200 mL) and the precipitated solid was removed by filtration. The filtrate was concentrated, and the residue was triturated with ethyl acetate/hexanes (1:1), then the precipitated solid was removed by filtration (this procedure was repeated 3 times). After drying and concentration of the residue, column chromatography (1:20 ethyl acetate/hexanes) gave a colorless liquid (15.7 g, 68%); $^1H$ NMR (300 MHz, $CDCl_3$) δ 0.40 (s, 6 H), 1.87 (d, J=8.01 Hz, 2 H), 4.57 (s, 2 H), 4.96 (s, 1 H), 5.00 (m, 1 H), 5.88 (ddt, J=16.95, 10 47, 8.01 Hz, 1 H), 7.48 (d, J=8.01 Hz, 2 H), 7.61 (d, J=8.01 Hz, 2 H); $^{13}C$ NMR (75 MHz, $CDCl_3$) −3.3 (2C), 23.7, 33.7, 113.8, 128.4 (2C), 134.3 (2C), 134.5, 138.5, 139.3; HRMS calcd for $C_{12}H_{17}BrSi$ 268.0283 and 270.0263, found 268.0216 and 270.0232.

Preparation of (3R,6S)-6-(4-Allyldimethylsilylbenzyl)-3-isopropyl-2,5-diethoxy-3,6-dihydropyrazine (2 Scheme 2).

n-Butyllithium (10.2 mL, 1.6 M solution in hexanes, 16.5 mmol) was injected into a solution of (3R)-3-isopropyl-2,5-diethoxy-3,6-dihydropyrazine (3.5 g, 16.5 mmol) in THF (70 mL) at −78° C. After 30 min of further stirring, 4-allyldimethylsilylbenzyl bromide (1 Scheme 2, 4.4 g, 16.5 mmol) in dry THF (30 mL) was added to the reaction mixture over a period of 1 h. After 1 h, saturated $NH_4Cl$ (1 mL) was added and the reaction mixture was allowed to warm to room temperature. The reaction mixture was concentrated, diluted with ethyl acetate (100 mL), and extracted with brine (20 mL×2). The organic layer was concentrated and the residue was purified by column chromatography (1:25 ethyl acetate/hexanes) to afford a colorless oil (4.7 g, 71%); $^1H$ NMR (300 MHz, $CDCl_3$) δ 0.28 (s; 6 H), 0.65 (d, J=6.75 Hz, 3 H), 0.96 (d, J=6.75 Hz, 3 H), 1.29 (t, J=7.05 Hz, 3 H), 1.35 (t) J=7.09 Hz, 3 H), 1.74 (d, J=8.05 Hz, 2 H), 2.19 (quintet of d, J=6.87, 3.21 Hz, 1 H), 3.10 (d, J=4.92 Hz, 2 H), 3.28 (m, 1 H), 4.07–4.24 (4 H), 4.31 (app q, J=4.50 Hz, 1 H), 4.83 (s, 1 H), 4.87 (m, 1 H), 5.77 (ddt, J=15.87, 11.13, 8.08 Hz, 1 H), 7.14 (d, J=7.98 Hz, 2 H), 7.38 (d, J=7.98 Hz, 2 H); $^{13}C$ NMR (75 MHz, $CDCl_3$) −3.4 −3.3, 14.5, 16.6, 19.1, 23.9, 31.3, 40.2, 56.7, 60.2, 60.4, 60.5, 113.3, 129.5 (2C), 133.2 (2C), 134.7, 135.9, 138.5, 162.2, 163.5; HRMS calcd for $C_{23}H_{36}N_2O_2Si$ 400.2546, found 400.2543.

Preparation of Resin (3 Scheme 2).

To a solution of (3R, 6S)-6-(4-allyldimethylsilylbenzyl)-3-isopropyl-2,5-diethoxy-3,6-dihydropyrazine (2 Scheme 2, 400 mg, 1.0 mmol) in dry THF (3 mL) was added 9-BBN (2.7 mL, 0.5 M solution in THF, 1.1 mmol) dropwise at 0° C. The mixture was gradually warmed to room temperature and stirred overnight. $Pd(PPh_3)_4$ (35 mg, 3 mol %), 4-bromopolystyrene (510 mg, 1.94 mmol/g, 1 mmol), powdered $K_2CO_3$ (414 mg, 3 mmol), DMF (7 mL), and $H_2O$ (1 mL) were added. After the mixture was stirred for 16 h at 60° C., the resin was washed with THF (1×), 1:1 THF/water (2×), water (2×), methanol (2×), and dried under vacuum.

Preparation of N-Fmoc-4-allyldimethylsilylphenylalanine Ethyl Ester (5 Scheme 2).

A solution of (3R,6S)-6-(4-allyldimethylsilylbenzyl)-3-isopropyl-2,5-diethoxy-3,6-dihydropyrazine (2 Scheme 2, 2 g, 5 mmol) in 36 mL THF/1N HCl (8:1) was stirred vigorously for 30 min at room temperature. The solvent was removed under high vacuum and the residue was extracted with aqueous $NaHCO_3$/ethyl acetate. The organic layer was dried, concentrated to give a colorless oil. The undesired valine ethyl ester was removed under high vacuum at 60° C. and the residue was used directly without further purification. To the compound obtained above were added dioxane (20 mL), water (20 mL), $NaHCO_3$ (840 mg, 10 mmol), and the mixture was cooled to 0° C. FmocCl (1.94 g, 7.5 mmol) was added portion-wise and the solution was stirred for 1 h. After removal of the most of dioxane, the residue was extracted with ethyl acetate (50 mL). The organic layer was dried, concentrated, and purified by column chromatography (1:5 ethyl acetate/hexanes) to afford a colorless oil (1.9 g, 75%); $^1H$ NMR (300 MHz, $CDCl_3$) δ 0.32 (s,6H), 1.30 (t, J=7.14 Hz, 3 H), 1.79 (d, J=8.01 Hz, 2H), 3.19 (m, 2 H), 4.24 (q, J=7.14 Hz, 2 H), 4.23–4.28 (1 H), 4.39 (dd, J=10.65, 7.14 Hz, 1 H), 4.52 (dd, J=10.44, 7.14 Hz, 1 H), 4.74 (m, 1 H), 5.44 (d, J=8.25 Hz, NH, 1 H), 5.82 (ddt, J=12.48, 10.44, 8.01 Hz, 1 H), 7.10 (d, J=7.41 Hz, 2 H), 7.38 (d, J=7.41 Hz, 2 H), 7.40–7.50 (4 H), 7.60–7,68 (2 H, 7.82 (d, J=7.41 Hz, 2 H); $^{13}C$ NMR (75 MHz, $CDCl_3$) −3.4 (2C), 14.2, 23.7, 38.3, 47.5, 54.8, 61.6, 67.0, 113.5, 120.1 (2C), 125.2 (2C), 127.2 (2C), 127.7 (2C), 128.9 (2C), 133.9 (2C), 134.7, 136.7, 137.3, 141.4 (2C), 143.9 (2C), 155.7, 171.6; HRMS (M-$C_3H_5$) calcd for $C_{28}H_{30}NO_4Si$ 472.1944, found 472.1965

Preparation of N-Boc-4-allyldimethylsilylphenylalanine (7 Scheme 2).

The same procedure as described for 5 Scheme 2 was followed except that $(Boc)_2O$ was used instead of FmocCl for protection of the amine group; Colorless oil (yield=

64%); $^1$H NMR (300 MHz, CDCl$_3$) δ 0.24 (s, 6 H), 1.19 (t, J=7.14 Hz, 3 H), 1.39 (s, 9 H), 1.72 (d, J=11.1 Hz, 2 H), 3.04 (m, 2 H), 4.13 (t, J=7.14 Hz, 2 H), 4.54 (m, 1 H), 4.79 (m, 1 H), 4.83 (m, 1 H), 5.07 (bd, NH, 1 H); $^{13}$C NMR (75 MHz, CDCl$_3$) −3.4 (2C), 14.1, 23.6, 28.3 (3C), 38.4, 54.4, 61.2, 79.7, 113.4, 128.8 (3C), 133.8 (2C), 134.5, 137.0, 155.1, 171.9. (b) N-Boc-4-allyldimethylsilylphenylalanine ethyl ester (190 mg, 0.5 mmol) was hydrolyzed with a LiOH (60 mg, 2.5 mmol) in THF/H$_2$O (5:1, 15 mL) for 4 h at room temperature. The reaction mixture was concentrated, and the residue was dissolved in ethyl acetate (20 mL). After neutralization of the solution with acetic acid and concentration, the residue was purified by column chromatography (5:1 ethyl acetate/MeOH) to afford a viscous solid (144 mg, 82%); $^1$H NMR (300 MHz, CDCl$_3$) δ 0.29 (s, 6 H), 1.41 (s, 9 H), 1.76 (d, J=7.68 Hz, 2 H), 3.05–3.32 (2 H), 4.48 (m, 1 H), 4.86 (m, 1 H), 4.91 (m, 1 H), 5.80 (m, 1 H), 7.24 (d, J=7.29 Hz, 2 H), 7.47 (d, J=7.29 Hz, 2 H).

Preparation of Resin (6 Scheme 2).

To a solution N-Fmoc-4-allyldimethylsilylphenylalanine ethyl ester (5 Scheme 2, 550 mg, 1.07 mmol) in dry THF (3 mL) was added 9-BBN (2.7 mL, 0.5 M solution in THF, 1.17 mmol) dropwise at 0° C. The mixture was gradually warmed to room temperature and stirred for 5 h. Pd(PPh$_3$)$_4$ (37 mg, 3 mol %), 4-bromopolystyrene (510 mg, 1.94 mmol/g, 1 mmol), powdered K$_2$CO$_3$ (443 mg, 3.21 mmol), DMF (7 mL), and H$_2$O (1 mL) were added. After the mixture was stirred for 16 h at 60° C., the resin was washed with THF (1×), 1:1 THF/water (2×), water (2×), methanol (2×), and dried under vacuum. The loading of the resin, as determined using Fmoc release UV/VIS assay, was found to be 0.57 mmol/g (29% based on the initial loading of the resin).

Preparation of (1 Scheme 3).

To the resin (6 Scheme 2, 193 mg, 0.11 mmol) was added a mixture of 20% piperidine in DMF (8 mL), and the slurry was agitated for 20 min at room temperature. The resin was rinsed with DMF(2×), CH$_2$Cl$_2$ (2×), and DMF (2×). DMF (8 mL), benzoic acid (54 mg, 0.44 mmol), EDC (84 mg, 0.44 mmol), HOBT (59 mg, 44 mmol), and TEA (61 μL, 44 mmol) were added to the resin and the mixture was agitated overnight at room temperature. The resin was rinsed with DMF (2×), 1:1 DMF/water (2×), water (2×), methanol (3×), and dried under vacuum. To the dried resin were added CH$_2$Cl$_2$ (6 mL) and Br$_2$ (50 μL). The cleavage solution was removed, and the resin was rinsed with CH$_2$Cl$_2$ (3 mL). Concentration of the combined filtrates gave the desired product (purity was determined to be higher than 95% based on the $^1$H NMR spectrum); $^1$H NMR (300 MHz, CDCl$_3$) δ 1.31 (t, J=7.14 Hz, 3 H), 3.21 (dd, J=13.79, 5.02 Hz, 1 H), 3.30 (dd, J=13.87, 5.85 Hz, 1 H), 4.25 (q, J=7.14 Hz, 2 H), 5.07 (m, 1 H), 6.65 (bd, NH, 1 H), 7.04 (d, 8.46 Hz, 2 H), 7.43 (d, J=8.46 Hz, 2 H), 7.46–7.49 (2 H), 7.55 (m, 1 H), 7.75–7.78 (2 H); HRMS calcd for C$_{18}$H$_{18}$BrNO$_3$ 375.0476 and 377.0451, found 375.0469 and 377.0442.

Preparation of (1a Scheme 4).

Resin (6 Scheme 2, 200 mg, 0.14 mmol) was treated with 9 ml solution of 20% piperidine in DMF, and the slurry was agitated for 20 min at room temperature. The resin was rinsed with THF(2×), MeOH (2×), and DMF (2×). DMF (8 mL), benzoic acid (54 mg, 0.44 mmol), EDC (84 mg, 0.44 mmol), HOBT (59 mg, 44 mmol), and TEA (61 μL, 44 mmol) were added to the resin and the mixture was agitated overnight at room temperature. The resin was rinsed with DMF (2×), 1:1 DMF/water (2×), water (2×), THF (3×). A mixed solution of THF/H$_2$O (9 ml, 8:1) and LiOH (16 mg, 0.70 mmol) were added to the resin and the slurry was refluxed for 2 h. After washing with THF(2×), MeOH (2×), and DMF (2×), the resin was subjected to coupling with glycine methyl ester hydrochloride (56 mg, 0.44 mmol), EDC (84 mg, 0.44 mmol), HOBT (59 mg, 44 mmol), and TEA (61 μL, 44 mmol) in DMF (80 mL) for 16 h. at room temperature. After washing with DMF (2×), 1:1 DMF/water (2×), water (2×), MeOH (3×), CH$_2$Cl$_2$ (3×) and drying under vacuum, the resin was treated with CH$_2$Cl$_2$/TFA (1:1, 8 mL) for 24 h at room temperature. The cleavage solution was removed, and the resin was rinsed with CH$_2$Cl$_2$ (3 mL). Concentration of the combined filtrates gave the desired product (purity was determined to be higher than 95% based on the $^1$H NMR spectrum); $^1$H NMR (300 MHz, CDCl$_3$) δ 3.18 (dd, J=13.92, 7.44 Hz, 1 H), 3.26 (dd, J=13.92, 6.50 Hz, 1 H), 3.73 (s, 3 H), 3.95 (dd, J=12.85, 5.25 Hz, 1 H), 4.04 (dd, J=12.85, 5.41 Hz, 1 H), 4.93 (dd, J=14,03, 7.42 Hz, 1 H), 6.49 (bt, J=4.83 Hz, NH, 1 H), 6.84 (bd, J=7.65 Hz, NH, 1 H), 7.21–7.36 (5 H), 7.42 (m, 2 H), 7.51 (m, 1 H), 7.72 (m, 2 H); HRMS calcd for C$_{19}$H$_{20}$N$_2$O$_4$, found 340.1426.

Preparation of (1b Scheme 4).

The same procedure as described for (1a Scheme 4) except that the cleavage of the final product was done with Br$_2$ (50 μL) treatment in CH$_2$Cl$_2$ (6 mL) for 5 min afforded (1b Scheme 4); $^1$H NMR (300 MHz, CDCl$_3$) δ 3.17 (d, J=6.81 Hz, 2 H), 3.74 (s, 3 H), 4.00 (d, J=5.49 Hz, 2 H), 4.94 (dd, J=15.12, 6.81 Hz, 1 H), 6.62 (bs, NH, 1 H), 6.89 (bs, NH, 1 H), 7.15 (d, J=8.34 Hz, 2 H), 7.40 (d, J=8.34 Hz, 2 H), 7.41 (m, 2 H), 7.53 (m, 1 H), 7.73 (m, 2 H); HRMS calcd for C$_{19}$H$_{19}$BrN$_2$O$_4$ 418.0528 and 420.0510, found 418.0541 and 420.0554.

Preparation of (1c Scheme 4).

The same procedure as described for (1a Scheme 4) except that the cleavage of the final product was done with ICl (30 mg) treatment in CH$_2$Cl$_2$ (6 mL) for 5 min afforded (1c Scheme 4); $^1$H NMR (300 MHz, CDCl$_3$) δ 3.15 (d, J=6.81 Hz, 2 H), 3.73 (s, 3 H), 4.00 (d, J=5.49 Hz, 2 H), 4.94 (dd, J=14.43, 6.81 Hz, 1 H), 6.69 (bt, J=5.01 Hz, NH, 1 H), 6.92 (d, J=7.68 Hz, NH, 1 H), 7.02 (d, J=8.13 Hz, 2 H), 7.43 (m, 2 H), 7.52 (m, 1 H), 7.61 (d, J=8.13 Hz, 2 H), 7.73 (d, J=7.08 Hz, 2 H); HRMS calcd for C$_{19}$H$_{19}$IN$_2$O$_4$ 466.0389, found 466.0389.

Preparation of (2Z)-methyl-2-acetamido-3-(4-allyldimethylsilylphenyl)prop-2-enoate (1 Scheme 5).

To a solution of methyl-2-acetylamido-2-(dimethoxyphosphinyl)-acetate (4.8 g, 20.0 mmol) in THF (50 mL) at −78° C. was added tetramethylguanidine (3.2 mL, 26 mmol), and the mixture was stirred for 15 min. 4-Allyldimethylsilylbenzaldehyde (2 Scheme 1, 4.1 g, 20.0 mmol) in THF (10 mL) was added, and the mixture was stirred for 1 h at −78° C. and 4 h at room temperature. The mixture was diluted with EtOAc, washed with 1 N HCl, 1 N CuSO$_4$, and saturated NaHCO$_3$, dried over Na$_2$SO$_4$, and concentrated in vacuo. The residue was purified by column chromatography (1:3 ethyl acetate/CH$_2$Cl$_2$) to afford a white powder (5.5 g, 86%); $^1$H NMR (300 MHz, CDCl$_3$) δ 0.29 (s, 6 H), 1.76(d, J=8.40 Hz, 2 H), 2.15 (s, 3 H), 3.85 (s, 3 H), 4.84 (s, 1 H), 4.89 (m, 1 H), 5.77 (m, 1 H), 7.12 (bs, NH, 1 H), 7.37 (s, 1 H), 7.44 (d, J=7.80 Hz, 2 H), 7.52 (d, J=7.80 Hz, 2 H); $^{13}$C NMR (75 MHz, CDCl$_3$) −3.3, 23.3, 23.7, 52.8, 113.9, 125.1, 129.2, 132.8, 134.0, 134.3, 134.5, 141.1, 166.0, 169.8. HRMS (EI) calcd for C$_{17}$H$_{23}$NO$_3$Si 317.1448, found 317.1451.

Preparation of (S)-methyl-2-acetamido-3-(4-allyldimethylsilylphenyl)propanoate (2 Scheme 5).

To a round bottomed flask containing (2Z)-methyl-2-acetamido-3-(4-allyldimethylsilylphenyl)prop-2-enoate (1 Scheme 5, 3.2 g, 10 mmol) in deoxygenated CH$_2$Cl$_2$ (40 mL) was added [(COD)Rh(S,S)-Et-DuPHOS]OTf(7 mg).

After eight vacuum/H$_2$ cycles, the reaction was stirred for 23 h at room temperature under H$_2$ (1 atm). Once the reaction was finished, the solution was passed through a short plug of silica to remove the catalyst to afford a colorless oil (3.2 g. 100%); $^1$H NMR (300 MHz, CDCl$_3$) δ 0.25 (s, 6 H), 1.72 (dd, J=8.10 Hz, 2 H), 1.98 (s, 3 H), 3.10 (m, 2 H), 3.72 (s, 3 H), 4.81 (d, J=1.2 Hz, 1 H), 4.83–4.92 (2 H), 5.76 (m, 1 H), 5.94 (bd, J=7.80 Hz, NH, 1 H), 7.06 (d, J=7.20 Hz, 2 H), 7.42 (d, J=7.20 Hz, 2 H); $^{13}$C NMR (75 MHz, CDCl$_3$) −3.2, 23.3, 23.9, 37.9, 52.6, 53.3, 113.7, 128.9, 134.1, 134.8, 136.9, 137.5, 170.1, 172.5; HRMS (EI) calcd for C$_{17}$H$_{25}$NO$_3$Si 319.1600, found 319.1602.

Preparation of (S)-methyl-3-(4-allyldimethylsilylphenyl)-2-(tert-butoxycarbamido)propanoate (3 Scheme 5).

To a solution of (S)-methyl-2-acetamido-3-(4-allyldimethylsilylphenyl)propanoate (2 Scheme 5, 1.5 g, 4.7 mmol) and DMAP (115 mg, 0.94 mmol) in THF (16 mL) was added di-tert-butyl dicarbonate (2.0 g, 9.4 mmol), and the mixture was heated to reflux for 1 h. After the solution was cooled to room temperature, MeOH (15 mL) and hydrazine monohydrate (912 μL, 18.8 mmol) were added, and the mixture was stirred for 2 h at room temperature. The solvent was evaporated by rotary evaporation, and the residue was subjected to high vacuum to remove the remaining volatile materials. The oily residue was purified by column chromatography (1:7 ethyl acetate/hexanes) to afford a colorless oil (1.7 g, 93%), $^1$H NMR (300 MHz, CDCl$_3$) δ 0.29 (s 6 H), 1.43 (s, 9 H), 1.76 (d, J 7.80 Hz, 2 H), 3.09 (m, 2 H), 3.73 (s, 3 H), 4.62 (m, 1 H), 4.84 (s, 1 H), 4.88 (d J=6.60 Hz, 1 H), 5.20 (bd, NH, 1 H), 5.78(m, 1 H), 7.14 (d, J=7.50 Hz, 2 H), 7.46 (d, J=7.50 Hz, 2 H); $^{13}$C NMR (75 MHz, CDCl$_3$) −3.2, 23.9, 28.5, 38.6, 52.5, 54.6, 80.1, 113.7, 129.0, 134.1, 134.8, 137.1, 137.3, 153.3, 172.6, HRMS (EI) calcd for C$_{20}$H$_{32}$NO$_4$Si 378. 2100, found 378.2101.

Preparation of (2Z)-methyl-2-acetamido-3-(2-allyldimethylsilyl-5-thienyl)prop-2-enoate (2 Scheme 6).

Synthesized from 1 Scheme 6 as described for (1 Scheme 5) and purified by column chromatography (1:1 ethyl acetate/hexanes) to afford a colorless oil (78%); $^1$H NMR (300 MHz, CDCl$_3$) δ 0.32 (s, 6 H), 1.77 (d, J=8.10 Hz, 2 H), 2.21 (s, 3 H), 3.78 (s, 3 H), 4.87 (s, 1 H), 4.91 (m, 1 H), 5.76 (m, 1 H), 7.19 (d J=3.30 Hz, 1 H), 732 (d, J=3.30 Hz, 1 H), 7.76 (s, 1 H); $^{13}$C NMR (75 MHz, CDCl$_3$) −2.3, 23.7, 24.3, 52.7, 114.6, 122.0, 129.4, 133.8, 134.5, 134.7, 141.5, 145.3, 165.7, 170.3; HRMS (EI) calcd for C$_{15}$H$_{21}$NO$_3$SSi 323.1011, found 323.1012.

Preparation of (S)-methyl-2-acetamido-3-(2-allyldimethylsilyl-5-thienyl)propanoate (3 Scheme 6).

Synthesized from 2 Scheme 6 and purified as described for (2 Scheme 5) to afford a colorless oil (98%); $^1$H NMR (300 MHz, CDCl$_3$) δ 0.29 (s, 6 H), 1.74 (d, J=7.80 Hz, 2 H), 2.03 (s, 3 H), 3.39 (d, J=4.80 Hz, 2 H), 3.76 (s, 3 H), 4.80–4.90 (3 H), 5.75 (m, 1 H), 6.24 (bd, J=7.20 Hz, NH, 1 H), 6.83 (d, J=3.30 Hz, 1 H), 7.07 (d, J=3.30 Hz, 1 H); $^{13}$C NMR (75 MHz, CDCl$_3$) −2.1, 23.4, 24.6, 32.1, 52.8, 53.3, 114.1, 128.3, 134.2, 134.9, 138.4, 143.3, 170.0, 171.8; HRMS (EI) calcd for C$_{15}$H$_{23}$NO$_3$SSi 325.1168, found 325.1165.

Preparation of (S)-methyl-3-(2-allyldimethylsilyl-5-thienyl)-2-(tert-butoxycarbamido)propanoate (4 Scheme 6).

Synthesized from 3 Scheme 6 as described for (3 Scheme 5) and purified by column chromatography (1:5 ethyl acetate/hexanes) to afford a colorless oil (90%); $^1$H NMR (300 MHz, CDCl$_3$) δ 0.30 (s, 6 H ), 1.45 (s, 9 H), 1.75 (d, J=8.10 Hz, 2 H), 3.38 (m, 2 H), 3.75 (s, 3 H), 4.60 (m, 1 H), 4.86 (s, 1 H), 4.90 (m, 1 H), 5.19 (d, J=7.50 Hz, NH, 1 H), 5.78 (m, 1 H), 6.87 (d, J=3.00 Hz, 1 H), 7.08 (d, J=3.00 Hz, 1 H); $^{13}$C NMR (75 MHz, CDCl$_3$) −2.1, 24.6, 28.6, 32.6, 52.6, 54.5, 80.2, 100.3, 114.1, 128.3, 134.3, 134.9, 138.1, 143.5, 155.3, 172.0; HRMS (EI) calcd for C$_{18}$H$_{29}$NO$_4$SSi 383.1586, found 383.1585.

Preparation of (2Z)-methyl-2-acetamido-3-(2-allyldimethylsilyl-4-naphthyl)prop-2-enoate (6 Scheme 6).

Synthesized from 5 Scheme 6 as described for (1 Scheme 5) and purified by column chromatography (1:1 ethyl acetate/hexanes) to afford a colorless oil (91%); $^1$H NMR (300 MHz, CDCl$_3$) δ 0.50 (s, 6 H), 1.83 (s, 3 H), 2.00 (d, J=7.80 Hz, 2 H), 3.83 (s, 3 H), 4.86–4.96 (2 H), 5.81 (m, 1 H), 7.45–7.58 (4 H), 7.66 (d, J=7.20 Hz, 1 H), 7.79 (s, 1 H) 7.99 (d, J=7.80 Hz, 1 H), 8.13 (d, J=7.80 Hz, 1 H), $^{13}$C NMR (75 MHz, CDCl$_3$) −1.6, 22.9, 24.4, 52.9, 114.2, 125.5, 125.7, 126.3, 128.1, 128.9, 131.3, 132.6, 133.3, 134.7, 137.3, 139.0, 165.7, 170.0; HRMS (EI) calcd for C$_{21}$H$_{25}$NO$_3$Si 367.1603, found 367.1605.

Preparation of (S)-methyl-2-acetamido-3-(2-allyldimethylsilyl-4-naphthyl)propanoate (7 Scheme 6).

Synthesized from 6 Scheme 6 and purified as described for (2 Scheme 5) to afford a colorless oil (99%); $^1$H NMR (300 MHz, CDCl$_3$) δ 0.49 (s, 6 H), 1.97 (s, 3 H), 2.00 (d, J=7.80 Hz, 2 H), 3.61 (m, 2 H), 3.67 (s, 3 H), 4.80–4.94 (2 H), 5.05 (m, 1 H), 5.80 (bd, J=7.20 Hz, NH, 1 H), 7.22 (d, J=6.60, 1 H), 7.54–7.61 (3 H), 8.10–8.18 (2 H); $^{13}$C NMR (75 MHz, CDCl$_3$) −1.5, 23.1, 24.5, 35.5, 52.5, 53.5, 114.0, 124.7, 125.9, 126.1, 127.0, 129.2, 132.4, 133.5, 134.7, 136.6, 137.7, 172.8; HRMS (EI) calcd for C$_{21}$H$_{27}$NO$_3$Si 369.1757, found 369.1756.

Preparation of (S)-methyl-3-(2-allyldimethylsilyl-4-naphthyl)-2-(tert-butoxycarbamido)propanoate (8 Scheme 6).

Synthesized from 7 Scheme 6 as described for (3 Scheme 5) and purified by column chromatography (1:5 ethyl acetate/hexanes) to afford a colorless oil (92%); $^1$H NMR (300 MHz, CDCl$_3$) δ 0.48 (s, 6 H), 1.41 (s, 9 H), 2.00 (d, J=8.40 Hz, 2 H), 3.40–3.66 (2 H), 3.67 (s, 3 H), 4.75 (m, 1 H), 4.85–4.95 (2 H), 5.09 (bd, NH, 1 H), 5.82 (m, 1 H), 7.25–7.28 (2 H), 7.50–7.63 (3 H), 8.10–8.17 (2 H); $^{13}$C NMR (75 MHz, CDCl$_3$) −1.5, 24.5, 28.6, 36.1, 52.4, 54.6, 80.1, 114.0, 124.8, 125.8, 126.1, 127.1, 129.2, 132.5, 133.5, 134.7, 135.0, 136.5, 137.7, 155.4, 172.9; HRMS (EI) calcd for C$_{24}$H$_{32}$NO$_4$Si 427.2180, found 427.2180.

Preparation of (2Z)-methyl-2-acetamido-4-(4-allyldimethylsilylphenyl)but-2-enoate (10 Scheme 6).

To a solution of methyl-2-acetylamido-2-(dimethoxyphosphinyl)-acetate (1.2 g, 5.0 mmol) in THF (15 mL) at −78° C. was added tetramethylguanidine (815 μL, 6.5 mmol) and the mixture was stirred for 15 min. 4-allyldimethylsilylphenylacetaldehyde (9 Scheme 6, 1.1 g, 5.0 mmol) in THF (4 mL) was added, and the mixture was stirred for 1 h at −78° C. and 4 h at room temperature. The mixture was diluted with EtOAc, washed with 1 N HCl, 1 N CuSO$_4$, and saturated NaHCO$_3$, dried over Na$_2$SO$_4$, and concentrated in vacuo. The residue was purified by column chromatography (1:1 ethyl acetate/hexanes) to afford a colorless oil (760 mg, 45%); $^1$H NMR (300 MHz, CDCl$_3$) δ 0.29 (s, 6 H), 1.76(d, J=7.80 Hz, 2 H), 2.17 (s, 3 H), 3.52 (d, J=7.20 Hz, 2 H), 3.78 (s, 3 H), 4.85 (s, 1 H), 4.91 (d, J=8.10 Hz, 1 H), 5.77 (m, 1 H), 6.84 (t, J=7.20 Hz, 1 H), 7.21 (d, J=7.50 Hz, 2 H), 7.47 (d, J=7.50 Hz, 2 H), 7.56 (s, 1 H); $^{13}$C NMR (75 MHz, CDCl$_3$) −3.2 (2C), 23.5, 23.9, 35.3, 52.7, 113.7, 125.8, 128.4 (2C), 134.3 (2C), 134.8, 136.8, 137.1, 165.4, 169.5; HRMS (EI) calcd for C$_{18}$H$_{25}$NO$_3$Si 331.1605, found 331.1606.

Preparation of (S)-methyl-2-acetamido-3-(4-allyldimethylsilylphenyl)butanoate (11 Scheme 6).

Synthesized from 10 Scheme 6 and purified as described for (2 Scheme 5) to afford a colorless oil (96%); $^1$H NMR (300 MHz, CDCl$_3$) δ 0.28 (s, 6 H), 1.75 (d, J=7.50 Hz, 2 H), 2.01 (s, 3 H), 2.00–2.30 (2 H), 2.65 (m, 2 H), 3.75 (s, 3 H), 4.71 (m, 1 H), 4.85 (s, 1 H), 4.89 (d, J=8.70 Hz, 1 H), 5.79

(m, 1 H), 5.97 (bd, J=8.10 Hz, NH, 1 H), 7.19 (d, J=7.80 Hz, 2 H), 7.45 (d, J=7.80 Hz, 2 H); $^{13}$C NMR (75 MHz, CDCl$_3$) −3.2, 23.1, 23.9, 32.1, 33.8, 52.3, 52.4, 113.7, 128.2, 134.1, 134.8, 136.2, 141.9, 170.8, 173.3; HRMS (EI) calcd for C$_{18}$H$_{27}$NO$_3$Si 333.1757, found 333.1755.

Preparation of (S)-methyl-4-(4-allyldimethylsilylphenyl)-2-(tert-butoxycarbamido)butanoate (12 Scheme 6).

Synthesized from 11 Scheme 6 as described for (3 Scheme 5) and purified by column chromatography (1:5 ethyl acetate/hexanes) to afford a colorless oil (88%); $^1$H NMR (300 MHz, CDCl$_3$) δ 0.28 (s, 6 H), 1.47 (s, 9 H), 1.75 (d, J=7.80 Hz, 2 H), 1.98 (m, 1 H), 2.17 (m, 1 H) 2.69 (m, 2 H), 3.73 (s, 1 H), 4.38 (m, 1 H), 4.84 (s, 1 H), 4.88 (d, J=8.10 Hz, 1 H), 5.21 (bd, NH, 1 H), 5.78 (m, 1 H), 7.19 (d, J=7.80 Hz, 2 H), 7.45 (d, J=7.80 Hz, 2 H); $^{13}$C NMR (75 MHz, CDCl$_3$) −3.2, 24.0, 28.6, 31.9, 34.4, 52.5, 53.5, 80.1, 113.6, 128.2, 134.1, 134.9, 136.2, 142.0, 155.7, 173.4; HRMS (EI) calcd for C$_{21}$H$_{33}$NO$_4$Si 391.2178, found 391.2180.

Preparation of N-acetyl-4-allyldimethylsilylphenylalanal (1 Scheme 7).

To a stirred solution of (2Z)-methyl-2-acetamido-3-(4-allyldimethylsilylphenyl)prop-2-enoate (2 Scheme 5, 1.18 g, 3.7 mmol) in dry toluene (20 mL) at −78° C. was added diisobutylaluminium hydride (1.5 M in toluene, 6.1 mL, 9.2 mmol) over a period of 30 min under N$_2$ atmosphere. After being stirred further for 30 min, the excess diisobutylaluminium hydride was quenched with MeOH (5 ml) at −78° C. The reaction mixture was warmed to room temperature, diluted with ethyl acetate (40 mL), and extracted with 1 N HCl and brine. The organic layer was dried (Na$_2$SO$_4$), concentrated, and purified by silica gel column chromatography using 1:6 ethyl acetate/hexanes to afford a viscous oil (835 mg, 78%); $^1$H NMR (300 MHz, CDCl$_3$) δ 0.24 (s, 6 H), 1.72 (d, J=7.80 Hz, 2 H), 1.96 (s, 3 H), 3.10 (m, 2 H), 4.64 (m, 1 H), 4.80 (s, 1 H), 4.85 (m, 1 H), 5.73 (m, 1 H), 6.57 (d, J=6.90 Hz, NH, 1 H), 7.13 (d, J=7.50 Hz, 2 H), 7.42 (d, J=7.50 Hz, 2 H), 9.58 (s, 1 H); $^{13}$C NMR (75 MHz, CDCl$_3$) −3.2 (2 C), 23.1, 23.8, 35.0, 60.0, 113.7, 128.9 (2C), 134.3 (2C), 134.7, 136.8, 137.6, 170.8, 199.3; HRMS (EI) calcd for C$_{16}$H$_{23}$NO$_2$Si 289.1497, found 289.1495.

Preparation of (2 Scheme 7).

A mixture of N-acetyl-4-allyldimethylsilylphenylalanal (1 Scheme 7, 65 mg, 0.22 mmol), 3-triphenylphosphonium-1-propanol bromide (180 mg, 0.44 mmol), and powdered K$_2$CO$_3$ (91 mg, 0.66 mmol) in dioxane(10 mL) was heated to 90° C. for 90 min. The reaction mixture was concentrated, diluted with ethyl acetate. The organic layer was washed with brine, dried, and purified by silica gel column chromatography using 1:20 methanol/ethyl acetate to afford a colorless oil (45 mg, 63%); $^1$H NMR (300 MHz, CDCl$_3$) δ 0.24 (s, 6 H), 1.71 (dd, J=8.1, 0.9 Hz, 2 H), 1.90 (s, 3 H), 1.96–2.50 (2 H), 2.74 (m, 1 H), 2.87 (m, 2 H), 3.46 (m, 1 H), 3.57 (m, 1 H), 4.79 (d, J=1.2 Hz, 1 H), 4.80–4.92 (2 H), 5.33 (m, 1 H), 5.48 (m, 1 H), 5.70 (bd, NH, 1 H), 5.71 (m, 1 H), 7.16 (d, J=7.5 Hz, 2 H), 7.41 (d, J=7.5 Hz, 2 H); HRMS (EI) calcd for C$_{19}$H$_{30}$NO$_2$Si 332.2044, found 332.2039.

Preparation of 2(S)-[1'(S)-hydroxy-(4-allyldimethylsilyl)phenylethyl]oxirane (3 Scheme 7).

To a vigorously stirred magnesium turnings (730 mg with trace of I$_2$) in 20 mL of dry THF was added a small portion of 1-allyldimethylsilyl-4-bromobenzene (1 Scheme 1, 5.1 g, 20 mmol) and heated to initiate exothermic reaction. The addition was continued over a period of 10 min with frequent heating of the reaction mixture to reflux for another 20 min. The Grignard solution was cooled to room temperature. To a separate reaction flask containing 1,3-butadiene diepoxide (15, 3.5 g, 40 mmol), CuCN (180 mg, 2 mmol) in THF (70 mL) at −78° C. was added the prepared Grignard reagent over a period of 30 min via cannula. After the addition was complete, the reaction mixture was stirred further for 3 h at −78° C. Saturated NH$_4$Cl (5 mL) was added slowly, and the mixture was allowed to warm to room temperature. THF was removed under reduced pressure and the residue was extracted with ethyl acetate and brine. The organic layer was dried (Na$_2$SO$_4$) and concentrated, and the crude orange oil was purified by column chromatography (1:3 ethyl acetate/hexanes) to afford a colorless oil (3.0 g, 57%); $^1$H NMR (300 MHz, CDCl$_3$) δ 0.33 (s, 6 H), 1.80 (d, J=8.04 Hz, 2 H), 2.64 (dd, J=4.89, 2.73 Hz, 2 H), 2.78 (app t, J=4.17 Hz, 1 H), 2.95 (ddd, J=4.80, 4.19, and 2.79 Hz, 2 H), 3.08 (m, 1 H), 3.74 (m, 1 H), 4.88 (m, 1 H), 4.92 (m, 1 H), 5.82 (ddt, J=14.52, 8.28, and 8.20 Hz, 1 H), 7.29 (d, J=7.92 Hz, 2 H), 7.51 (d, J=7.92 Hz, 2 H); $^{13}$C NMR (75 MHz, CDCl$_3$) −3.3 (2 C), 23.8, 41.0, 45.2, 55.0, 72.5, 113.5, 128.9 (2 C), 134.0 (2 C), 134.7, 136.7, 138.2; HRMS (M-CH$_3$) calcd for C$_{14}$H$_{19}$O$_2$Si 247.1154, found 247.1150.

Preparation of 2(S)-[1'(S)-azido-(4allyldimethylsilyl)phenylethyl]oxirane (4 Scheme 7).

To a stirred mixture of 2(S)-[1'(S)-hydroxy-(4-allyldimethylsilyl)phenylethyl]oxirane (3 Scheme 7, 300 mg, 1.1 mmol) and triphenylphosphine (314 mg, 1.2 mmol) in THF (30 mL) at −15° C. were added diethyl azodicarboxylate (DEAD, 188 μL, 1.2 mmol) and diphenylphosphoryl azide (258 μL, 1.2 mmol). After stirring for 1 h at −15° C. and further stirring for 4 h at room temperature, the reaction solution were concentrated, and the residue was purified by column chromatography (1:20 ethyl acetate/hexanes) to afford a colorless oil (145 mg, 45%); $^1$H NMR (300 MHz, CDCl$_3$) δ 0.35 (s, 6 H), 1.82 (d, J=8.04 Hz, 2 H), 2.86 (dd, J=14.01, 8.73 Hz, 1 H), 2.87 (m, 2 H), 3.03 (dd, J=13.98, 4.65 Hz, 1 H), 3.13 (m, 1 H), 3.67 (dt, J=8.73, 5.19 Hz, 1 H), 4.90 (s, 1 H), 4.94 (m, 1 H), 5.84 (ddt, J=16.65, 10 38, 8.16 Hz, 1 H), 7.31 (d, J=7.89 Hz, 2 H) 7.55 (J=7.89 Hz, 2 H).

Preparation of 4-Allyldimethylsilylphenethyl alcohol (1 Scheme 8).

To a solution 1-allyldimethylsilyl-4-bromobenzene (1 Scheme 1, 5.1 g, 20 mmol) in dried THF (30 mL) at −78° C. was added t-butyllithium (12.9 mL, 1.7 M solution in pentane, 22 mmol) over a period of 5 min. The reaction mixture was allowed to warm to room temperature and stirred further for 1 h. The solution was cooled to −78° C. and transferred to the cooled (−78° C.) solution of ethylene oxide (3.5 g, 78 mmol) in dry THF (50 mL) via cannula. The reaction mixture was warmed to room temperature over 30 min and quenched with saturated NH$_4$Cl (5 ml). After evaporation of THF, the residue was extracted with ethyl acetate and water. The organic layer was dried (Na$_2$SO$_4$) and concentrated to give an oil which was distilled to afford the desired product as a colorless oil (2.9 g, 67%, b.p. 100° C./0.1 mmHg); $^1$H NMR (300 MHz, CDCl$_3$) δ 0.32 (s, 6 H), 1.72 (bs, OH, 1 H), 1.79 (d, J=8.01 Hz, 2 H), 2.90 (t, J=6.60 Hz, 2 H), 3.89 (t, J=6.60 Hz, 2 H), 4.88 (m, 1 H), 4.92 (m, 1 H), 5.83 (ddt, J=16.83, 10.20, 8.04 Hz, 2 H), 7.27 (d, J=8.04 Hz, 2 H), 7.52 (d, J=8.04 Hz, 2 H); $^{13}$C NMR (75 MHz, CDCl$_3$) −3.3 (2C), 23.8, 39.3, 63.6, 113.5, 128.6 (2C), 134.0 (2C), 134.7, 136.5, 139.5; HRMS (M-CH$_3$) calcd for C$_{12}$H$_{17}$OSi 205.1048, found 205.1045.

Preparation of 4-Allyldimethylsilylphenylacetic acid (2 Scheme 8).

To a solution 4-allyldimethylsilylphenethyl alcohol (1 Scheme 8, 2.8 g, 12.7 mmol) in acetone (60 mL) was added stock solution of oxidizing agent [mixed solution of CrO$_3$ (13 g), H$_2$SO$_4$ (11 mL), and water (40 mL)]. Upon addition of each potion of Jones reagent to the vigorously stirred reaction mixture, orange color of the solution rapidly changed to light green, and the end point was determined when the orange color persists. Acetone was carefully decanted from the flask and evaporated to leave an orange colored oil which was extracted with brine/ethyl acetate (1:4, 50 mL). The organic layer was dried (Na$_2$SO$_4$), concentrated, and the residue was purified by column chromatography (1:4 ethyl acetate/hexanes) to afford a colorless oil (2.1 g, 71%); $^1$H NMR (300 MHz, CDCl$_3$) δ 0.36 (s, 6 H), 1.84 (d, J=8.10 Hz, 2 H), 3.72 (s, 2 H), 4.92 (m, 1 H), 4.97 (m, 1 H), 5.86 (ddt, J 16.80, 10.35, 8.01 Hz, 1 H), 7.36 (d, J=7.98 Hz, 2 H), 7.58 (d, J=7.98 Hz, 2 H) 11.38 (bs, 1 H); $^{13}$C NMR (75 MHz, CDCl$_3$) −3.3 (2C), 23.7, 41.2, 113.6, 128.9 (2C), 134.0, 134.1 (2C), 134.6, 137.7, 178.3; HRMS (M-CH$_3$) calcd for C$_{12}$H$_{15}$O$_2$Si 219.0841, found 219.0846.

Preparation of (4S)-3-[2-(4-allyldimethylsilylphenyl)-1-oxoethyl]-4-benzyl-2-oxazolidinone (3 Scheme 8).

To a stirred solution of 4-allyldimethylsilylphenylacetic acid (2 Scheme 8, 5.7 g, 24.3 mmol) in THF (400 mL) at −78° C. was added triethylamine (4.4 mL, 31.5 mmol) followed by pivaloyl chloride (3.4 mL, 28 mmol). The mixture was stirred for 15 min at −78° C. and 1 h at room temperature and then re-cooled to −78° C. In a separate flask, (4S)-4-benzyl-2-oxazolidinone (5.2 g, 29.0 mmol) was dissolved in 20 mL of THF and cooled to −78° C. To this solution was added n-BuLi (2.5 M in hexanes, 11.6 mL, 29.0 mmol) via syringe and the solution was stirred for 30 min at −78° C. The metalated oxazolidinone was added via cannula to the white slurry prepared as described above and stirred for 30 min −78° C., then allowed to room temperature over 2 h. After quenching the reaction with 1 N aqueous sodium sulfate (100 mL) and evaporation of volatiles in vacuo, the residue was extracted with ethyl acetate (50×2 mL), dried (Na$_2$SO$_4$), and concentrated. The resulting oil was purified by column chromatography (1:5 ethyl acetate/hexanes) to afford a colorless oil (5.7 g, 54%); $^1$H NMR (300 MHz, CDCl$_3$) δ 0.37 (s, 6 H), 1.85 (d, J=8.01 Hz, 2 H), 2.85 (dd, J=13.40, 9.30 Hz, 1 H), 3.32 (dd, J=13.40, 3.27 Hz, 1 H), 4.21 (d, J=5.28 Hz, 2 H), 4.34 (d, J=15.80 Hz, 1 H), 4.43 (d, J=15.80 Hz, 1 H), 4.74 (m, 1 H), 4.92 (m, 1 H), 4.98 (m, 1 H), 5.87 (ddt, J=16.92, 10.11, 8.10 Hz, 1 H), 7.19–7.22 (2 H), 7.29–7.38 (3 H), 7.43 (d, J=7.74 Hz, 2 H), 7.60 (d, J=7.74 Hz, 2 H); $^{13}$C NMR (75 MHz, CDCl$_3$) −3.3 (2C), 23.8, 37.8, 41.7, 55.4, 66.2, 113.6, 127.4, 129.0 (2C), 129.3 (2C), 129.6 (2C), 134.1 (2C), 134.4, 134.7, 135.3, 153.5, 171.2; HRMS calcd for C$_{23}$H$_{27}$N$_1$O$_3$Si 393.1760, found 393.1755.

(2S,4S)-3-[2-azido-2-(4-allyldimethylsilylphenyl)-1-oxoethyl]-4-benzyl-2-oxazolidin (4 Scheme 8).

To a stirred solution of imidate (3 Scheme 8, 4.8 g, 12.2 mmol) in THF (300 mL) at −78° C. was added 0.5 M potassium bistrimethylsilylamide (29.4 mL, 14.6 mmol) via syringe. The resulting solution was stirred for 20 min at −78° C. to form the enolate. In a separate flask at −78° C., a solution of trisyl azide (5.7 g, 18.3 mmol) in THF (20 mL) was prepared and was transferred to the enolate solution via syringe. The solution was stirred for 2 min at −78° C. and then quenched by rapid addition of 2.2 mL of glacial acetic acid with immediate warming to 40° C. in water bath. After 1 h stirring, the reaction mixture was washed with brine (20 mL). The organic layer was separated and concentrated to leave a orange residue which was extracted with ethyl acetate and water. The organic layer was dried (Na$_2$SO$_4$), concentrated, and purified by column chromatography (1:5 ethyl acetate/hexanes) to afford a colorless oil (4.1 g, 77%); $^1$H NMR (300 MHz, CDCl$_3$) δ 0.33 (s, 6 H), 1.80 (d, J=8.10 Hz, 2 H), 2.90 (dd, J=13.42, 9.59 Hz, 1 H), 3.45 (dd, J=13.34, 3.13 Hz, 1 H), 4.12 (app t, J=8.50 Hz, 1 H), 4.19 (dd, J=9.24, 2.58 Hz, 1 H), 4.69 (m, 1 H), 4.88 (m, 1 H), 4.92 (m, 1 H), 5.80 (ddt, J=16.62, 10.35, 8.10 Hz, 1 H), 6.17 (s, 1 H), 7.26–7.42 (5 H), 7.46 (d, J=8.04 Hz, 2 H), 7.60 (d, J=8.04 Hz, 2 H); $^{13}$C NHR (75 MHz, CDCl$_3$) −3.4 (2C), 23.5, 37.7, 55.8, 63.7, 66.5, 113.8, 127.6, 127.8 (2C), 129.2 (2C), 129.5 (2C), 133.5, 134.3, 134.5 (2C), 134.9, 140.7, 152.5, 169.4; HRMS calcd for C$_{22}$H$_{23}$N$_4$O$_3$Si 419.1539, found 419.1534.

Methyl (2S)-azido-2-(4-allyldimethylsilylphenyl)acetate (5 Scheme 8).

To a solution of azidoimidate (4 Scheme 8, 3.0 g, 6.9 mmol) in MeOH (200 mL) was added titaniumisopropoxide (1.0 mL, 3.4 mmol), and the mixture was refluxed for 16 h. After cooling to room temperature, the reaction solution was filtered, and the filtrate was concentrated under reduced pressure. The residue was purified by column chromatography (1:5 ethyl acetate/hexanes) to afford a colorless oil (1.6 g, 82%); $^1$H NMR (300 Mz, CDCl$_3$) δ 0.29 (s, 6 H), 1.77 (dt, J=8.10, 1.15 Hz, 2 H), 3.78 (s, 3 H), 4.87 (t, J=1.15 Hz, 1 H), 4.87 (m, 1 H), 5.00 (s, 1 H), 5.80 (ddt, J=16.47, 10.6, 8.01 Hz, 1 H), 7.37 (d, J=7.83 Hz, 2 H), 7.57 (d, J=7.83 Hz, 2 H); $^{13}$C NMR (75 MHz, CDCl$_3$) −3.5 (2C), 23.5, 53.0, 65.3, 113.8, 126.9 (2C), 134.3, 14,4 (2C), 134.5, 140.4, 169.6; HRMS (M-CH$_3$) calcd for C$_{13}$H$_{16}$N$_3$O$_2$Si 274.1011, found 274.1011.

Preparation of Methyl (2S)-N-Boc-amido-2-(4-allyldimethylsilylphenyl)acetate (6 Scheme 8).

To a solution of methyl (2S)-azido-2-(4-allyldimethylsilylphenyl)acetate (5 Scheme 8, 400 mg, 1.38 mmol) in dry toluene (3 mL) under a N$_2$ atmosphere at 0° C. was added Me$_3$P (1.38 mL, 1.0 M in toluene). After 10 min stirring at room temperature, the flask was cooled to −20° C. and a solution of Boc-ON (340 mg, 1.38 mmol) in toluene (2 mL) was added via syringe. After further stirring for 1 h at room temperature, Et$_2$O (20 mL) and H$_2$O (5 mL) were added, then the two-phase solution was stirred for 10 min. The organic layer was separated, washed with water (10 mL), brine (10 mL), dried (Na$_2$SO$_4$), then concentrated. The residue was purified by column chromatography (1:7 ethyl acetate/hexanes) to afford a colorless oil (361 mg, 72%); $^1$H NMR (300 NMHz, CDCl$_3$) δ 0.27 (s, 6 H), 1.43 (s, 9 H), 1.74 (d, J=7.92 Hz, 2 H), 3.70 (s, 2 H), 4.83 (s, 1 H), 4.87 (d, J=7.26 Hz, 1 H), 5.75 (ddt, J=16.56, 10.08, 8.25 Hz, 1 H), 7.35 (d, J=7.95 Hz, 2 H), 7.50 (d, J=7.95 Hz, 1 H); $^{13}$C NMR (75 MHz, CDCl$_3$) −3.5 (2C), 23.6, 28.4 (3C), 52.7 57.6, 113.6, 126.5 (2C), 134.3 (2C), 134.4, 137.6, 139.1, 154.9, 171.6; HRMS (ES) calcd for C$_{19}$H$_{29}$NO$_4$Si 364.1939, found 364.1982.

Preparation of Resin (7 Scheme 8).

To a solution of methyl (2S)-N-Boc-amido-2-(4-allyldimethylsilylphenyl)acetate (6 Scheme 8, 728 mg, 2.0 mmol) in dry THF (7 mL) under a N$_2$ atmosphere was added 9-BBN (4.0 mL, 0.5 M solution in THF, 2.0 mmol) dropwise at 0° C. The mixture was gradually warmed to room temperature and stirred for 5 h. Pd(PPh$_3$)$_4$ (70 mg, 3 mol %), 4-bromopolystyrene (1.5 g, 1.94 mmol/g), 2 N aqueous Na$_2$CO$_3$ (2 mL, 4.0 mmol), and DMF (10 mL) were added. The reaction flask and reflux condenser were wrapped with aluminum foil, and the flask was refluxed for 24 h. Pd(PPh$_3$)$_4$ (70 mg, 3 mol %) was added to the reaction mixture and refluxing continued for 24 h. The resin was filtered and washed with THF (once), 1:1 THF/water (twice), water (twice), methanol (twice), CH$_2$Cl$_2$ (twice).

Preparation of 8 Scheme 8.

An aliquot of the resin prepared above (7 Scheme 8, 200mg) was treated with a solution of thioanisole (50 μL) and 50% TFA/$CH_2Cl_2$ (8 mL) for 5 min. The resin was washed with $CH_2Cl_2$ (8 mL×4), MeOH (8 mL×4), DMF (8 mL×4), and treated with benzoic acid (3.5 equiv.), EDC (3.5 equiv.), HOB·$TH_2O$ (3.5 equiv.), TEA (3.5 equiv.) in DMF (8 mL) for 20 h at room temperature. After successive washing with DMF, MeOH, $CH_2Cl_2$, the resin (200 mg) was treated with $Br$ (50 μL) in $CH_2Cl_2$ (7 mL) for 20 min. The cleavage solution was separated, and the resin was rinsed with $CH_2Cl_2$ (3 mL). Concentration of the combined filtrates gave a colorless oil (loading level 0.17 mmol/g, purity was determined to be higher than 95% based on the $^1$H NMR spectrum); $^1$H NMR (300 MHz, $CDCl_3$) δ 3.78 (s, 3 H), 5.72 (d, J=6.60 Hz, 1 H), 7.32 (d, J=8.40 Hz, 2 H), 7.40–7.55 (5 H), 7.81 (d, J=8.40 Hz, 2 H); $^{13}$C NMR (75 MHz, $CDCl_3$) 53.4, 56.5, 122.9, 127.4 (2C), 128.9 (2C), 129.2 (2C), 132.2, 132.3 (2C), 133.6, 135.9, 166.8, 171.3; HRMS (EI) calcd for $C_{16}H_{14}BrNO_3$ 347.0157 and 249.0136, found 247.0155 and 347.0148.

Preparation of (R)-(−)-N-[(4-allyldimethylsilylphenyl)methylene]-tert-butanesulfinamide (1 Scheme 9).

To a solution of (R)-(−)-tert-butanesulfinamide (3.7 g, 30 mmol) and 4-allyldimethylsilylbenzaldehyde (2 Scheme 1, 6.2 g, 30 mmol) in dry THF (15 mL) was added titanium(IV) propoxide (17 mL, 60 mmol). The mixture was refluxed for 1 h under a $N_2$ atmosphere. The mixture was cooled immediately upon reaction completion, and poured into a brine (30 mL) with rapid stirring. The resulting white suspension was filtered through a pad of celite, which was then washed with ethyl acetate (100 mL). The filtrate was transferred to a separatory funnel where the organic layer was washed with brine (20 mL). The organic layer was dried ($Na_2SO_4$), concentrated. The crude oil was purified by column chromatography (1:5 ethyl acetate/hexanes) to afford a colorless oil (6.3 g, 68%); $^1$H NMR (300 MHz, $CDCl_3$) δ 0.30 (s, 6 H), 1.26 (s, 9 H), 1.76 (d, J=7.92 Hz, 2 H), 4.83 (s, 1 H), 4.88 (d, J=4.41 Hz, 1 H), 5.74 (ddt, J=15.84, 9.27, 8.28 Hz, 1 H), 7.62 (d, J=7.92 Hz, 2 H), 7.82 (d, J=7.92 Hz, 2 H), 8.59 (s, 1 H); $^{13}$C NMR (75 MHz, $CDCl_3$) −3.5 (2C), 22.6 (3C), 23.4, 57.8, 113.9, 128.4 (2C),134.0, 134.2 (2C), 134.4, 144.6, 162.8; HRMS (M+1) calcd for $C_{16}H_{26}NOSSi$ 308.1505, found 308.1415.

Preparation of (R,S)-(−)-methyl N-(tert-butanesulfinyl)-3-amino-3-(4-allyldimethylsilyl)phenyl-propanoate (2 Scheme 9).

To a solution of methyl acetate (1.5 mL, 18.5 mmol) in dry THY (25 mL) at −78° C. was added lithium diisopropylamide (2 M solution, 9.8 mL, 19.6 mmol), and the solution was stirred for 15 min. Chlorotitanium triisopropoxide (10.1 mL, 39.3 mmol) in THF (20 mL) was added dropwise at −78° C. to form pale orange colored Ti enolate. After stirring for 30 min a solution of (R)-N-[(4-allyldimethylsilylphenyl)methylene]-tert-butanesulfinamide (1 Scheme 9, 3.8 mg, 12.3 mmol) in THF (10 mL) was added over a period of 20 min, and the reaction mixture was stirred for 3 h. Saturated $NH_4Cl$ (20 mL) was added slowly at −78° C., and the mixture was warmed to room temperature. Dilution of the mixture with water (10 mL)/EtOAc (100 mL) resulted in a white suspension which was filtered through a pad of Celite. The organic layer was concentrated, and the residue was extracted with EtOAc (40 mL)/brine (20 mL). Drying ($Na_2SO_4$) and concentration of the organic layer followed by column chromatography (1:1 ethyl acetate/hexanes) afforded a colorless oil (3.7 g, 79%); $^1$H NMR (300 MHz, $CDCl_3$) δ 0.26 (s, 6 H), 1.21 (s, 9 H), 1.73 (d, J=7.98 Hz, 2 H), 2.87 (d, J=5.64 Hz, 2 H), 3.64 (s, 3 H), 4.74 (bs, NH, 1 H), 4.80 (s, 1 H), 4.85 (m, 1 H), 5.74 (m, 1 H), 7.30 (d, J=7.41 Hz, 2 H), 7.47 (d, J=7.41 Hz, 2 H); $^{13}$C NMR (75 MHz, $CDCl_3$) −3.4 (2C), 22.7 (3C), 23.7, 41.9, 52.0, 55.6, 55.8, 113.5, 126.5 (2C), 134.0 (2C), 134.5, 138.4, 141.4, 171.7; HRMS calcd for $C_{19}H_{31}NO_3SSi$ 381.1795, found 381.1782.

Preparation of Mosher Amide (3 Scheme 9).

To a solution of (R,S)-(−)-methyl N-(tert-butanesulfinyl)-3-amino-3-(4-allyldimethylsilyl)phenylpropanoate (2 Scheme 9, 152 mg, 0.4 mmol) in MeOH (1 mL) was added 4 N HCl/dioxane (0.5 mL). After 5 min stirring, the solvent and HCl was removed under reduced pressure. To the crude amine solution in $CHCl_3$ (10 mL) was added pyridine (200 μL) followed by (R)-(−)-α-methoxy-α-(trifluoromethyl)-phenylacetic acid chloride (75 mg, 0.3 mmol). The reaction solution was stirred for 2 h at room temperature. The solvent and excess pyridine was removed, and the crude oil was diluted with EtOAc (25 mL), washed (0.5 N HCl and brine) then dried. The organic layer was concentrated to obtain MPTA amide derivative as a colorless oil (124 mg, 83% based on MTPACl); $^1$H NMR (300 MHz, $CDCl_3$) δ 0.27 (s, 6 H), 1.75 (d, J=8.07 Hz, 2 H), 2.84 (dd, J=9.90, 5.71 Hz, 1 H), 2.92 (dd, J=8.70, 6.75 Hz, 1 H), 3.40 (s, 3 H), 3.80 (s, 3 H), 4.84 (s, 1 H), 4.88 (m, 1 H), 5.46 (m, 1 H), 5.77 (ddt, J=16.53, 10.81, 8.10 Hz, 1 H), 7.30 (d, J=7.80 Hz, 2 H), 7.39–7.43 (3 H), 7.50 (d, J=7.80 Hz, 2 H), 7.54–7.58 (2 H), 7.76 (bd, J=8.73 Hz, 1 H); $^{13}$C NMR (75 MHz, $CDCl_3$) −3.3 (2C), 23.8, 28.1, 37.0, 39.8, 49.9, 52.1, 55.2, 113.7, 125.8 (2C), 128.0, 128.8(2C), 129.7(2C), 132.7, 134.4 (2C), 134.7, 138.6, 140,8, 143.1, 156.3, 166.0, 171.4; $^{19}$F NMR ($CDCl_3$) δ −69.15 (with $CFCl_3$ as an internal reference) Analysis of $^1$H NMR and $^{19}$F NMR integration showed less then 1% of the minor diastereomer. HRMS calcd for $C_{25}H_{30}NO_4F_3Si$ 493. 1897, found 493.1904.

Preparation of Resin 4 Scheme 9.

To a solution of (R,S)-(−)-methyl N-(tert-butanesulfinyl)-3-amino-3-(4-allyldimethylsilyl)phenylpropanoate (2 Scheme 9, 763 mg, 2 mmol) in dry THF (8 mL) under a $N_2$ atmosphere was added 9-BBN (4 mL, 0.5 M solution in THF, 2 mmol) dropwise at 0° C. The mixture was gradually warmed to room temperature and stirred for 5 h. $Pd(PPh_3)_4$ (70 mg), 4-bromopolystyrene (1.0 g, 1.94 mmol/g), 2 N aqueous $Na_2CO_3$ (2 mL, 4 mmol), DMF (10 mL), were added. The reaction flask and reflux condenser were wrapped with aluminum foil, and the mixture was refluxed for 24 h. $Pd(PPh_3)_4$ (70 mg) was added to the reaction mixture which was refluxed again for 24 h. The resin was filtered and washed with THF (once), 1:1 THF/water (twice), water (twice), methanol (twice), $CH_2Cl_2$ (twice), then dried under reduced pressure. An aliquot of the resin (200 mg) was treated with a solution of thioanisole (100 μL) and 50% TFA/$CH_2Cl_2$ (7 mL) for 5 min followed by washing with $CH_2Cl_2$ (8 mL×4). The resin was treated with a solution of $Br_2$ (150 μL) in $CH_2Cl_2$ (8 mL) for 20 min. The cleavage solution was filtered and the resin was rinsed with $CH_2Cl_2$ (3 mL). Concentration of the combined filtrates gave (3R)-methyl-3-amino-3-(4-bromophenyl)-butyrate (5 Scheme 9, 16.5 mg, loading level was determined to be 0.32 mequiv/g); $^1$H NMR (300 MHz, $CDCl_3$) δ 3.04 (dd, J=16.20, 6.30 Hz, 1 H), 3.35 (dd, J=16.20, 6.30 Hz, 1 H), 3.58 (s, 3 H), 4.82 (m, 1 H), 7.43–7.48 (4 H). HRMS cald for $C_{10}H_{12}BrNO_2$ 257.0051 and 259.0031, found 257.0053 and 259.0034.

Preparation of 2a Scheme 10.

An aliquot of the resin (4 Scheme 9, 800 mg, 0.32 mequiv/g, 0.26 mmol) was treated with a solution of thioanisole (200 μL) and 50% TFA/CH$_2$Cl$_2$ (18 mL) for 5 min. The resin was washed with CH$_2$Cl$_2$ (18 mL×4), DMF (18 mL×4), and treated with Fmoc-L-Ala-OH (3.5 equiv.), EDC (3.5 equiv.), HOBT·H$_2$O (3.5 equiv.), TEA (3.5 equiv.) in DMF (18 mL) for 16 h at room temperature. After successive washing with DMF, MeOH, CH$_2$Cl$_2$, and DMF, the resin was stirred in 20% piperidine/DMF (18 mL) for 30 min, then washed with DMF, MeOH, CH$_2$Cl$_2$, and DMF. Coupling of the N-terminal amino acid was performed with benzoic acid (3.5 equiv.), EDC (3.5 equiv.), HOB·TH$_2$O (3.5 equiv.), TEA (3.5 equiv.) in DMF (18 mL) for 16 h at room temperature. The resin was washed with DMF, MeOH, CH$_2$Cl$_2$, THF, and heated to reflux with LiOH (5 equiv.) in THF/H$_2$O (8:1, 20 mL) for 2.5 h. After washing with THF, H$_2$O, MeOH, CH$_2$Cl$_2$, DMF, the resin was treated with NH$_2$-Gly-OEt·HCl (3.5 equiv.), EDC (3.5 equiv.), HOB·TH$_2$O (3.5 equiv.), TEA (3.5 equiv.) in DMF (18 mL) for 16 h at room temperature. The resin was rinsed with DMF, 1:1 DMF/water, MeOH, CH$_2$Cl$_2$ and dried under reduced pressure. An aliquot of the resin (200 mg) was treated with CH$_2$C$_2$/TFA (1:1, 14 mL) for 24 h at room temperature. The cleavage solution was separated, and the resin was rinsed with CH$_2$Cl$_2$ (3 mL) and MeOH (5 mL). Concentration of the combined filtrates gave a white solid (24 mg, 88%, purity was determined to be higher than 95% based on the $^1$H NMR spectrum); $^1$H NMR (300 MHz, CDCl$_3$) δ 1.16 (t, J=7.16 Hz, 2 H), 1.42 (d, J=6.62 Hz, 3 H), 2.76 (m, J=2 H), 3.74 (m, 1 H), 4.01 (m, 1 H), 4.02 (q, J=7.16 Hz, 2 H), 4.74 (m, 1 H), 5.49 (m, 1 H), 7.20–7.76 (10 H), 7.77 (d, J=7.20 Hz, 2 H), 8.34 (d, J=7.51 Hz, 1 H); $^{13}$C NMR (75 MHz (75 MHz, CDCl$_3$) 14.1, 18.0, 41.6, 42.5, 50.1, 50.8, 61.9, 126.9 (2C), 127.5 (2C), 127.9, 128.7 (2C), 128.9 (2C) 132.2, 133.3, 140.4, 168.2, 170.5, 171.6, 173.0, HRMS (ES, M+1) calcd for C$_{23}$H$_{27}$N$_3$O$_5$ 426.2030, found 426.2024. Anal. calcd for C$_{23}$H$_{27}$N$_3$O$_5$: C, 64.93; H, 6.40; N, 9.88, found C, 64.74; H. 6.57; N, 9.76.

Preparation of 2b Scheme 10.

The same procedure as described for 2a Scheme 10 except that the cleavage of the final product was carried out with Br$_2$ (100 μL) in CH$_2$Cl$_2$ (8 mL) for 20 min. The cleavage solution was separated, and the resin was rinsed with CH$_2$Cl$_2$ (3 mL) and MeOH (5 mL). Concentration of the combined filtrates gave a white solid (30 mg, 94%, purity was determined to be higher than 95% based on the $^1$H NMR spectrum); $^1$H NMR (300 MHz, CD$_3$OD) δ 1.20 (t, J=7.08 Hz, 3 H), 1.42 (d, J=7.11 Hz, 3 H), 2.77 (dd, J=6.63, 2.37 Hz, 2 H), 3.82 (s, 2 H), 4.10 (q, J=7.08 Hz, 2 H), 4.56 (q, J=7.15 Hz, 1 H), 5.30 (t, J=6.89 Hz, 1 H), 7.26 (d, J=8.46 Hz, 2 H), 7.43–7.56 (5 H), 7.87 (d, J=6.87 Hz, 2 H); $^{13}$C NMR (75 MHz, CDCl$_3$) 14.4, 18.3, 41.9, 42.4, 51.9, 62.0, 122.3, 128.4 (2C), 128.6 (2C), 129.2 (2C), 131.1, 132.3 (2C), 133.6, 138.8, 169.1, 170.2, 172.6, 174.5; HRMS (ES, M+1) calcd for C$_{23}$H$_{27}$BrN$_3$O$_5$ 504.1135 and 506.1115, found 504,1153 and 506.1112. Anal. calcd for C$_{23}$H$_{26}$BrN$_3$O$_5$: C, 54.77; H, 5.20; N, 8.33, found C, 54.62; H, 5.14; N, 8.37.

Preparation of 2c Scheme 10.

The same procedure as described for 2a Scheme 10 except that the cleavage of the final product was carried out with ICl (150 mg) in CH$_2$Cl$_2$ (8 mL) for 20 min. The cleavage solution was separated, and the resin was rinsed with CH$_2$Cl$_2$ (3 mL) and MeOH (5 mL). Concentration of the combined filtrates gave a white powder (30 mg, 95%, purity was determined to be higher than 95% based on the $^1$H NMR spectrum); mp 181–185° C.; $^1$H NMR (300 MHz, CD$_3$OD) δ 1.19 (t, J=7.14 Hz, 3 H), 1.41 (d, J=7.05 Hz, 3 H), 2.77 (dd, J=6.72, 2.32 Hz, 2 H), 3.82 (s, 2 H), 4.09 (q, J=7.14 Hz, 2 H), 4.55 (q, J=7.17 Hz, 1 H), 5.29 (t, J=6.72 Hz, 1 H), 7.12 (d, J=8.13 Hz, 2 H), 7.44–7.57 (3 H), 7.65 (d, J=8.28 Hz, 2 H), 7.87 (d, J=6.99 Hz, 2 H), $^{13}$C NMR (75 MHz, DMSO-d$_6$) 14.7, 18.5, 41.3, 41.9, 49.7, 50.0, 61.1, 128.2 (2C), 128.8 (2C), 129.5 (2C), 131.9, 134.9, 137.5 (2C), 138.1, 143.2, 166.9, 170.3, 170.4, 172.1; HRMS (EI) calcd for C$_{23}$H$_{26}$IN$_3$O$_5$ 551.0919, found 551.0920. Anal. calcd for C$_{23}$H$_{26}$IN$_3$O$_5$: C, 50.10; H, 4.75; N, 7.62, found C, 50.29; H, 4.92; N, 7.50.

Preparation of 4-Allyldimethylsilylphenyacetaldehyde (9 Scheme 6).

To a suspension of pyridinium chlorochromate (1 Scheme 8, 8.6 g, 40 mmol) in dry CH$_2$Cl$_2$ (150 mL) was added 4-allyldimethylsilylphenethyl alcohol (4.4 g, 20 mmol) in one portion, and the mixture was stirred for 3 h at room temperature under a N$_2$ atmosphere. The reaction mixture was filtered through Celite and the combined solution of filtrate and washings (CH$_2$Cl$_2$) were concentrated and purified by column chromatography (1:10 ethyl acetate/hexanes) to afford a colorless oil (2.0 g, 46%); $^1$H NMR (300 MHz, CDCl$_3$) δ 0.34 (s, 6 H), 1.81 (d, J=8.40 Hz, 2 H), 3.72 (s, 2 H), 4.89 (s, 1 H), 4.93 (d, J=7.20 Hz, 1 H), H), 7.26 (d, J=7.80 Hz, 2 H), 7.57 (d, J=7.80 Hz, 2 H), 9.79. (s, 1 H); $^{13}$C NMR (75 CDCl$_3$) −3.2 (2C), 23.9, 50.8, 113.8, 129.3 (2C), 132.9, 134.6 (2C), 134.7, 138.0, 199.6.

Preparation of (R)-(−)-N-[(4-allyldimethylsilylphenyl) ethylene]-ter1-butanesulfinamide 1 Scheme 11).

To a solution of (R)-(−)-tert-butanesulfinamide (437 mg, 2 mmol) and 4-allyldimethylsilylphenylacetaldehyde (9 Scheme 6, 243 mg, 2 mmol) in dry THF (10 mL) was added titanium(IV) ethoxide (920 μL, 4 mmol). The mixture was refluxed for 30 min under a N$_2$ atmosphere. The mixture was cooled immediately upon completion of the reaction and poured into brine (5 mL) with rapid stirring. The resulting white suspension was filtered through a pad of Celite, which was then washed with ethyl acetate (40 mL). The filtrate was washed with brine (10 mL), and the organic layer was dried (Na$_2$SO$_4$) and concentrated. The crude oil was purified by column chromatography (1:6 ethyl acetate/hexanes) to afford a colorless oil (546 mg, 85%); $^1$H NMR (300 MHz, CDCl$_3$) δ 0.30 (s, 6 H), 1.22 (s, 9 H), 1.76 (d, J=8.40 Hz, 2 H), 3.84 (d, J=4.80 Hz, 2 H), 4.84 (s, 1 H), 4.89 (d, J=5.40 Hz, 1 H), 5.77 (m, 1 H), 7.24 (d, J=7.50 Hz, 2 H), 7.50 (d, J=7.50 Hz, 2 H), 8.14 (t, J=4.80 Hz, 1 H); $^{13}$C NMR (75 MHz, CDCl$_3$) −3.2, 22.7, 23.9, 42.9, 57.1, 113.8, 128.9, 134.5, 134.7, 135.8, 137.6, 167.6; HRMS (EI) calcd for C$_{17}$H$_{27}$NOSSi 321.1585, found 321.1582.

Preparation of (3R, 6S)-6-[4-dimethyl-(3-hydroxypropyl) silylbenzyl]-3-isopropyl-2,5-diethoxy-3,6-dihydropyrazine (1 Scheme 12).

To a solution of (3R, 6S)-6-(4-allyldimethylsilylbenzyl)-3-isopropyl-2,5-diethoxy-3,6-dihydropyrazine (2 Scheme 2, 820 mg, 2 mmol) in THF (3 mL) was added a solution of 9-BBN in THF (0.5 M, 4.0 mL, 2 mmol) at 0° C. After stirring the mixture for 16 h at room temperature, 2 N NaOH (3 mL, 6 mmol), 30% hydrogen peroxide (2 mL) were added, then the mixture was stirred further for 10 min. Ether (30 mL) was added, and the solution was stirred for 5 min. Brine (10 mL) was added to the reaction mixture and the organic layer was separated, dried (Na$_2$SO$_4$), and concentrated. The residue was purified by column chromatography (gradient of 1:3 to 1:2 ethyl acetate/hexanes) to afford a colorless oil (620 mg, 74%); $^1$H NMR (300 MHz, CDCl$_3$) δ 0.27 (s, 6 H), 0.65 (d, J=4.52 Hz, 3 H), 0.73 (m, 2 H), 0.95 (d, J=4.52 Hz, 3 H), 1.29 (t, J=7.08 Hz, 3 H), 1.35 (t, J=7.08 Hz, 3 H), 1.55 (m, 2 H), 1.90 (bs, OH, 1 H), 2.18 (dq, J=6.84, 3.18 Hz, 1 H), 3.09 (d, J=4.68 Hz, 2 H), 3.29 (t, J=3.39 Hz, 1 H), 3.53 (t, J=6.87 Hz, 2 H), 4.03–4.27 (4 H), 4.30 (q, J=4.47 Hz, 1 H), 7.13 (d, J=7.95 Hz, 2 H), 7.37 (d, J=7.95 Hz, 2 H); $^{13}$C NMR (75 MHz, CDCl$_3$) −3.0 (2C), 11.6, 14.5, 16.6, 19.1, 27.2, 31.4, 40.1, 56.7, 60.2, 60.6, 65.5, 129.6 (2C), 133.1 (2C), 136.4, 138.4, 162.2, 163.6. HRMS calcd for C$_{23}$H$_{38}$N$_2$O$_3$Si 418.2651, found 418.2642.

Preparation of Methyl (2S)-azido-2-[4-dimethyl-(3-hydroxypropyl)silylphenyl)acetate (2 Scheme 12).

To a solution of (2S)-azido-2-(4-allyldimethylsilylphenyl) acetate (5 Scheme 8, 640 mg, 2.2 mmol) in THF (3 mL) was added a solution of 9-BBN in THF (0.5 M, 4.4 mL, 2.2 mmol) at 0° C. After stirring the mixture for 16 h at room temperature, 2 N NaOH (3.3 mL, 6.6 mmol), 30% hydrogen peroxide (2.2 mL) were added, then the mixture was stirred further for 10 min. Ether (30 mL) was added, and the solution was stirred for 5 min. Brine (10 mL) was added to the reaction mixture and the organic layer was separated, dried (Na$_2$SO$_4$), and concentrated. The residue was purified by column chromatography (1:2 ethyl acetate/hexanes) to afford a colorless oil (470 mg, 70%); $^1$H NMR (300 MHz, CDCl$_3$) δ 0.29 (s, 6 H), 0.75 (m, 2 H), 1.55 (m, 2 H), 2.15 (s, OH, 1 H), 3.56 (t, J=6.77 Hz, 2 H), 3.76 (s, 3 H), 4.98 (s, 1 H), 7.36 (d, J=7.98 Hz, 2 H), 7.56 (d, J=7.98 Hz, 2 H); $^{13}$C NMR (75 MHz, CDCl$_3$) −3.1 (2C), 11.3, 27.0, 53.0, 65.5 126.9 (2C), 134.4 (2C), 134.5, 140.8, 169.7. HRMS calcd for C$_{14}$H$_{21}$N$_3$O$_3$Si 292.1117, found 292.1130.

Preparation of Resin (1 Scheme 13).

To a solution (4-allyldimethylsilyl)benzyl alcohol (3 Scheme 1, 2.1 g, 10 mmol) in dry THF (50 mL) under a N$_2$ atmosphere was added 9-BBN (20 mL, 0.5 M solution in THE, 10 mmol) dropwise at 0° C. The mixture was gradually warmed to room temperature and stirred for 5 h. Pd(PPh$_3$)$_4$ (70 mg), 4-bromopolystyrene (5.0 g, 1.94 mmol/g), 2 N aqueous Na$_2$CO$_3$ (10 mL, 20 mmol), DMF (20 mL), were added. The reaction flask and reflux condenser were wrapped with aluminum foil, and the mixture was refluxed for 24 h. Pd(PPh$_3$)$_4$ (70 mg) was added to the reaction mixture which was refluxed again for 24 h. The resin was filtered and washed with TUF (once), 1:1 THF/water (twice), water (twice), methanol (twice), CH$_2$Cl$_2$ (twice). The resin was used directly for the next reaction.

Preparation of the Polymer Bound (4-Alkyldimethylsilyl) benzyl Bromide (2 Scheme 13).

To the above described resin (1 Scheme 13, 3g) swelled in CH$_2$Cl$_2$ (120 mL) at 0° C. was added PPh$_3$ (2.6 g, 10 mmol) and CBr$_4$ (3.3 g, 10 mmol), and the reaction mixture was stirred for 4 h at 0° C. The resin was filtered and washed with CH$_2$Cl$_2$ (twice), methanol (twice), 1:1 methanol/water (twice), methanol (twice), CH$_2$Cl$_2$ (twice), then dried under reduced pressure. An aliquot of the resin (200 mg) was treated with a solution of CH$_2$Cl$_2$ (7 mL) and Br$_2$ (150 μL) for 5 min. The cleavage solution was removed, and the resin was rinsed with CH$_2$Cl$_2$ (3 mL) Concentration of the combined filtrates gave the known 4-bromobenzyl bromide (3 Scheme 3, 18.5 mg, 0.37 mequiv/g, purity was determined to be higher than 95% based on the $^1$H NMR spectrum).

Preparation of Resin (1 Scheme 14).

To the aliquot of resin (1 Scheme 13, 150 mg) swelled in THF (7 mL) were added 4-hydroxybenzaldehyde (122 mg, 1.0 mmol), triphenylphosphine (263 mg, 1 mmol) and DEAD (160 μL, 1 mmol). The reaction mixture was agitated for 16 h at room temperature, then washed with CH$_2$Cl$_2$ (twice), methanol (twice), CH$_2$Cl$_2$ (twice). To the resin swelled in CH$_2$Cl$_2$ (7 mL) was added Br$_2$ (50 μL), and the mixture was stirred for 10 min at room temperature. Filtration of the cleavage solution from the resin followed by evaporation yielded ethyl 4-(4-bromobenzyloxy) benzaldehyde (2 Scheme 14, 11.0 mg); $^1$H NMR (300 MHz, CDCl$_3$) δ 5.09 (s, 2 H), 7.05 (d, J=8.70 Hz, 2 H), 7.30 (d, J=8.10 Hz, 2 H), 7.52 (d, J=8.40 Hz, 2 H), 7.84 (d, J=8.40 Hz, 2H), 9.88(s,2 H).

Preparation of 4-(4-Allyldimethylsilylbenzyloxy)benzyl Alcohol (3 Scheme 14).

A solution of 4-allyldimethylsilylbenzyl bromide (4 Scheme 13, 2.7 g, 10 mmol), 4-hydroxybenzyl alcohol (12.5 g, 10 mmol), tetrabutylammonium iodide (100 mg) and powdered K$_2$CO$_3$ (2.1 g, 15 mmol) in acetone (60 mL) was stirred at 60° C. for 22 h. The precipitated sol was filtered and the filtrate was concentrated. The crude oil was purified by column chromatography (1:3 ethyl acetate/hexanes) to afford a colorless oil (2.9 g, 94%); $^1$H NMR (300 MHz, CDCl$_3$) δ 0.37 (s, 6 H), 1.84 (d, J=6.30 Hz, 2 H), 2.72 (s, OH, 1 H), 4.58 (s, 2 H), 4.93 (s, 1 H), 4.97 (m, 2 H), 5.09 (s, 1 H), 5.86 (ddt, J=16.80 Hz, 10.50, 8.10 Hz, 1 H), 7.01 (d, J=8.40 Hz, 2 H), 7.30 (d, J=8.40 Hz, 2 H), 7.48 (d, J=7.90 Hz, 2 H), 7.61 (d, J=7.90 Hz, 2 H); $^{13}$C NMR (75 MHz, CDCl$_3$) −3.1 (2 C), 24.0, 65.0, 70.2, 113.9, 115.2 (2 C), 127.1 (2 C), 128.9 (2 C), 133.8, 134.2 (2 C), 134.8, 138.1, 138.7, 158.6. HRMS (EI) calcd for C$_{19}$H$_{24}$O$_2$Si 312.1545, found 312.1547.

Preparation of Resin (4 Scheme 14).

To a solution 4-(4-allyldimethylsilylbenzyloxy)benzyl alcohol (3 Scheme 14, 1.3 g, 4.2 mmol) in dry THF (30 mL) under a N$_2$ atmosphere was added 9-BBN (8.4 mL, 0.5 M solution in THF, 4.2 mmol) dropwise at 0° C. The mixture was gradually warmed to room temperature and stirred for 5 h. Pd(PPh$_3$)$_4$ (70 mg), 4-bromopolystyrene (2.0 g, 1.94 mmol/g), 2 N aqueous Na$_2$CO$_3$ (4.2 mL, 8.4 mmol), DMF (10 mL), were added. The reaction flask and reflux condenser were wrapped with aluminum foil, and the mixture was heated to 65° C. for 24 h. Pd(PPh$_3$)$_4$ (70 mg) was added to the reaction mixture which was heated to 65° C. for 24 h. The resin was filtered and washed with THF (once), 1:1 THF/water (twice), water (twice), methanol (twice), CH$_2$Cl$_2$ (twice). The resin was used directly for the next reaction.

Preparation of Resin (5 Scheme 14).

To the resin (4 Scheme 14, 1 g) swelled in CH$_2$Cl$_2$ (20 mL) at 0° C. was added PPh$_3$ (1.3 g, 5 mmol) and CBr$_4$ (1.7 g, 5 mmol), and the reaction mixture was stirred for 4 h at 0° C. The resin was filtered and washed with CH$_2$Cl$_2$ (twice), methanol (twice), 1:1 methanol/water (twice), methanol (twice), CH$_2$Cl$_2$ (twice), then dried under reduced pressure.

Preparation (1 Scheme 16).

To a stirred mixture of 4-allyldimethylsilylbenzylalcohol (413 mg, 2 mmol), N-Boc-ethyl oxamate (478 mg, 2.2 mmol), triphenylphosphine (577 mg, 2.2 mmol) in dry THE (15 mL) was added diethyl azodicarboxylate (350 μL, 2.2 mmol). After being stirred for 1 h at room temperature, the reaction mixture was concentrated, and the residue was triturated with 1:6 ethyl acetate/hexanes. The precipitated triphenylphosphine oxide was filtered. The filtrate was concentrated, and the residue was purified on silica gel with 1:6 ethyl acetate/hexanes to afford a colorless oil (722 mg, 89%); $^1$H NMR (300 MHz, CDCl$_3$) δ 0.27 (s, 2 H), 1.36 (t, J=7.50 Hz, 3 H), 1.43 (s, 9 H), 1.73 (d, J=8.40 Hz, 2 H), 4.35 (q, J=7.50 Hz, 2 H), 4.80–4.87 (4 H), 5.74 (m, 1 H), 7.29 (d, J=7.50 Hz, 2 H), 7.47 (d, J=7.50 Hz, 2 H); $^{13}$C NMR (75 MHz, CDCl$_3$) −3.3, 14.0, 23.9, 27.9, 46.4, 62.4, 85.6, 113.6, 127.0, 127.7, 133.7, 134.5, 134.9, 137.4, 151.8, 162.0, 163.6; HRMS (EI) calcd for C$_{21}$H$_{31}$NO$_5$Si 405.1973, found 405.1972.

Preparation of N-Boc-4-allyldimethylsilylbenzylamine (2 Scheme 16).

The oxamate derivative obtained above (1 Scheme 16, 406 mg, 1 mmol) was vigorously stirred in a heterogeneous solution of LiOH (210 mg, 5 mmol) in THF/H$_2$O (4:1, 25 mL) for 2 h. The reaction mixture was diluted with H$_2$O (30 mL) and extracted with methylene chloride (40 mL). The organic layer was dried (Na$_2$SO$_4$) and concentrated in vacuo to leave a colorless oil (287 mg, 94%); $^1$H NMR (300 MHz, CDCl$_3$) δ 0.30 (s, 6 H), 1.47 (s, 9 H), 1.76 (d, J=7.83 Hz, 2 H), 4.28 (d, J=6.02 Hz, 2 H), 4.86 (s, 1 H), 4.90 (d, J=6.61 Hz), 5.31 (bs, NH, 1 H), 5.78 (ddt, J=16.53, 10.23, 8.14 Hz, 1 H), 7.27 (d, J 7.86 Hz, 2 H), 7.49 (d, J=7.86 Hz, 2 H); $^{13}$C NMR (75 MHz, CDCl$_3$) −3.2 (2C), 23.9, 28.7 (3C), 44.8, 79.4, 113.7, 127.1 (2C), 134.1 (2C), 134.7, 137.5, 140.3, 156.3; HRMS (EI) calcd for C$_{17}$H$_{27}$NO$_2$Si 305.1811, found 305.1795.

Preparation of Resin (3 Scheme 16).

To a solution of N-Boc-4-allyldimethylsilylbenzylamine (2 Scheme 16, 611 mg, 2 mmol) in dry THF (4 mL) under a N$_2$ atmosphere was added 9-BBN (4 mL, 0.5 M solution in THF, 2 mmol) dropwise at 0° C. The mixture was gradually warmed to room temperature and stirred for 2 h. THF was evaporated under reduced pressure and the reaction intermediate was dissolved in toluene (8 mL). After adding ground K$_3$PO$_4$ (424 mg, 4 mmol), 4-bromopolystyrene (1.0 g, 1.94 mmol/g), Pd(PPh$_3$)$_4$ (70 mg), the reaction mixture was degassed by bubbling with N$_2$ and sealed. The reaction flask was wrapped with aluminum foil and heated at 80° C. for 24 h. The resin was filtered and washed with MeOH (once), 1:1 MeOH/water (twice), water (twice), methanol (twice), CH$_2$Cl$_2$ (twice), then dried under reduced pressure.

Preparation of Dipeptide Analog (5 Scheme 16).

An aliquot of the resin prepared above (500 mg) was treated with a solution of thioanisole (100 μL) and 50% TFA/CH$_2$Cl$_2$ (7 mL) for 5 min followed by washing with CH$_2$Cl$_2$ (8 mL×4). The resin was further washed with DMF (8 mL×4), and treated with Fmoc-β-Ala-OH (312 mg, 1 mmol), EDC (192 mg, 1 mmol), HOBT·H$_2$O (135 mg, 1 mmol), TEA (140 mL, 1 mmol) in DMF (8 mL) for 15 h at room temperature and washed. The loading level of dried resin (4 Scheme 16) determined by Fmoc release UV/VIS assay was 0.1 mmole/g. The resin was stirred in 20% piperidine/DMF (8 mL) for 20 min, then washed with DMF, MeOH, CH$_2$Cl$_2$, and DMF. Peptide coupling of the resin bound amine was performed with butyric acid (91 mL, 1 mmol), EDC (1 mmol), HOBT·H$_2$O (1 mmol), TEA (1 mmol) in DMF (8 mL) for 16 h at room temperature. After washing with DMF, MeOH/H$_2$O, MeOH, CH$_2$Cl$_2$, and drying, a portion of the resin (250 mg) was treated with a solution of Br$_2$ (100 μL) in CH$_2$Cl$_2$ (8 mL) for 20 min. The cleavage solution was filtered and the resin was rinsed with CH$_2$Cl$_2$ (3 mL). Concentration of the combined filtrates gave an orange powder (5 Scheme 16, 11.5 mg, 92%, purity was determined to be higher than 95% based on the $^1$H NMR spectrum); $^1$H NMR (500 MHz, CDCl$_3$) δ 1.03 (t, J=7.25 Hz, 3 H), 1.78 (app q, J=7.25 Hz, 2 H), 2.57 (t, J=7.25 Hz, 2 H 3.21 (bs, 2 H), 3.71 (bs, 2 H), 4.53 (d, J=4 Hz, 2 H), 7.29 (d, J=8.00 Hz, 2 H), 7.51 (d, J=8.00 Hz, 2 H); $^{13}$C NMR (125 MHz, CDCl$_3$) 13.9, 19.3, 35.9, 37.0, 45.1, 122.6, 130.5, 132.3, 134.3, 176.0, 180.4;. HRMS calcd for C$_{14}$H$_{19}$BrN$_2$O$_2$ 326.0630 and 328.0609, found 326.0630 and 328.0625.

Preparation of Secondary Amine (2 Scheme 17).

To the aliquot of resin (2 Scheme 13, 200 mg) swelled in DMF (7 mL) was added phenethylamine (185 μL, 20 equiv). The reaction mixture was agitated for 16 h at room temperature, then washed with DMF (twice), water (twice), methanol (twice), CH$_2$Cl$_2$ (twice). To the resin swelled in CH$_2$Cl$_2$ (7 mL) was added Br$_2$ (100 μL), and the mixture was stirred for 10 min at room temperature. Filtration of the cleavage solution from the resin followed by evaporation yielded N-(4-bromobenzyl)-N-phenethylamine (2 Scheme 17, 18 mg); $^1$H NM (300 MHz, DMSO-6) δ 2.95 (m, 2 H), 3.13 (m, 2 H), 4.18 (m, 2 H), 7.21–7.36(5 H), 7.49 (d, J=8.40 Hz, 2 H), 7.65 (d, J=8.40 Hz, 2 H).

Preparation of N-(4-methylphenyl)sulfonyl)-N-(2-phenylethyl)-4-bromobenzylamine Using the Polymer Bound (4-Alkyldimethylsilyl)benzyl Bromide (3 Scheme 17).

To the aliquot of resin (2 Scheme 13, 150 mg, 0.37 mequiv/g) swelled in DMF (7 mL) was added phenethylamine (10 equiv). The reaction mixture was agitated for 16 h at room temperature, then washed with DMF (twice), water (twice), methanol (twice), CH$_2$Cl$_2$ (twice). To the resin swelled in CH$_2$Cl$_2$ (7 mL) were added p-toluenesulfonyl chloride (10 equiv), TEA (10 equiv) and catalytic amount of DMAP. After agitation for 20 h at room temperature the resin was washed with CH$_2$Cl$_2$ (twice), methanol (twice), CH$_2$Cl$_2$ (twice). To the resin swelled in CH$_2$Cl$_2$ (7 mL) was added Br$_2$ (100 μL), and the mixture was stirred for 10 min at room temperature. Filtration of the cleavage solution from the resin followed by evaporation yielded the title compound (3 Scheme 17, 22 mg, 89%); $^1$H NMR (300 MHz, CDCl$_3$) δ 2.46 (s, 3 H), 2.65 (t, J=8.07 Hz, 2 H), 3.31 (t, J=8.04 Hz, 2 H), 4.29 (s, 2 H), 6.98 (d, J=7.80 Hz, 2 H 7.15–7.27(5 H), 7.33 (d, J=8.07 Hz, 2 H), 7.45 (d, J=8.34 Hz, 2 H), 7.74 (d, J=8.28 Hz, 2 H); $^{13}$C NMR (75 MHz, CDCl$_3$) 35.3, 49.9, 51.8, 121.8, 126.7, 127.3 (2C), 128.7 (2C), 128.8 (2C), 130.2 (2C), 130.3 (2C), 131.8 (2C), 136.0, 136.9, 138.4, 143.8.

Preparation of N-hydroxy-α-[[(4-methylphenyl)sulfonyl](4-bromobenzyl)amino] Acetamide Using the Polymer Bound (4-alkyldimethylsilyl)benzyl Bromide (4 Scheme 17).

To the aliquot of resin (2 Scheme 13, 150 mg, 0.37 mequiv/g) swelled in DMF (7 mL) were added glycine ethyl ester hydrochloride(10 equiv) and DIPEA (10 equiv). The reaction mixture was agitated for 16 h at room temperature, then washed with DMF (twice), water (twice), methanol (twice), CH$_2$Cl$_2$ (twice). To the resin swelled in CH$_2$Cl$_2$ (7 mL) were added p-toluenesulfonyl chloride (10 equiv), TEA (10 equiv) DMAP (cat). After agitation for 20 h at room temperature the resin was washed with CH$_2$Cl$_2$ (twice), methanol (twice), CH$_2$Cl$_2$ (twice). To the resin swelled in CH$_2$Cl$_2$ (7 mL) was added Br$_2$ (100 μL), and the mixture was stirred for 10 min at room temperature. Filtration of the cleavage solution from the resin followed by evaporation yielded the title compound (4 Scheme 17, 21 mg, 87%); $^1$H NMR (300 MHz, CDCl$_3$) δ 1.15 (t, J=7.05 Hz, 3 H), 2.44 (s, 3 H), 3.65 (bs, 2 H), 3.72 (q, J=7.05 Hz 2 H), 4.31 (bs, 2 H), 7.16 (d, J=8.40 Hz, 2 H), 7.34 (d, J=7.80 Hz, 2 H), 7.44 (d, J=8.40 Hz, 2 H), 7.72 (d, J=7.80 Hz, H); $^{13}$C NMR (75 MHz, CDCl$_3$) 13.5, 21.8, 49.8, 53.5, 72.5, 122.7, 127.7 (2C), 130.3 (2C), 130.9 (2C), 132.3 (2C), 133.9, 134.8, 144.7, 169.6.

Preparation of 2-(4-Bromophenyl)-1,3-dioxolane (2 Scheme 18).

A mixture of 4-bromobenzaldehyde (1 Scheme 18, 9.5 g, 51.4 mmol) and ethylene glycol (6.4 g, 113 mmol) and p-toluenesulfonic acid (120 mg) in benzene (200 mL) was refluxed in a Dean Stark apparatus for 4 h. The reaction mixture was cooled to room temperature, and the solution was extracted with cold water/ethyl acetate. The organic layer was washed with brine, dried (Na$_2$SO$_4$), and concentrated to give a colorless oil (11.4, 95%); $^1$H NMR (300 MHz, CDCl$_3$) δ 4.01–4.14 (4 H), 5.78 (s, 1 H), 7.37 (d, J=8.34 Hz, 2 H), 7.53 (d, J=8.34 Hz, 2 H); HRMS (EI) calcd for C$_9$H$_9$BrO$_2$ 227.9786, 229.9766, found 227.9771, 229.9754.

Preparation of 2-(4-Allyldimethylsilylphenyl)1,3-dioxolane (3 Scheme 18).

To a solution of 2-(4-bromophenyl)-1,3-dioxolane (2 Scheme 18, 6.0 g, 26.2 mmol) in dried THF (200 mL) at −78° C. was added t-butyllithium (15.4 mL, 1.7 M solution in pentane, 26.2 mmol) over a period of 5 min. After 30 min of further stirring at −78° C., allylchlorodimethylsilane (3.7 g, 27.5 mmol) in THF (20 mL) was added dropwise over a period of 10 min. The reaction mixture was stirred for 1 h and warmed to room temperature. THF was removed under reduced pressure, and the residue was extracted with cold water/ethyl acetate. The organic layer was washed with brine, dried ($Na_2SO_4$), and concentrated to give a colorless oil (5.4 g, 91%); $^1$H NMR (300 MHz, $CDCl_3$) δ 0.31 (s, 6 H), 1.78 (d, J=7.95 Hz, 2 H), 4.02–4.18 (4 H), 4.85 (s, 1 H), 4.90 (m, 1 H), 5.78 (m, 1 H), 5.85 (s, 1 H), 7.50 (d, J=7.95 Hz, 2 H), 7.58 (d, J=7.95 Hz, 2 H); $^{13}$C NMR (75 MHz, $CDCl_3$) −3.4 (2C), 23.7, 65.4 (2C), 103.7, 113.6, 125.8 (2C), 133.8 (2C), 134.6, 138.8, 139.9; HRMS calcd for $C_{14}H_{20}O_2Si$ 248.1233, found 248.1230.

Preparation of Resin (4 Scheme 18).

To a solution 2-(4-allyldimethylsilylphenyl)-1,3-dioxolane (3 Scheme 18, 456 mg, 2 mmol) in dry THF (10 mL) under a $N_2$ atmosphere was added 9-BBN (4 mL, 0.5 M solution in THF, 2 mmol) dropwise at 0° C. The mixture was gradually warmed to room temperature and stirred for 5 h. $Pd(PPh_3)_4$ (70 mg), 4-bromopolystyrene (500 mg, 1.94 mmol/g), 2 N aqueous $Na_2CO_3$ (2 mL, 4 mmol), DMF (5 mL), were added. The reaction flask and reflux condenser were wrapped with aluminum foil, and the mixture was refluxed for 24 h. $Pd(PPh_3)_4$ (70 mg) was added to the reaction mixture which was refluxed again for 24 h. The resin was filtered and washed with THF (once), 1:1 THF/water (twice), water (twice), methanol (twice), $CH_2Cl_2$ (twice), then dried under reduced pressure. The resin (4 Scheme 18) was agitated in THF/1 N HCl (8:1) for 16 h at 30° C. After washing and drying, an aliquot of the resin (200 mg) was treated with a solution of $CH_2Cl_2$ (7 mL) and $Br_2$ (150 μL) for 5 min. The cleavage solution was removed, and the resin was rinsed with $CH_2Cl_2$ (3 mL). Concentration of the combined filtrates gave the known 4-bromobenzaldehyde (1 Scheme 18, 11 mg, loading level was determined to be 0.30 mequiv/g); $^1$H NMR (300 MHz, $CDCl_3$) δ 7.71 (d, J=8.30 Hz, 2 H), 7.77 (d, J=8.30 Hz, 2 H), 10.00 (s, 1 H).

Preparation of 4-Bromo-α-methyl Benzyl Bromide (7 Scheme 18).

To a 50 mL round-bottomed flask containing polystyrene resin (5 Scheme 18, 200 mg, 0.30 mequiv/g) in dry THF (15 mL) at −78° C. was added methylmagnesium bromide (10 equiv). The reaction slurry was stirred for 1 h at −78° C., then warmed slowly to room temperature and further stirred for 2 h. After cooling the flask to −20° C., saturated $NH_4Cl$ (0.5 mL) was added, and the mixture was stirred for 20 min at room temperature. The resin was filtered and washed with 1:1 THF/water (twice), water (twice), methanol (twice), $CH_2Cl_2$ (twice), then dried under reduced pressure. To a slurry of resin in $CH_2Cl_2$ (8 mL) was added $Br_2$ (100 μL). After agitation for 20 min, the cleavage solution was removed, and the resin was rinsed with $CH_2Cl_2$ (5 mL). Concentration of the combined filtrates gave 4-bromo-α-methyl benzyl bromide (7 Scheme 18) as a colorless oil (12 mg, 75%); $^1$H NMR (300 MHz, $CDCl_3$) δ 2.03 (d, J=6.97 Hz, 3 H), 5.17 (q, J=6.97 Hz, 1 H), 7.32 (d, J=8.49 Hz, 2 H), 7.49 (d, J=8.49 Hz, 2 H); $^{13}$C NMR (75 MHz, $CDCl_3$) 27.0, 48.5, 122.4, 128.8 (2C), 132.1 (2C), 142.5.

Preparation of 2-(4-Bromophenyl)-2-methyl-1,3-dioxolane (2 Scheme 19).

A mixture of 4-bromoacetophenone (1 Scheme 19, 20.0 g, 0.1 mol) and ethylene glycol (12.5 g, 0.2 mol) and p-toluenesulfonic acid (200 mg) in benzene (400 mL) was refluxed in a Dean Stark apparatus for 6 h. The reaction mixture was cooled to room temperature, and the solution was extracted with $H_2O$/ethyl acetate. The organic layer was washed with brine, dried ($Na_2SO_4$), and concentrated to give a colorless oil (23 g, 96%); $^1$H NMR (300 MHz, $CDCl_3$) δ 1.63 (s, 3 H), 3.76 (m, 2 H), 4.04 (m, 2 H), 7.37 (d, J=8.40 Hz, 2 H), 7.47 (d, J=8.40 Hz, 2 H); $^{13}$C NMR (75 MHz, $CDCl_3$) 27.6, 64.5 (2C), 108.4, 121.9, 127.2 (2C), 131.4 (2C), 142.5

Preparation of 2-(4-Allyldimethylsilylphenyl)-2-methyl-1,3-dioxolane (3 Scheme 19).

To a solution of 2-(4-bromophenyl)-2-methyl-1,3-dioxolane (22, 22.0 g, 90 mmol) in dried THF (600 mL) at −78° C. was added t-butyllithium (53.0 mL, 1.7 M solution in pentane, 90 mmol) over a period of 15 min. After 30 min of further stirring at −78° C., allylchlorodimethylsilane (12.2 g, 90 mmol) in THF (40 mL) was added dropwise over a period of 20 min. The reaction mixture was stirred for 1 h and warmed to room temperature. THF was removed under reduced pressure, and the residue was extracted with $H_2$/ethyl acetate. The organic layer was washed with brine, dried ($Na_2SO_4$), and concentrated to give a colorless oil (19.8 g, 91%); $^1$H NMR (300 MHz, $CDCl_3$) δ 0.30 (s, 6 H), 1.68 (s, 3 H), 1.77 (d, J=8.01 Hz, 2 H), 3.80 (m, 2 H), 4.06 (m, 2 H), 4.86 (m, 1 H), 4.90 (m, 1 H), 5.80 (ddt, J=16.89, 10.23, 8.07 Hz, 1 H), 7.47–7.52 (4 H)); $^{13}$C NMR (75 MHz, $CDCl_3$) −3.3 (2C), 23.7, 27.6, 64.5 (2C), 108.8, 113.5, 124.6 (2C), 133.6 (2C), 134.6, 138.2, 144.1.

Preparation of 4-Allyldimethylsilylacetophenone.

A mixture of 2-(4-allyldimethylsilylphenyl)-2-methyl-1,3-dioxolane (3 Scheme 19, 18 g, 74 mmol) and p-toluenesulfonic acid (200 mg) in acetone (300 mL) was heated under reflux for 3 h. The solution was concentrated under reduced pressure, and acetone (300 mL) was added to the residue. After refluxing for 3 h, the solution was concentrated, and the crude oil was purified by silica gel chromatography (1:4 ethyl acetate/hexanes) to afford a colorless oil (15.4 g, 95%); $^1$H NMR (300 MHz, $CDCl_3$) δ 0.32 (s, 6 H), 1.78 (d, J=7.92 Hz, 2 H), 2.61 (s, 3 H), 4.84 (s, 1 H), 4.89 (m, 1 H), 7.63 (d, J=7.98 Hz, 2 H), 7.93 (d, J=7.98 Hz, 2 H).

Preparation of 4-Allyldimethylsilyl-α-methyl Benzyl Alcohol (4 Scheme 19).

To a solution of 4-allyldimethylsilylacetophenone (15.0 g, 68.7 mmol) in ethyl alcohol (300 mL) at 0° C. was added sodium borohydride (1.6 g, 41.2 mmol). The reaction mixture was stirred for 2 h at 0° C. and warmed to room temperature, then stirred further for 3 h. Ethyl alcohol was removed under reduced pressure, and the residue was extracted with $H_2O$/ethyl acetate. The organic layer was dried ($Na_2SO_4$), concentrated, purified by silica. gel chromatography (1:5 ethyl acetate/hexanes) to afford a colorless oil (13.5 g, 89%); $^1$H NMR (300 MHz, $CDCl_3$) δ 0.29(s, 6 H), 1.50 (d, J=6.60 Hz, 3 H), 1.76 (dt, J=8.10, 1.27 Hz, 2 H), 4.84–4.92 (3 H), 5.79 (ddt, J=16.80, 10.20, 8.10 Hz, 1 H), 7.37 (d, J=7.80 Hz, 2 H), 7.51 (d, J=7.80 H Hz, 2 H)); $^{13}$C NMR (75 MHz, $CDCl_3$) −3.3 (2C), 23.9, 25.2, 70.2, 113.6, 125.0 (2C), 133.9 (2C), 134.7, 137.6, 146.8.

Preparation of Resin (6 Scheme 18).

To a solution 4-allyldimethylsilyl-α-methyl benzyl alcohol (4 Scheme 19, 2.2 g, 10 mmol) in dry THF (20 mL) under a $N_2$ atmosphere was added 9-BBN (20 mL, 0.5 M solution in THF, 10 mmol) dropwise at 0° C. The mixture was gradually warmed to room temperature and stirred for 5 h. Pd(PPh$_3$)$_4$ (70 mg), 4-bromopolystyrene (3.0 g, 1.94 mmol/g), 2 N aqueous Na$_2$CO$_3$ (5 mL, 10 mmol), DMF (20 mL), were added. The reaction flask and reflux condenser were wrapped with aluminum foil, and the mixture was refluxed for 24 h. Pd(PPh$_3$)$_4$ (70 mg) was added to the reaction mixture which was refluxed again for 24 h. The resin was filtered and washed with THF (once), 1:1 THF/water (twice), water (twice), methanol (twice), CH$_2$Cl$_2$ (twice), then dried under reduced pressure.

Preparation of Resin (1 Scheme 20).

To a solution 4-allyldimethylsilylphenylacetic acid (2 Scheme 8, 470 mg, 2 mmol) in dry THF (4 mL) was added 9-BBN (4 mL, 0.5 M solution in THF, 2 mmol) dropwise at 0° C. The mixture was gradually warmed to room temperature and stirred for 6 h. Pd(PPh$_3$)$_4$ (120 mg, 5 mol %), 4-bromopolystyrene (2 g, 1.94 mmol/g,), 2 N aqueous Na$_2$CO$_3$ (2 mL, 4 mmol), were added. The reaction mixture was stirred for 48 h at 70° C. under N$_2$ atmosphere. The resin was washed with THF (1×), methanol (2×), water (2×), methanol (2×) and dried under vacuum. The loading level of the resin, as determined by the mass balance of the 4-bromophenylacetic acid which was obtained by treating a sample of resin with Br$_2$ in dichloromethane for 20 min, was found to be 0.14 mmol/g.

Preparation of Methyl 4-Allyldimethylsilylbenzoate (3 Scheme 20).

To a suspension of activated magnesium turning (490 mg, 20 mmol) in dry TKF (20 mL) were added a piece of I$_2$ and ethyl iodide (50 μL). The reaction mixture was heated to reflux until the red color disappeared. Heating (65° C.) of the suspension was continued while a solution of 1-allyldimethylsilyl-4-bromobnezene (1 Scheme 1, 2.6 g, 10 mmol) in THF (20 mL) was added over a period of 15 min. Upon completion of the addition, the gray solution was heated further for 20 min. After the reaction was cooled to room temperature, anhydrous CO$_2$ was gently bubbled through the reaction mixture for 5 min and stirred further for 10 min. The clear solution was poured into a saturated NH$_4$Cl (10 mL) with vigorous stirring, and the suspension was filtered through a short pad of Celite. The solution was diluted with ethyl acetate (20 mL), and the organic layer was separated, dried over Na$_2$SO$_4$ and concentrated to leave a white solid (2 Scheme 20) on standing. Without further purification, the solid was dissolved in MeOH (40 mL), and the solution was treated with a catalytic amount of thionyl chloride (50 μL), then stirred for 16 h at room temperature. The reaction mixture was concentrated under reduced pressure, and the resulting crude product was purified by column chromatography (1:20 ethyl acetate/hexanes) to afford a colorless oil (1.5 g, 64%); $^1$H NMR (300 MHz, CDCl$_3$) δ 0.33 (s, 6 H), 1.79 (d, J=8.0 Hz, 2 H), 3.93 (s, 1 H), 4.87 (s, 1 H), 4.90 (d, J=5.0 Hz, 1 H), 5.77 (m, 1 H), 7.61 (d, J=8.0 Hz, 2 H), 8.03 (d, J=8.0 Hz, 2 H); $^{13}$C NMR (75 MHz, CDCl$_3$) −3.4, 23.6 52.3, 114.1, 128.7, 130.7, 133.9, 134.3, 145.2, 167.4. HRMS (EI) calcd for C$_{13}$H$_{18}$O$_2$Si 234.1076, found 234.1077.

Preparation of Resin (1 Scheme 21).

To a solution 4-allyldimethylsilylphenethyl alcohol (1 Scheme 8, 1.1 g, 5.0 mmol) in dry THF (20 mL) under a N$_2$ atmosphere was added 9-BBN (10 mL, 0.5 M solution in THF, 5.0 mmol) dropwise at 0° C. The mixture was gradually warmed to room temperature and stirred for 5 h. Pd(PPh$_3$)$_4$ (70 mg), 4-bromopolystyrene (2.5 g, 1.94 mmol/g), 2 N aqueous Na$_2$CO$_3$ (5 mL, 10 mmol), DMF (10 mL), were added. The reaction flask and reflux condenser were wrapped with aluminum foil, and the mixture was refluxed for 24 h. Pd(PPh$_3$)$_4$ (70 mg) was added to the reaction mixture which was refluxed again for 24 h. The resin was filtered and washed with THF (once), 1:1 THF/water (twice), water (twice), methanol (twice), CH$_2$Cl$_2$ (twice) and dried under reduced pressure.

Preparation of the Polymer Bound 4-Allyldimethylsilylphenethyl Bromide (2 Scheme 21).

To the above described resin (1 Scheme 21, 2 g) swelled in CH$_2$Cl$_2$ (120 mL) at 0° C. was added PPh$_3$ (1.3 g, 5 mmol) and CBr$_4$ (1.7 g, 5 mmol), and the reaction mixture was stirred for 2 days. The resin was filtered and washed with CH$_2$Cl$_2$ (twice), methanol (twice), 1:1 methanol/water (twice), methanol (twice), CH$_2$Cl$_2$ (twice), then dried under reduced pressure.

Preparation N-4-bromophenethyl-N-propyl Amine (4 Scheme 21).

To the aliquot of resin (200 mg) swelled in DMF (7 mL) was added propylamine (150 μL). The reaction mixture was agitated for 16 h at room temperature, then washed with DMF (twice), water (twice), methanol (twice), CH$_2$Cl$_2$ (twice). To the resin swelled in CH$_2$Cl$_2$ (7 μL) was added Br$_2$ (100 μL), and the mixture was stirred for 10 min at room temperature. Filtration of the cleavage solution from the resin followed by evaporation yielded the title compound.

Hydroboration and Suzuki Coupling of 4-Allyldimethylsilylphenethylalcohol (1 Scheme 8) to the Bromopolystyrene Resin.

To a solution of 4-allyldimethylsilylphenethyl alcohol (440 mg, 2 mmol) in dry THF (4 mL) under a N$_2$ atmosphere was added 9-BBN (4 mL, 0.5 M solution in THF, 2 mmol) dropwise at 0° C. The mixture was gradually warmed to room temperature and stirred for 4 h. THF was evaporated under reduced pressure and the reaction intermediate was dissolved in toluene (8 mL). After adding ground K$_3$PO$_4$ (424 mg, 4 mmol), resin prepared above (1.1 g), Pd(PPh$_3$)$_4$ (70 mg), the reaction mixture was degassed by bubbling with N$_2$ and sealed. The reaction flask was wrapped with aluminum foil and heated at 80° C. for 24 h. The resin was filtered and washed with MeOH (once), 1:1 MeOH/water (twice), water (twice), methanol (twice), CH$_2$Cl$_2$ (twice), then dried under reduced pressure. An aliquot of resin (100 mg) was treated with a solution of Br$_2$ (50 μL) in CH$_2$Cl$_2$ (8 mL) for 20 min. The cleavage solution was filtered and the resin was rinsed with CH$_2$Cl$_2$ (3 mL). Concentration of the combined filtrates gave 2-bromophenethyl alcohol (4 mg, loading level was determined to be 0.20 mequiv/g); $^1$H NMR (500 MHz, CDCl$_3$) δ 2.11 (bs, OH, 1 H), 2.86(t, J=6.5 Hz, 2 H), 3.88 (t, J=6.5 Hz, 2 H), 7.14 (d, J=8.0 Hz, 2 H), 7.46 (d, J=8.0 Hz, 2 H); $^{13}$C NMR (125 MHz,CDCl$_3$) 38.7, 63.7, 129.9, 13.1.0, 131.9, 132.3.

Preparation of (1 Scheme 22).

Synthesized from alcohol (1 Scheme 8) according to the procedure described for 1 Scheme 6 and purified by column chromatography (1:8 ethyl acetate/hexanes) to afford a colorless oil (93%); $^1$H NMR (300 MHz, CDCl$_3$) δ 0.29 (s, 6 H), 1.40 (t, J=7.2 Hz, 3 H), 1.43 (t, J=7.2 Hz, 3 H), 1.77 (d, J=8.1 Hz, 2 H), 2.90 (t, J=7.5 Hz, 2 H), 3.92 (t, 7.5 Hz, 2 H), 4.39 (q, J=7.2 Hz, 2 H), 4.86 (s, 1 H), 4.91 (d, J=9.3 Hz, 1 H), 5.78 (m, 1 H), 7.25 (d, J=7.5 Hz, 2 H), 7.49 (d, J=7.5 Hz, 2 H); $^{13}$C NMR (75 MHz, CDCl$_3$) −3.2, 14.1, 23.9, 27.9, 34.5, 44.8, 62.3, 85.2, 113.7, 128.8, 134.2, 134.8, 136.9, 139.3, 151.7, 162.1, 163.5; HRMS (EI) calcd for C$_{22}$H$_{33}$NO$_5$Si 419.2128, found 419.2142.

Preparation of N-Boc-4-allyldimethylsilylphenethylamine (2 Scheme 22).

Synthesized from 1 Scheme 22 according to the procedure described for 2 Scheme 6 and purified by column chromatography (1:8 ethyl acetate/hexanes) to afford a colorless oil (90%); $^1$H NMR (300 MHz, CDCl$_3$) δ 0.32 (s, 6 H), 1.48 (s, 9 H), 1.79 (d, J=7.5 Hz, 2 H), 2.83 (app t, J=6.9 Hz, 2 H), 3.42 (m, 2 H), 4.74 (bs, NH, 1 H), 4.88 (s, 1 H), 4.92 (d, J=7.8 Hz, 1 H), 5.81 (m, 1 H), 7.24 (d, J=7.8 Hz, 1 H), 7.50 (d, J=7.8 Hz, 2 H); $^{13}$C NMR (75 MHz, CDCl$_3$) −3.1, 24.0, 28.7, 36.5, 42.0, 79.4, 113.7, 128.6, 134.2, 134.9, 136.6, 140.2, 156.2; HRMS (EI) calcd for C$_{18}$H$_{29}$NO$_2$Si 319.1967, found 319.1984.

Preparation of 2-[3-(4-Allyldimethylsilylphenyl)propoxy] tetrahydro-2H-pyran (3 Scheme 22).

To a solution of 1-allyldimethylsilyl-4-bromobenzene (1 Scheme 1, 1.3 g, 5 mmol) in dry THF (10 mL) at −78° C. was added t-butyllithium (3.0 mL, 1.7 M solution in pentane, 5.1 mmol) over a period of 5 min. After 30 min stirring at −78° C., 2-(3-bromopropoxy)tetrahydro-2H-pyran (850 μL, 5 mmol) was added dropwise. The reaction mixture was warmed to room temperature and stirred further for 16 h. Concentrated NH$_4$Cl (1 mL) was added to the solution, and the reaction mixture was concentrated under reduced pressure. The residue was extracted with ethyl acetate (10 mL) and brine (5 mL), and the organic layer was dried (Na$_2$SO$_4$), concentrated. The crude product was purified by column chromatography (1:20 ethyl acetate/hexanes) to afford a colorless oil (621 mg, 39%). $^1$H NMR (300 MHz, CDCl$_3$) δ 0.33 (s, 6 H), 1.52–1.94 (8H), 1.99 (m, 2 H), 2.77 (m, 2 H), 3.40–3.57 (m, 2 H), 3.78–3.96 (m, 2 H), 4.64 (m, 1 H), 4.88 (s, 1 H), 4.93 (d, J=8.7 Hz, 1 H), 5.82 (m, 1 H), 7.26 (d, J=7.8 Hz, 2 H), 7.49 (d, J=7.8 Hz, 2 H), $^{13}$C NMR (75 MHz, CDCl$_3$) −3.1, 19.9, 24.1, 25.8, 31.1, 31.5, 32.8, 62.6, 67.1, 99.1, 113.6, 128.3, 134.0, 135.0, 135.7, 143.2; HRMS (EI) calcd for C$_{19}$H$_{30}$O$_2$Si 318.2015, found 318.2009.

Preparation of 3-(4-Allyldimethylsilylphenyl)-1-propanol (4 Scheme 22).

2-[3-(4-allyldimethylsilylphenyl)propoxy]tetrahydro-2H-pyran (3 Scheme 22, 600 mg, 1.9 mmol) was treated with catalytic amount of p-TsOH (20 mg) in methanol (10 mL). After being stirred for 16 h at room temperature, the reaction mixture was concentrated under reduced pressure and purified by column chromatography (1:5 ethyl acetate/hexanes) to afford a colorless oil (342 mg, 77%); $^1$H NMR (300 MHz, CDCl$_3$) δ 0.31 (s, 6 H), 1.79 (d, J=8.1 Hz, 2 H), 1.93 (m, 2 H), 2.74 (t, J=8.4 Hz, 2 H), 3.71 (d, J=6.6 Hz, 2 H), 4.87 (s, 1 H), 4.92 (m, 1 H), 5.81 (m, 1 H), 7.24 (d, J=7.8 2 H), 7.50 (d, J=7.8 Hz, 2 H); $^{13}$C NMR (75 MHz, CDCl$_3$) −3.1, 24.1, 32.4, 34.4, 62.4, 113.6, 128.2, 133.9, 135.0, 135.9, 143.1; HRMS (EI) calcd for C$_{14}$H$_{22}$OSi 234.1439, found 234.1440.

Preparation of Resin (1 Scheme 23).

To a solution (4S)-3-[2-(4-allyldimethylsilylphenyl)-1-oxoethyl]-4-benzyl-2-oxazolidinone (3 Scheme 8, 393 mg, 1.0 mmol) in dry THF (4 mL) under a N$_2$ atmosphere was added 9-BBN (2.0 mL, 0.5 M solution in THF, 1.0 mmol) dropwise at 0° C. The mixture was gradually warmed to room temperature and stirred for 5 h. Pd(PPh$_3$)$_4$ (35 mg), 4-bromopolystyrene (750 mg, 1.94 mmol/g), 2 N aqueous Na$_2$CO$_3$ (1.0 mL, 2.0 mmol), DMF (5 mL), were added. The reaction flask and reflux condenser were wrapped with aluminum foil, and the mixture was heated to 65° C. for 24 h. Pd(PPh$_3$)$_4$ (70 mg) was added to the reaction mixture which was heated to 65° C. for 24 h. The resin was filtered and washed with THF (once), 1:1 THF/water (twice), water (twice), methanol (twice), CH$_2$Cl$_2$ (twice). To the aliquot of resin (100 mg) swelled in CH$_2$Cl$_2$ (7 mL) was added Br$_2$ (50 μL), and the mixture was stirred for 10 min at room temperature. Filtration of the cleavage solution from the resin followed by evaporation yielded bromo analog (2 Scheme 23) as a white powder; $^1$H NMR (300 MHz, CDCl$_3$) δ 2.76 (dd, J=13.20 Hz, 1 H), 3.25 (dd, J=13.20, 3.30 Hz, 1 H), 4.15–4.33 (4 H), 4.68 (m, 1 H), 7.11–7.15 (2 H), 7.21 (d, J=8.40 Hz, 2 H), 7.25–7.33 (3 H), 7.48 (d, J=8.40 Hz, 2 H).

Preparation of 1-Allyldimethylsilyl-4-iodobenzene (1 Scheme 24).

To a solution 1,4-diiodobenzene (16.5 g, 50 mmol) in dried THF (250 mL) at −78° C. was added n-butyllithium (22 mL, 2.5 M solution in hexanes, 55 mmol) over a period of 30 min. After being stirred for 10 min at −78° C., allylchlorodimethylsilane (6.7 g, 50 mmol) in was added dropwise over a period of 20 min, and the reaction mixture was warmed to room temperature. After stirring for 1 h at room temperature the reaction mixture was concentrated, and the residue was extracted with ether and brine. The organic layer was dried (Na$_2$SO$_4$) and distilled (Kugelrohr) under reduced pressure to provide a liquid (11.5 g, 76%); $^1$H NMR (300 MHz, CDCl$_3$) δ 0.32 (s, 6 H), 1.78 (d, J=7.5 Hz, 2 H), 4.89 (s, 1 H), 4.92 (d, J=4.0 Hz, 1 H), 5.78 (m, 1 H), 7.27 (d, J=7.5 Hz, 2 H), 7.74 (d, J=7.5 Hz, 2 H); $^{13}$C NMR (75 MHz, CDCl$_3$) −3.5, 23.8, 114.1, 134.4, 135.6, 137.1, 138.3, 139.6; HRMS calcd for C$_{11}$H$_{15}$ISi 301.9987, found 301.9990.

Preparation of Ethyl 3-(4-Allyldimethylsilylphenyl) propanoate (2 Scheme 24).

To a solution of 5 mol % Pd(Ph$_3$)$_4$ (288 mg, 0.25 mmol) and 1-allyldimethylsilyl-4-iodobenzene (1 Scheme 24, 1.5 g, 5 mmol) in dry THF (10 mL) was added 3-ethoxy-3-oxopropylzinc bromide (0.5 M solution in THF, 10 mL, 5 mmol). After degassing by bubbling with N$_2$, the reaction mixture was sealed and stirred for 16 h at 60° C. The mixture was treated with saturated NH$_4$Cl (10 mL) and extracted. The organic layer was dried over Na$_2$SO$_4$ and concentrated. The resulting crude product was purified by column chromatography (1:30 ethyl acetate/hexanes) to afford a colorless oil (1.1 g, 80%); $^1$H NMR (300 MHz, CDCl$_3$) δ 0.34 (s, 6 H), 1.29 (d, J=7.2 Hz, 3 H), 1.81 (d, J=7.8 Hz, 2 H), 2.68 (t, J=7.7 Hz, 2 H), 3.02 (t, J=7.7 Hz, 2 H), 4.18 (q, J=7.2 Hz, 2 H), 4.90 (s, 1 H), 4.94 (d, J=7.8 Hz, 1 H), 5.82 (m, 1 H), 7.27 (d, J=7.8 Hz, 2 H), 7.51 (d, J=7.8 Hz, 2 H); $^{13}$C NMR (75 MHz, CDCl$_3$) −3.1. 14.5 24.0, 31.2, 36.0, 60.6, 113.7, 128.1, 134.1, 134.9, 136.4, 141.7, 173.0; HRMS (EI) calcd for C$_{16}$H$_{24}$O$_2$Si 276.1545, found 276.1548.

Preparation of Ethyl 4-(4-Allyldimethylsilylphenyl) benzoate (3 Scheme 24).

To a solution of 5 mol % Pd(Ph$_3$)$_4$ (288 mg, 0.25 mmol) and 1-allyldimethylsilyl-4-iodobenzene (1 Scheme 24, 1.5 g, 5 mmol) in dry THF (10 mL) was added (4-carbethoxyphenyl)zinc iodide (0.5 M solution in THF, 10 mL, 5 mmol). After degassing by bubbling with N$_2$, the reaction mixture was sealed and stirred for 16 h at 60° C. The mixture was treated with saturated NH$_4$Cl (10 mL) and extracted. The organic layer was dried over Na$_2$SO$_4$ and concentrated. The resulting crude product was purified by column chromatography (1:30 ethyl acetate/hexanes) to afford a colorless oil (12 g, 72%); $^1$H NMR (300 NMz, CDCl$_3$) δ 0.39 (s,6H), 1.46 (t, J=7.5 Hz, 3 H), 1.85 (d, J 8.0 Hz, 2 H), 4.45 (d, J=7.5 Hz, 2 H), 4.94 (s, 1 H), 4.97 (m, 1 H), 5.84 (m, 1 H), 7.65(4 H), 7.70 (d, J=8.0 Hz, 2 H), 8.18 (d, J=8.18 (d, J=8.0 Hz, 2 H); HRMS (EI) calcd for C$_{20}$H$_{24}$O$_2$Si 324.1545, found 324.1545.

Preparation of 1-Allyldimethylsilyl-4-bromo-naphthalene (1 Scheme 26).

To a solution 1,4-dibromonaphthalene (28.6 g, 0.1 mol) in dry THF (800 mL) at −78° C. was added t-butyllithium (59.0 mL, 1.7 M solution in pentane, 0.1 mol) over a period of 20 min. After 30 min stirring at −78° C., allylchlorodimethylsilane (13.5 g, 0.1 mol) in THF (25 mL) was added dropwise over a period of 30 min. The reaction mixture was stirred further for 1 h and warmed to room temperature. Concentrated NH$_4$Cl (5 mL) was added to the solution, and the reaction mixture was concentrated. The resulting yellow oil was concentrated, extracted with ethyl acetate/water, and the organic layer was dried, concentrated. The crude product was Kugelrohr distilled to give a colorless oil (25.6 g, 84%); $^1$H NMR (300 MHz, CDCl$_3$) δ 0.57 (s, 6 H), 2.07 (d, J=8.10 Hz, 2 H), 4.94–5.04 (2 H), 5.87 (ddt, J=16.80, 10.20, 8.10 Hz, 1 H), 7.56 (d, J=7.20 Hz, 1 H), 7.61–7.70 (2 H), 7.83 (d, J=7.20 Hz, 1 H), 8.19 (m, 1 H), 8.43 (m, 1 H); $^{13}$C NMR (75 MHz, CDCl$_3$) –1.5 (2 C), 24.5, 114.3, 126.0, 126.9, 127.1, 128.6, 128.8, 129.7, 132.2, 134.2, 134.7.

Preparation of 1-Allyldimethylsilyl-4-naphthalenemethanol (2 Scheme 26).

To a vigorously stirred suspension of activated magnesium turning (480 mg, 20 mmol) in dry THF (70 mL) were added a piece of 12 and ethyl iodide (50 μL). The reaction mixture was heated to reflux until the red color disappeared. Heating (65° C.) of the suspension was continued while a solution of 1-allyldimethylsilyl-4-bromo-naphthalene (1 Scheme 26, 3.0 g, 10 mmol) in THF (20 mL) was added over a period of 15 min. Upon completion of the addition, the gray solution was heated further for 10 min and transferred to a separate flask containing. paraformaldehyde (700 mg) in THF (20 mL) via cannula. After stirring the reaction mixture at 50° C. for 30 min, concentrated NH$_4$Cl (10 mL) was added to the solution, and the reaction mixture was concentrated. The residue was extracted with ethyl acetate (70 mL) and brine (30 mL), and the organic layer was dried (Na$_2$SO$_4$), concentrated. The crude product was purified by column chromatography (1:5 ethyl acetate/hexanes) to afford a colorless oil (1.8 g, 75%); $^1$H NMR (300 MHz, CDCl$_3$) δ 0.58 (s, 6 H), 2.08 (d, J=7.50 Hz, 2 H), 3.21 (s, OH, 1 H), 4.93–5.03 (2 H), 5.04 (s, 2 H), 5.89 (m, 1 H), 7.47 (d, J=7.20 Hz, 2 H), 7.53–7.64 (2 H), 7.69 (d, J=6.90 Hz, 1 H), 8.11 (d, J=8.80 Hz, 1 H), 8.23 (d, J=8.80 Hz, 1 H), $^{13}$C NMR (75 MHz, CDCl$_3$) –1.50 (2 C), 24.6, 63.5, 114.1, 124.5, 124.8, 125.9, 126.8, 129.1, 131.4, 133.7, 135.0, 137.3, 137.5, 138.3.

Preparation of 1-Allyldimethylsilyl-4-naphthaldehyde (5 Scheme 6).

To a solution 1-allyldimethylsilyl-4-bromo-naphthalene (1 Scheme 26, 3.0 g, 10 mmol) in dry THF (150 mL) at –78° C. was added t-butyllithium (6.0 mL, 1.7 M solution in pentane, 10.2 mmol) over a period of 10 min. After 30 min stirring at –78° C., anhydrous DMF (1.5 mL, 20 mmol) was added dropwise. The reaction mixture was stirred further for 1 h and warmed to room temperature. Concentrated NH$_4$Cl (5 mL) was added to the solution, and the reaction mixture was concentrated. The residue was extracted with ethyl acetate (50 mL) and brine (10 mL), and the organic layer was dried (Na$_2$SO$_4$), concentrated. The crude product was purified by column chromatography (1:20 ethyl acetate/ hexanes) to afford a colorless oil (2.1 g, 88%); $^1$H NMR (300 MHz, CDCl$_3$) δ 0.53 (s, 6 H), 2.03 (d, J=7.80 Hz, 2 H), 4.88–4.97 (2 H), 5.79 (m, 1 H), 7.60–7.70 (2 H), 7.84 (d, J=7.50 Hz, 1 H), 7.89 (d, J=6.90 Hz, 1 H), 8.20 (d, J=8.10 Hz, 1 H), 9.35 (d, J=8.10 Hz, 1 H), 10.39 (s, 1 H); $^{13}$C NMR (75 MHz, CDCl$_3$) –1.7 (2C), 24.2, 114.5, 126.1, 126.9, 128.6, 128.7, 132.9, 134.3, 135.4, 137.6, 146.8, 194.1.

Preparation of Resin (3 Scheme 26).

To a solution 1-allyldimethylsilyl-4-naphthalenemethanol (2 Scheme 26, 750 mg, 3.1 mmol) in dry THF (20 mL) under a N$_2$ atmosphere was added 9-BBN (6.2 mL, 0.5 M solution in THF, 3.1 mmol) dropwise at 0° C. The mixture was gradually warmed to room temperature and stirred for 5 h. Pd(PPh$_3$)$_4$ (60 mg), 4-bromopolystyrene (1.5 g, 1.94 mmol/ g), 2 N aqueous Na$_2$CO$_3$ (3.1 mL, 6.2 mmol), DMF (10 mL), were added. The reaction flask and reflux condenser were wrapped with aluminum foil, and the mixture was heated to 65° C. for 24 h. Pd(PPh$_3$)$_4$ (60 mg) was added to the reaction mixture which was heated to 65° C. for 24 h. The resin was filtered and washed with THF (once), 1:1 THF/water (twice), water (twice), methanol (twice), CH$_2$Cl$_2$ (twice). The resin was used directly for the next reaction.

Preparation of Resin (4 Scheme 26).

To the dried resin (3 Scheme 26, 100 mg) swelled in dry THF (8 mL) was added PPh$_3$ (52 mg, 0.2 mmol) and CBr$_4$ (66 mg, 0.2 mmol), and the reaction mixture was agitated for 1 h at room temperature. The resin was filtered and washed with CH$_2$Cl$_2$ (twice), methanol (twice), CH$_2$Cl$_2$ (twice), then dried under reduced pressure. The resin was treated with a solution of CH$_2$Cl$_2$ (7 mL) and Br$_2$ (150 μL) for 10 min. The cleavage solution was removed, and the resin was rinsed with CH$_2$Cl$_2$ (3 mL). Concentration of the combined filtrates gave the known 4-bromonaphathalene-1-methylbromide (12 mg, 0.40 mequiv/g); $^1$H NMR (300 MHz, CDCl$_3$) δ 4.92 (s, 2 H), 7.39 (d, J=7.60 Hz, 1 H), 7.60–7.70 (2 H), 7.72 (d, J=7.80 Hz, 1 H), 8.14 (m, 1 H), 8.32 (m, 1 H).

Preparation of Ethyl 2-[[(4-Methylphenyl)sulfonyl](4-bromo-1-naphthyl)methylamino] Acetate (5 Scheme 26).

To the above described resin (3 Scheme 26, dried, 100 mg) swelled in dry THF (8 mL) was added PPh$_3$ (52 mg, 0.2 mmol) and CBr$_4$ (66 mg, 0.2 mmol), and the reaction mixture was agitated for 1 h at room temperature. The resin was filtered and washed with CH$_2$Cl$_2$ (twice), methanol (twice), CH$_2$Cl$_2$ (twice), then dried under reduced pressure. To the resin swelled: in DMF (7 mL) were added glycine ethyl ester hydrochloride(10 equiv) and DIPEA (10 equiv). The reaction mixture was agitated for 16 h at room temperature, then washed with DMF (twice), water (twice), methanol (twice), CH$_2$Cl$_2$ (twice). To the resin was swelled in CH$_2$Cl$_2$ (7 mL) were added p-toluenesulfonyl chloride (10 equiv), TEA (10 equiv) DMAP (30 mg). After agitation for 20 h at room temperature the resin was washed with CH$_2$Cl$_2$ (twice), methanol (twice), CH$_2$Cl$_2$ (twice). To the resin swelled in CH$_2$Cl$_2$ (7 mL) was added Br$_2$ (100 μL), and the mixture was stirred for 10 min at room temperature. Filtration of the cleavage solution from the resin followed by evaporation yielded the compound (5 Scheme 26, 14 mg, 76%); $^1$H NMR (300 MHz, CDCl$_3$) δ 1.04 (t, J=7.20 Hz, 3 H), 2.46 (s, 3 H), 3.79 (s, 2 H), 3.88 (q, J=7.20 Hz, 2 H), 4.94 (s, 2 H), 7.15 (d, J=7.50 Hz, 2 H), 7.30–7.70 (3 H), 7.56–7.82 (4 H), 8.22–8.35 (2 H).

Preparation of 2-Bromo-5-pyridinecarboxaldehyde (1 Scheme 27).

To a suspension of 2,5-dibromopyridine (18.6 g, 78.5 mmol) in dry diethyl ether (400 mL) at –78° C. was added n-butyllithium (2.5 M in hexanes, 31.4 mL, 78.5 mmol) over a period of 20 min. After stirring 30 min at this temperature, anhydrous DMF (9.1 mL, 118 mmol) was added over a period of 5 min, and the reaction mixture was stirred for 30 min then warmed to room temperature. Saturated NH$_4$Cl (10 mL) was added to the reaction mixture. The layers were separated, and the organic layer was dried (Na$_2$SO$_4$), concentrated. The crude product was purified by column chromatography (1:5 ethyl acetate/hexanes) to afford a brown solid (12.5 g, 86%); $^1$H NMR (300 MHz, CDCl$_3$) δ 7.61 (dd, J=8.10, 0.60 Hz, 1 H), 7.95 (dd, J=8.10, 2.10 Hz, 1 H), 8.74 (dd, J=2.10, 0.60 Hz, 1 H), 10.02 (s, 1 H); $^{13}$C NMR (75 MHz, CDCl$_3$) 129.2, 130.8, 137.7, 148.4, 152.6, 189.7.

Preparation of 2-(2-Bromo-5-pyridyl)-1,3-dioxolane (2 Scheme 27).

A mixture of 2-bromo-5-pyridinecarboxaldehyde (2 Scheme 27, 12.0 g, 64.5 mmol) and ethylene glycol (5.4 mL, 96.8 mmol) and p-toluenesulfonic acid (100 mg) in benzene (150 mL) was refluxed in a Dean Stark apparatus for 16 h. The reaction mixture was cooled to room temperature, and the solution was extracted with cold water/ethyl acetate. The organic layer was dried ($Na_2SO_4$) and concentrated. The crude product was purified by column chromatography (1:4 ethyl acetate/hexanes) to afford a orange colored oil (10.5 g, 70%); $^1$H NMR (300 MHz, $CDCl_3$) δ 3.82–3.96 (4 H), 5.64 (s, 1 H), 7.34 (d, J=8.10 Hz, 1 H), 7.49 (dd, J=8.10 Hz, 1 H), 8.29 (d, J=2.10 Hz, 1 H); $^{13}$C NMR (75 MHz, $CDCl_3$) 65.5 (2C), 101.2, 128.0, 133.4, 137.0, 142.8, 148.8. HRMS (EI) calcd for $C_8H_8BrNO_2$ 228.9738, found 230.9718.

Preparation of 2-(5-Allyldimethylsilyl-2-pyridyl)-1,3-dioxolane (3 Scheme 27)

To a solution of 2-(2-bromo-5-pyridyl)-1,3-dioxolane (2 Scheme 27, 10.2 g, 44.3 mmol) in dried THF (400 mL) at −78° C. was added n-butyllithium (18.0 mL, 2.5 M solution in hexanes, 45 mmol) over a period of 20 min. After stirring 30 min at this temperature, allylchlorodimethylsilane (6.1 g, 45 mmol) in THF (15 mL) was added dropwise over a period of 20 min. The reaction mixture was stirred for 1 h at −78° C. and warmed to room temperature. THF was removed under reduced pressure, and the residue was extracted with $H_2O$/ethyl acetate. The organic layer was washed with brine, dried ($Na_2SO_4$), and concentrated to give a orange colored oil which was purified by column chromatography (1:4 ethyl acetate/hexanes) to afford an oil (6.1 g, 55%); $^1$H NMR (300 MHz, $CDCl_3$) δ 0.32 (s, 6 H), 1.83 (dt, J=8.10, 1.05 Hz, 2 H), 4.00–4.14 (4 H), 4.70–4.89 (2 H), 5.72 (ddt, J=17.10, 10.50, 7.80 Hz, 1 H) 5.83 (s, 1 H), 7.51 (dd, J=7.80, 0.60 Hz, 1 H), 7.69 (dd, J=7.80, 2.40 Hz, 1 H), 8.86 (m, 1 H); $^{13}$C NMR (75 MHz, $CDCl_3$) 3.9 (2C), 22.8, 65.6 (2C), 102.4, 113.8, 129.0, 132.1, 134.5, 148.8.

Preparation of 2-Bromo-5-hydroxymethylpyridine (4 Scheme 27).

To a solution of 2-bromo-5-pyridinecarboxaldehyde (1 Scheme 27, 9.3 g, 50 mmol) in EtOH (300 mL) was added sodium borohydride (3.7 g, 100 mmol) portion-wise for 10 min at room temperature. After further stirring for 30 min, excess sodium borohydride was quenched by slow addition of acetone (10 mL) to the reaction mixture. The solvent was evaporated and the residue was extracted with ethyl acetate/brine. The organic layer was dried ($Na_2SO_4$) and concentrated to afford a colorless oil (8.5 g, 90%); $^1$H NMR (300 MHz, $CDCl_3$) δ 4.58 (bs, OH, 1 H), 4.62 (s, 2 H), 7.40 (d, J=8.40, 1 H), 7.54 (dd, J=7.2, 1.2 Hz, 1 H), 8.20 (s, 1 H); $^{13}$C NMR (75 MHz, $CDCl_3$) 61.5, 128.3, 136.6, 138.0, 140.6, 148.6. HRMS (EI) calcd for $C_6H_6BrNO$ 186.9632 and 188.9613, found 186.9629 and 188.9663.

Preparation of 2-[(2-Bromopyridin-5-yl)methoxy]tetrahydro-2H-pyran (5 Scheme 27).

To a solution of 2-bromo-5-hydroxymethylpyridine (4 Scheme 27, 7.3 g, 38.8 mmol) and 3,4-dihydro-2H-pyran (3.6 g, 42.7 mmol) in dichloromethane (150 mL) was added p-TsOH (200 mg) and the mixture was stirred for 5 h at room temperature. The reaction mixture was concentrated and purified by column chromatography (1:5 ethyl acetate/hexanes) to give the desired compound as a liquid (10 g, 95%); $^1$H NMR (300 MHz, $CDCl_3$) δ 1.42–1.81 (6 H), 3.48 (m, 1 H), 3.80 (m, 1 H), 4.43 (m, 1 H), 4.62–4.73 (2 H), 7.42 (m, 1 H), 7.53 (m, 1 H), 8.30 (m, 1 H); $^{13}$C NMR (75 MHz, $CDCl_3$) 19.5, 25.5, 30.6, 62.5, 65.8, 98.3, 128.0, 133.5, 138.4, 141.3, 149.7. HRMS (EI) calcd for $C_{11}H_{14}BrNO_2$ 271.0208 and 273.0187, found 271.0207 and 273.0171.

Preparation of 2-[(2-Allyldimethylsilylpyridin-5-yl)methoxy]tetrahydro-2H-pyran (6 Scheme 27).

To a solution of 2-[(2-bromopyridin-5-yl)methoxy]tetrahydro-2H-pyran. (5 Scheme 27, 5.1 g, 18.7 mmol) in dry THF (200 mL) at −78° C. was added n-butyllithium (7.5 mL, 2.5 M solution in hexanes, 18.7 mmol). After being stirred for 10 min −78° C., allylchlorodimethylsilane (2.5 g, 18.7 mmol) was added dropwise over a period of 20 min. The reaction mixture was stirred further for 1 h and warmed to room temperature. Concentrated $NH_4Cl$ (5 mL) was added to the solution, and the reaction mixture was concentrated. The resulting yellow oil was concentrated, extracted with ethyl acetate/water, and the organic layer was dried, concentrated, and purified by column chromatography (1:7 ethyl acetate/hexanes) to give the desired compound as a liquid (3 g, 55%) $^1$H NMR (300 MHz, $CDCl_3$) δ 0.31 (s, 6 H), 1.45–1.68(6 H), 1.82 (d, J=8.40 Hz, 2 H), 3.54 (m, 1 H), 3.87 (m, 1 H), 4.47 (d, J=12.30 Hz, 1 H), 4.70 (t, J=3.45 Hz, 1 H), 4.77 (d, J=12.30 Hz, 1 H), 4.80–4.87 (2 H), 7.75 (m, 1 H), 7.46 (d, J=7.50 Hz, 1 H), 7.58 (dd, J=7.50, 1.80 Hz, 1 H), 8.76 (1 H); $^{13}$C NMR (75 MHz, $CDCl_3$) −3.8 (2C), 19.4, 22.9, 25.8, 30.6, 62.3, 66.7, 98.1, 113.8, 129.1, 133.0, 133.6, 134.6, 149.9, 165.9. HRMS (EI) calcd for $C_{16}H_{25}NO_2Si$ 291.1654, found 291.1556.

Preparation of 5-Allyldimethylsilyl-2-bromopyridine (7 Scheme 27).

To a solution of 2,5-dibromopyridine (18.6 g, 78.5 mmol) in dry THF (700 mL) at −78° C. was added n-butyllithium (31.4 mL, 2.5 M solution in hexanes, 78.5 mmol). After being stirred for 1 h −78° C., allylchlorodimethylsilane (11 g, 78.5 mmol) was added dropwise over a period of 20 min. The reaction mixture was stirred further for 1 h and warmed to room temperature. Concentrated $NH_4Cl$ (5 mL) was added to the solution, and the reaction mixture was concentrated. The resulting yellow oil was concentrated, extracted with ethyl acetate/water, and the organic layer was dried, concentrated, and purified by column chromatography (1:5 ethyl acetate/hexanes) to give the desired compound as a liquid (12.7 g, 55%); $^1$H NMR (300 MHz, $CDCl_3$) δ 0.19 (s, 6 H), 1.63 (d, J=7.80 Hz, 2 H), 7.10 (dt, J=6.90, 0.90 Hz, 1 H), 4.75 (s, 1 H), 5.59 (ddt, J=16.50, 10.50, 8.10 Hz, 1 H), 7.32 (d, J=8.10 Hz, 1 H), 7.50 (m, 1 H), 8.28 (d, J=2.10 Hz, 1 H); $^{13}$C NMR (75 MHz, $CDCl_3$) −3.5 (2C), 23.2, 114.6, 127.8, 132.5, 133.4, 143.7, 143.8, 154.6. HRMS (EI) calcd for $C_{10}H_{14}BrNSi$ 255.0077 and 257.0058, found 255.0054 and 257.0028.

Preparation of 5-Allyldimethylsilyl-2-pyridinecarboxaldehyde (8 Scheme 27).

To a solution of 5-allyldimethylsilyl-2-bromopyridine (7 Scheme 27, 14.5 g, 56 mmol) in dry THF (400 mL) at −78° C. was added n-butyllithium (2.5 M in hexanes, 22.5 mL, 56 mmol) over a period of 20 min. After stirring 30 min at this temperature, anhydrous DMF (6.5 mL, 84 mmol) was added over a period of 5 min, and the reaction mixture was stirred for 30 min then warmed to room temperature. Saturated NCl (10 mL) was added to the reaction mixture. The layers were separated, and the organic layer was dried ($Na_2SO_4$), concentrated. The crude product was purified by column chromatography (1:7 ethyl acetate/hexanes) to afford an oil (4.2 g, 36%); $^1$H NMR (300 MHz, $CDCl_3$) δ 0.26 (s, 6 H), 1.71 (d, J=8.40 Hz, 2 H), 4.74 (m, 1 H), 4.79 (s, 1 H), 5.62 (m, 1 H), 7.80 (d, J=7.80 Hz, 1 H), 7.89 (m, 1 H), 8.75 (d, J=0.90 Hz, 1 h), 9.97 (s, 1 H); $^{13}$C NMR (75 MHz, $CDCl_3$) 3.65 (2C), 23.1, 114.7, 120.7, 133.3, 139.9, 142.7, 153.0, 154.5, 193.8. HRMS (EI) calcd for $C_{11}H_{15}NOSi$ 205.0923, found 205.0927.

Preparation of 5-Allyldimethylsilyl-2-hydroxymethylpyridine (9 Scheme 27).

To a solution of 5-allyldimethylsilyl-2-pyridinecarboxaldehyde (8 Scheme 27, 3.1 g, 15 mmol) in EtOH (80 mL) was added sodium borohydride (1.1 g, 30 mmol) portion-wise for 10 min at room temperature. After further stirring for 30 min, excess sodium borohydride was quenched by slow addition of acetone (5 mL) to the reaction mixture. The solvent was evaporated and the residue was extracted with ethyl acetate/brine. The organic layer was dried ($Na_2SO_4$) and concentrated to afford an oil (2.7 g, 87%); $^1$H NMR (300 MHz, $CDCl_3$) δ 0.27 (s, 6 H), 1.72 (dt, J=6.75, 1.05 Hz, 2 H), 4.74 (s, 2 H), 4.80 (dd, J=3.00, 1.20 Hz, 1 H), 4.48 (d, J=1.20 Hz, 1 H), 5.36 (bs, OH, 1 H), 5.69 (ddt, J=14.70, 9.30, 7.80 Hz, 1 H), 7.33 (d, J=7.80 Hz, 1 H), 7.76 (d, J=7.80 Hz, 1 H), 8.54 (s, 1 H), $^{13}$C NMR (75 MHz, $CDCl_3$) −3.4 (2C), 23.5, 64.6 114.3, 120.6, 131.9, 133.9, 142.6, 153.0, 160.8. HRMS (EI) calcd for $C_{11}H_{17}NOSi$ 207.1079, found 206.0999.

Preparation of 2-Allyldimethylsilylthiophene (1 Scheme 28).

To a solution of thiophene (8.4 g, 0.1 mol) in dried THF (300 mL) at −78° C. was added n-butyllithium (40 mL, 2.5 M solution in hexanes, 0.1 mol) over a period of 5 min. After 30 min of further stirring at −78° C., allylchlorodimethylsilane (13.5 g, 0.1 mol) was added dropwise over a period of 20 min, and the reaction mixture was warmed to room temperature. After 1 h of further stirring at room temperature, concentrated $NH_4Cl$ (3 mL) was added, and the reaction mixture was concentrated. Kugelrohr distillation of the crude oil under reduced pressure afforded a colorless oil (16.7 g, 92%); $^1$H NMR (300 MHz, $CDCl_3$) δ 0.39 (s, 6 H), 1.84 (dd, J=8.10, 1.20 Hz, 2 H), 4.92 (s, 1 H), 4.97 (m, 1 H), 5.85 (m, 1 H), 7.24 (m, 1 H), 7.33 (dd, J=3.30, 1.50 Hz, 1 H), 7.65 (dd, J=5.70, 1.20 Hz, 1 H); $^{13}$C NMR (75M Hz, $CDCl_3$) −2.0 (2C), 24.8, 114.2, 128.4, 131.0, 134.4, 134.8, 138.3; HRMS (EI) calcd for $C_9H_{15}SSi$ 182.0585, found 182.0583.

Preparation of 2-Allyldimethylsilylthiophene-5-carboxaldehyde (1 Scheme 6).

To a solution of 2-allyldimethylsilylthiophene (1 Scheme 28, 10.6 g, 58.5 mmol) in dry THF (300 mL) at −78° C. was added n-butyllithium (23.4 mL, 2.5 M solution in hexanes, 58.5 mmol) over a period of 10 min. After 30 min stirring at −78° C., anhydrous DMF (6.8 mL, 87.8 mmol) was added dropwise. The reaction mixture was stirred further for 1 h and warmed to room temperature. Concentrated $NH_4Cl$ (4 mL) was added to the solution, and the reaction mixture was concentrated. The residue was extracted with ethyl acetate (150 mL) and brine (20 mL), and the organic layer was dried ($Na_2SO_4$) and concentrated to afford a colorless oil (12.1 g, 98%); $^1$H NMR (300 M $CDCl_3$) δ 0.32 (s, 6 H), 1.76 (dd, J=8.10, 1.20 Hz, 2 H), 4.85 (m, 1 H), 4.89 (s, 1 H), 5.72 (m, 1 H), 7.30 (d, J=3.60 1 H), 7.77 (dd, J=3.60, 1.50 Hz, 1 H), 9.90 (s, 1 H); $^{13}$C NMR (75 MHz, $CDCl_3$) −2.4 (2C), 24.0, 114.9, 133.3, 135.4, 137,0, 148.7, 150.7, 182.7; HRMS (EI) calcd for $C_{10}H_{14}OSSi$ 210.0533, found 210.0531.

Preparation of 2-Allyldimethylsilyl-5-thienylmethanol (2 Scheme 28).

To a solution of 2-allyldimethylsilylthiophene-5-carboxaldehyde (1 Scheme 6, 8.6 g, 40.8 mmol) in EtOH (150 mL) was added sodium borohydride (3.0 g, 82 mmol) portion-wise for 10 min at room temperature. After further stirring for 30 min, excess sodium borohydride was quenched by slow addition of acetone (5 mL) to the reaction mixture. The solvent was evaporated and the residue was extracted with ethyl acetate/brine. The organic layer was dried ($Na_2SO_4$) and concentrated to afford a colorless oil (7.5 g, 87%); $^1$H NMR (300 MHz, $CDCl_3$) δ 0.36 (s, 6 H), 1.81 (d, J=8.10, 2 H), 2.85 (bs, OH, 1 H), 4.81 (s, 2 H), 4.91 (s, 1 H), 4.96 (m, 1 H), 5.84 (ddt, J=16.50, 10.50, 8.10 Hz, 1 H), 7.08 (d, J=3.30 Hz, 1 H), 7.17 (d, J=3.30 Hz, 1 H); $^{13}$C NMR (75 MHz, $CDCl_3$) −2.1 (2C), 24.6, 59.9, 114.2, 127.0, 134.3, 134.8, 138.8, 149.9; HRMS (EI) calcd for $C_{10}H_{16}OSSi$ 212.0692, found 212.0690.

Preparation of 2-Bromo-5-chloromethylthiophene (5 Scheme 28).

To a solution of 2-allyldimethylsilyl-5-thienylmethanol (2 Scheme 28, 850 mg, 4 mmol) in dry THE (8 mL) under a $N_2$ atmosphere was added 9-BBN (8 mL, 0.5 M solution in THF, 2 mmol) under a $N_2$ atmosphere. After stirring for 5 h at room temperature, $Pd(PPh_3)_4$ (140 mg), 4-bromopolystyrene (2.0 g, 1.94 mmol/g), 2 N aqueous $Na_2CO_3$ (4 mL, 8 mmol), and DMF (20 mL) were added. The reaction mixture was degassed by bubbling with $N_2$ and sealed. The mixture was heated to 75° C. for 24 h. The resin (3 Scheme 3) was filtered and washed with THF (once), 1:1 THF/water (twice), water (twice), methanol (twice), $CH_2Cl_2$ (twice), then dried under reduced pressure. To an aliquot of the resin described above (300 mg) in $CH_2Cl_2$ (8 mL) were added hexachloroethane (236 mg, 1 mmol) and triphenylphosphine (262 mg, 1 mmol), then the reaction vessel was gentled swirled for 16 h at room temperature. After washing with $CH_2Cl_2$ (8 mL×4) the resin (4 Scheme 28) was treated with a solution of $Br_2$ (150 μL) in $CH_2Cl_2$ (8 mL) for 20 min. The cleavage solution was filtered and the resin was rinsed with $CH_2Cl_2$ (3 mL). Concentration of the combined filtrates gave 2-bromo-5-chloromethylthiophene (10.7 mg, loading level was determined to be 0.17 mequiv/g); $^1$H N (300 MHz, $CDCl_3$) δ 4.74 (s, 2 H), 6.86 (d, J=3.9 Hz, 1 H), 6.93 (d, J=3.9 Hz, 1 H).

Preparation of 4-Iodobenzene Functionalized Linker (1 Scheme 29).

To a pre-swelled aminomethylated polystyrene resin (7 g, 1.02 mmole/g) in DMF (100 mL) were added 4-iodobenzoic acid (12.4 g, 50 mmol), hydroxybenzotriazole hydrate (6.8 g, 50 mmol), diisopropylethylamine (8.7 mL, 50 mmol), and 1,3-diisoproylycarbodiimide (7.8 mL, 50 mmol). The suspension was stirred for 2 days at 40° C., and the resin was washed with DMF, MeOH, dichloromethane (DCM), MeOH and dried under reduced pressure to provide the functionalized resin.

Preparation of 3-Iodobenzene Functionalized Linker (2 Scheme 29).

To a pre-swelled aminomethylated polystyrene resin (7 g, 1.02 mmole/g) in DMF (100 mL) were added 3-iodobenzoic acid (12.4 g, 50 mmol), hydroxybenzotrizole hydrate (6.8 g, 50 mmol), diisopropylethylamine (8.7 mL, 50 mmol), and 1,3-diisoproylycarbodiimide (7.8 mL, 50 mmol). The suspension was stirred for 2 days at 40° C., and the resin was washed with DMF, MeOH, dichloromethane (DCM), MeOH and dried under reduced pressure to provide the functionalized resin.

Hydroboration and Suzuki Coupling of 4-Allyldimethylsilylphenethyl Alcohol to the 3-Iodobenzene Functionalized Linker (2 Scheme 29).

To a solution of 4-allyldimethylsilylphenethyl alcohol (440 mg, 2 mmol) in dry THF (4 mL) under a $N_2$ atmosphere was added 9-BBN (4 mL, 0.5 M solution in THF, 2 mmol) dropwise at 0° C. The mixture was gradually warmed to room temperature and stirred for 4 h. THF was evaporated under reduced pressure and the reaction intermediate was dissolved in toluene (8 mL). After adding ground $K_3PO_4$ (424 mg, 4 mmol), resin (2 Scheme 29, 1.1 g), $Pd(PPh_3)_4$ (70 mg), the reaction mixture was degassed by bubbling with $N_2$ and sealed. The reaction flask was wrapped with aluminum foil and heated at 80° C. for 24 h. The resin was filtered and washed with MeOH (once), 1:1 MeOH/water (twice), water (twice), methanol (twice), $CH_2Cl_2$ (twice), then dried under reduced pressure. An aliquot of resin (100 mg) was treated with a solution of $Br_2$ (50 µL) in $CH_2Cl_2$ (8 mL) for 20 min. The cleavage solution was filtered and the resin was rinsed with $CH_2Cl_2$ (3 mL). Concentration of the combined filtrates gave 2-bromophenethyl alcohol (4 Scheme 29, 4 mg, loading level was determined to be 0.20 mequiv/g); $^1$H NMR (500 MHz, $CDCl_3$) δ 2.11 (bs, OH, 1 H), 2.86 (t, J=6.5 Hz, 2 H), 3.88 (t, J=6.5 Hz, 2 H), 7.14 (d, J=8.0 Hz, 2 H), 7.46 (d, J=8.0 Hz, 2 H); $^{13}$C NMR (125 MHz, $CDCl_3$) 38.7, 63.7, 129.9, 131.0, 131.9, 132.3.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A resin-bound compound of the formula:

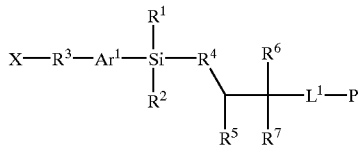

wherein
each of $R^1$ and $R^2$ is independently aryl, $C_1$–$C_6$ alkyl, or $C_3$–$C_{20}$ cycloalkyl;
$R^3$ is a bond or $C_1$–$C_{10}$ alkylene;
$R^4$ is $C_1$–$C_{10}$ alkylene;
each of $R^5$, $R^6$ and $R^7$ is independently H or $C_1$–$C_6$ alkyl;
$L^1$ is a bond or a linker;
P is a solid-support;
$Ar^1$ is aryl or heteroaryl; and
X is a functional group.

2. The resin-bound compound of claim 1, wherein $R^1$ and $R^2$ are methyl.

3. The resin-bound compound of claim 2, wherein $R^5$, $R^6$ and $R^7$ are H.

4. The resin-bound compound of claim 3, wherein $R^4$ is methylene.

5. The resin-bound compound of claim 4, wherein $Ar^1$ is optionally substituted phenyl, naphthyl, thiophenyl, pyridyl, bi-phenyl, quinolinyl, thiazinyl, isoquinolinyl, imidazolyl, furanyl, fluorenyl, indolyl, or indanyl.

6. The resin-bound compound of claim 5, wherein X is a halide, substituted aryl or heteroaryl, or a moiety of the formula $-NR^8R^9$, $-NHNR^{10}$, $-OR^{11}$, $-SR^{12}$, $-CN$, $-CHO$, $-CO_2R^{13}$, $-CR^{14}=CR^{15}CO_2R^{13}$, $-C(=O)NR^{16}R^{17}$, $-CR^{14}=CR^{15}C(=O)NR^{16}R^{17}$, $-CH[CH_2(NR^8R^9)]CO_2R^{13}$, or $-CH(NR^8R^9)CO_2R^{13}$,
wherein
each of $R^8$ and $R^9$ is independently H, $C_1$–$C_6$ alkyl, or an amine protecting group,
$R^{10}$ is H, $C_1$–$C_6$ alkyl, or a hydrazine protecting group;
$R^{11}$ is H, $C_1$–$C_6$ alkyl, or a hydroxy protecting group;
$R^{12}$ is H, $C_1$–$C_6$ alkyl, or a thiol protecting group;
each of $R^{13}$, $R^{14}$, and $R^{15}$ is independently H, or $C_1$–$C_6$ alkyl; and
each of $R^{16}$ and $R^{17}$ is independently H, $C_1$–$C_6$ alkyl, or an amide protecting group.

7. The resin-bound compound of claim 6, wherein X is substituted aryl or heteroaryl, $-NHR^9$, $-NHNR^{10}$, $-OR^{11}$, $-SR^{12}$, $-CN$, $-CHO$, $-CO_2R^{13}$, $-CH=CHCO_2R^{13}$, $-CH[CH_2(NR^8R^9)]CO_2R^{13}$, or $-CH(NR^8R^9)CO_2R^{13}$.

8. The resin-bound compound of claim 7, wherein said solid-support is polystyrene, aminomethylated polystyrene resin, aminomethylated Tentagel resin, polyamide-kieselguhr composites, Merrifield resin, Wang resin, or Rink resin.

9. The resin-bound compound of claim 8, wherein $L^1$ is a bond, $-O-$, or a moiety of the formula $-NHC(=O)-Ph-C(=O)NH-CH_2-P$.

* * * * *